(12) United States Patent
Bolduc et al.

(10) Patent No.: US 10,098,770 B2
(45) Date of Patent: Oct. 16, 2018

(54) ENDOVASCULAR ANEURYSM DEVICES, SYSTEMS, AND METHODS

(71) Applicant: Medtronic Vascular, Inc., Minneapolis, MN (US)

(72) Inventors: Lee Bolduc, Emerald Hills, CA (US); Andrew L Chiang, Fremont, CA (US); Jimmy Jen, San Jose, CA (US); Joshua Stafford, Menlo Park, CA (US)

(73) Assignee: MEDTRONIC VASCULAR, INC., Minneapolis, MN (US)

( * ) Notice: Subject to any disclaimer, the term of this patent is extended or adjusted under 35 U.S.C. 154(b) by 517 days.

(21) Appl. No.: 14/595,928

(22) Filed: Jan. 13, 2015

(65) Prior Publication Data

US 2015/0127015 A1    May 7, 2015

Related U.S. Application Data

(60) Continuation of application No. 11/488,305, filed on Jul. 18, 2006, now abandoned, which is a (Continued)

(51) Int. Cl.
*A61M 39/00* (2006.01)
*A61F 2/954* (2013.01)
(Continued)

(52) U.S. Cl.
CPC ............ *A61F 2/954* (2013.01); *A61B 17/064* (2013.01); *A61B 17/068* (2013.01); *A61F 2/07* (2013.01);
(Continued)

(58) Field of Classification Search
CPC ........... A61F 2002/9517; A61M 39/06; A61M 2039/062; A61M 2039/066
See application file for complete search history.

(56) References Cited

U.S. PATENT DOCUMENTS 2,033,039 A  3/1936 Limpert
3,499,222 A  3/1970 Linkow et al.
(Continued)

FOREIGN PATENT DOCUMENTS

AU  2002353807 B2  6/2003
AU  2004277897 B2  4/2005
(Continued)

OTHER PUBLICATIONS

"U.S. Appl. No. 10/099,149, Non Final Office Action dated Sep. 10, 2003", 6 pgs.
(Continued)

*Primary Examiner* — Diane Yabut

(57) ABSTRACT

Devices, systems, and methods for implanting prostheses in the body lumens rely on tacking or anchoring the prostheses with separately introduced fasteners. After initial placement, a fastener applier system is introduced within the expanded prostheses to deploy a plurality of fasteners to at least one prosthesis end. The fasteners are usually helical fasteners which are releasably restrained on the fastener driver, and are delivered by rotation of the fastener driver. The fasteners may be applied singly, typically in circumferentially spaced-apart patterns about the interior of at least one end of the prosthesis. A lumen extension or lumens may be coupled to the prosthesis to extend the reach of the prosthesis within the implantation site. Fasteners may also be applied to the lumen extensions.

23 Claims, 23 Drawing Sheets

Related U.S. Application Data continuation-in-part of application No. 11/255,116, filed on Oct. 20, 2005, now Pat. No. 7,637,932, and a continuation-in-part of application No. 10/692,283, filed on Oct. 23, 2003, now Pat. No. 7,147,657, said application No. 11/488,305 is a continuation-in-part of application No. 10/786,465, filed on Feb. 25, 2004, now Pat. No. 8,231,639, and a continuation-in-part of application No. 11/166,428, filed on Jun. 24, 2005, now abandoned, which is a division of application No. 10/693,255, filed on Oct. 24, 2003, now Pat. No. 6,929,661, said application No. 11/488,305 is a continuation-in-part of application No. 10/307,226, filed on Nov. 29, 2002, now Pat. No. 8,075,570, and a continuation-in-part of application No. 10/669,881, filed on Sep. 24, 2003, now Pat. No. 7,491,232, and a continuation-in-part of application No. 11/166,411, filed on Jun. 24, 2005, now Pat. No. 8,092,519, which is a division of application No. 10/271,334, filed on Oct. 15, 2002, now Pat. No. 6,960,217.

(60) Provisional application No. 60/488,753, filed on Jul. 21, 2003, provisional application No. 60/489,011, filed on Jul. 21, 2003, provisional application No. 60/333,937, filed on Nov. 28, 2001.

(51) Int. Cl.
| | |
|---|---|
| *A61B 17/064* | (2006.01) |
| *A61B 17/068* | (2006.01) |
| *A61F 2/07* | (2013.01) |
| *A61F 2/966* | (2013.01) |
| *A61M 39/06* | (2006.01) |
| *A61F 2/00* | (2006.01) |
| *A61F 2/06* | (2013.01) |
| *A61F 2/30* | (2006.01) |
| *A61F 2/95* | (2013.01) |
| *A61F 2/89* | (2013.01) |

(52) U.S. Cl.
CPC ...... *A61F 2/966* (2013.01); *A61B 2017/0649* (2013.01); *A61B 2017/0688* (2013.01); *A61F 2/0095* (2013.01); *A61F 2/064* (2013.01); *A61F 2/89* (2013.01); *A61F 2002/067* (2013.01); *A61F 2002/075* (2013.01); *A61F 2002/30617* (2013.01); *A61F 2002/9511* (2013.01); *A61F 2002/9517* (2013.01); *A61F 2250/0097* (2013.01); *A61M 39/06* (2013.01); *A61M 2039/062* (2013.01); *A61M 2039/066* (2013.01)

(56) References Cited

U.S. PATENT DOCUMENTS

| | | |
|---|---|---|
| 3,686,740 A | 8/1972 | Donald |
| 3,799,172 A | 3/1974 | Roman |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski et al. |
| 5,192,314 A | 3/1993 | Daskalakis |
| 5,195,968 A | 3/1993 | Lundquist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven et al. |
| 5,387,235 A | 2/1995 | Chuter |
| 5,409,498 A | 4/1995 | Braddock et al. |
| 5,456,713 A | 10/1995 | Chuter |
| 5,456,714 A | 10/1995 | Owen |
| 5,470,337 A | 11/1995 | Moss |
| 5,474,568 A | 12/1995 | Scott et al. |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Goicoechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dereume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | Mcdonald |
| 5,683,450 A | 11/1997 | Goicoechea et al. |
| 5,693,084 A | 12/1997 | Chuter |
| 5,693,086 A | 12/1997 | Goicoechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteladze et al. |
| 5,713,907 A | 2/1998 | Hogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,782,844 A | 7/1998 | Yoon et al. |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne et al. |
| 5,873,906 A | 2/1999 | Lau et al. |

(56) References Cited

U.S. PATENT DOCUMENTS

| | | |
|---|---|---|
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thompson et al. |
| 5,916,263 A | 6/1999 | Goicoechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner et al. |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard, III |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich, Jr. et al. |
| 6,168,610 B1 | 1/2001 | Marin et al. |
| 6,174,323 B1 | 1/2001 | Biggs et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,251,132 B1 | 6/2001 | Ravenscroft et al. |
| 6,258,021 B1 | 7/2001 | Wilk |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling et al. |
| 6,746,460 B2 | 6/2004 | Gannoe et al. |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,147,657 B2 | 12/2006 | Chiang et al. |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi |
| 7,563,267 B2 | 7/2009 | Goldfarb et al. |
| 7,591,842 B2 | 9/2009 | Parodi |
| 7,637,932 B2 | 12/2009 | Bolduc et al. |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc et al. |
| 7,828,267 B2 | 11/2010 | Iwabuchi et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,080,050 B2 | 12/2011 | Chiang et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 2001/0041821 A1 | 11/2001 | Wilk |
| 2001/0047199 A1 | 11/2001 | Wijay |
| 2002/0026144 A1 | 2/2002 | Patterson |
| 2002/0029077 A1 | 3/2002 | Leopold et al. |
| 2002/0058855 A1 | 5/2002 | Cyril, Jr. et al. |
| 2002/0065485 A1 | 5/2002 | Dubois |
| 2002/0087169 A1 | 7/2002 | Brock et al. |
| 2002/0099432 A1 | 7/2002 | Yee |

(56) References Cited

U.S. PATENT DOCUMENTS

| | | |
|---|---|---|
| 2002/0133054 A1 | 9/2002 | Murphy et al. |
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0004560 A1 | 1/2003 | Chobotov et al. |
| 2003/0018358 A1 | 1/2003 | Saadat |
| 2003/0060674 A1 | 3/2003 | Hanson, III et al. |
| 2003/0078465 A1 | 4/2003 | Pai et al. |
| 2003/0100943 A1 | 5/2003 | Bolduc |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0204249 A1 | 10/2003 | Letort |
| 2003/0233140 A1 | 12/2003 | Hartley et al. |
| 2004/0002731 A1 | 1/2004 | Aganon et al. |
| 2004/0039405 A1 | 2/2004 | Petrovic et al. |
| 2004/0044364 A1 | 3/2004 | Devries et al. |
| 2004/0049207 A1 | 3/2004 | Goldfarb et al. |
| 2004/0054352 A1 | 3/2004 | Adams et al. |
| 2004/0093057 A1 | 5/2004 | Bolduc et al. |
| 2004/0098079 A1* | 5/2004 | Hartley .............. A61F 2/95 623/1.11 |
| 2004/0127916 A1 | 7/2004 | Bolduc et al. |
| 2004/0138734 A1 | 7/2004 | Chobotov et al. |
| 2004/0153143 A1 | 8/2004 | Quiachon et al. |
| 2004/0186566 A1 | 9/2004 | Hindrichs et al. |
| 2004/0206363 A1 | 10/2004 | Mccarthy et al. |
| 2004/0210304 A1 | 10/2004 | Seguin et al. |
| 2004/0243170 A1 | 12/2004 | Suresh et al. |
| 2004/0254594 A1 | 12/2004 | Alfaro |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0154401 A1 | 7/2005 | Weldon et al. |
| 2005/0177180 A1 | 8/2005 | Kaganov et al. |
| 2005/0187613 A1 | 8/2005 | Bolduc et al. |
| 2005/0197716 A1 | 9/2005 | Sharkey et al. |
| 2005/0215874 A1 | 9/2005 | Wang et al. |
| 2005/0222603 A1* | 10/2005 | Andreas .............. A61F 2/958 606/194 |
| 2005/0240258 A1 | 10/2005 | Bolduc et al. |
| 2005/0240260 A1 | 10/2005 | Bolduc |
| 2006/0004433 A1* | 1/2006 | Greenberg .............. A61F 2/07 623/1.11 |
| 2006/0100640 A1 | 5/2006 | Bolduc |
| 2006/0129091 A1* | 6/2006 | Bonnette .............. A61B 17/22 604/93.01 |
| 2006/0184224 A1 | 8/2006 | Angel |
| 2006/0253186 A1 | 11/2006 | Bates |
| 2006/0259125 A1 | 11/2006 | Peacock, III |
| 2006/0287661 A1 | 12/2006 | Bolduc et al. |
| 2007/0021753 A1 | 1/2007 | Bolduc et al. |
| 2007/0021829 A1 | 1/2007 | Bolduc |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0046063 A1* | 2/2008 | Boatman .............. A61F 2/958 623/1.11 |
| 2008/0065115 A1 | 3/2008 | Parodi |
| 2008/0065117 A1 | 3/2008 | Bolduc |
| 2008/0065189 A1 | 3/2008 | Bolduc |
| 2008/0065191 A1 | 3/2008 | Bolduc et al. |
| 2008/0097489 A1 | 4/2008 | Goldfarb et al. |
| 2008/0132996 A1 | 6/2008 | Drasler et al. |
| 2008/0275393 A1* | 11/2008 | Bonnette .............. A61B 17/22 604/102.01 |
| 2009/0082852 A1 | 3/2009 | Bolduc et al. |
| 2009/0099650 A1 | 4/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2010/0094400 A1 | 4/2010 | Bolduc et al. |
| 2011/0087320 A1 | 4/2011 | Bolduc et al. |
| 2011/0238088 A1 | 9/2011 | Bolduc et al. |
| 2011/0276062 A1 | 11/2011 | Bolduc |
| 2012/0059450 A1 | 3/2012 | Chiang et al. |
| 2012/0065661 A1 | 3/2012 | Bolduc |
| 2012/0316578 A1 | 12/2012 | Bolduc et al. |
| 2014/0194902 A1 | 7/2014 | Bolduc et al. |
| 2014/0214051 A1 | 7/2014 | Bolduc |

FOREIGN PATENT DOCUMENTS

| | | |
|---|---|---|
| AU | 2005235108 A1 | 11/2005 |
| AU | 2008243229 A1 | 12/2008 |
| AU | 2004287355 B2 | 6/2011 |
| AU | 2011203524 A1 | 8/2011 |
| AU | 2006305688 B2 | 12/2012 |
| AU | 2011253682 B9 | 1/2014 |
| AU | 2011224089 B2 | 7/2014 |
| CA | 2265131 A1 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 10034105 C1 | 4/2002 |
| DE | 10297483 T5 | 12/2004 |
| EP | 0321912 A1 | 6/1989 |
| EP | 0663184 A1 | 7/1995 |
| EP | 0835642 B1 | 2/2002 |
| EP | 1369098 A1 | 12/2003 |
| EP | 1440673 A1 | 7/2004 |
| EP | 1448117 A1 | 8/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 1682039 | 8/2009 |
| EP | 2119416 A1 | 11/2009 |
| EP | 2349086 A1 | 8/2011 |
| EP | 2349087 A1 | 8/2011 |
| FR | 2299548 A1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001526574 A | 12/2001 |
| JP | 2002526193 A | 8/2002 |

(56) References Cited

FOREIGN PATENT DOCUMENTS

| | | | |
|---|---|---|---|
| JP | 2005046648 A | 2/2005 |
| JP | 2005510293 A | 4/2005 |
| JP | 2005510303 A | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009095684 A | 5/2009 |
| JP | 2009106763 A | 5/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-9300868 A1 | 1/1993 |
| WO | WO-9521592 A1 | 8/1995 |
| WO | WO-9603925 A1 | 2/1996 |
| WO | WO-9703616 A1 | 2/1997 |
| WO | WO-1997003616 A1 | 2/1997 |
| WO | WO-9712562 A1 | 4/1997 |
| WO | WO-9717039 A1 | 5/1997 |
| WO | WO-9717913 A1 | 5/1997 |
| WO | WO-9811814 A2 | 3/1998 |
| WO | WO-9853761 A1 | 12/1998 |
| WO | WO-9930637 A1 | 6/1999 |
| WO | WO-9933402 A1 | 7/1999 |
| WO | WO-9933402 A9 | 9/1999 |
| WO | WO-9953845 A1 | 10/1999 |
| WO | WO-1999053845 A1 | 10/1999 |
| WO | WO-0064357 A1 | 1/2000 |
| WO | WO-0016701 A1 | 3/2000 |
| WO | WO-0035350 A1 | 6/2000 |
| WO | WO-0160432 A1 | 8/2001 |
| WO | WO-03032870 A1 | 4/2003 |
| WO | WO-03045283 A1 | 6/2003 |
| WO | WO-03045467 A2 | 6/2003 |
| WO | WO-03045467 A3 | 7/2003 |
| WO | WO-03079935 A1 | 10/2003 |
| WO | WO-2004008975 A1 | 1/2004 |
| WO | WO-2004021872 A2 | 3/2004 |
| WO | WO-2005032333 A2 | 4/2005 |
| WO | WO-2005037076 A2 | 4/2005 |
| WO | WO-2005044073 A2 | 5/2005 |
| WO | WO-2005044147 A1 | 5/2005 |
| WO | WO-2005044148 A1 | 5/2005 |
| WO | WO-2005067660 A2 | 7/2005 |
| WO | WO-2005081936 A2 | 9/2005 |
| WO | WO-2007046955 A3 | 10/2005 |
| WO | WO-2005102181 A1 | 11/2005 |
| WO | WO-2005032333 A3 | 4/2006 |
| WO | WO-2005067660 A3 | 4/2007 |
| WO | WO-2007046953 A2 | 4/2007 |
| WO | WO-2007046954 A2 | 4/2007 |
| WO | WO-2007046955 A2 | 4/2007 |
| WO | WO-2007047023 A2 | 4/2007 |
| WO | WO-2007053233 A2 | 5/2007 |
| WO | WO-2007046953 A3 | 6/2007 |
| WO | WO-2007047023 A3 | 10/2007 |
| WO | WO-2005081936 A3 | 11/2007 |
| WO | WO-2007053233 A3 | 1/2008 |
| WO | WO-2007046954 A3 | 11/2008 |
| WO | WO-2005044073 A3 | 3/2009 |
| WO | WO-2010004856 A1 | 1/2010 |
| WO | WO-2010044851 A1 | 4/2010 |
| WO | WO-2010044854 A1 | 4/2010 |
| WO | WO-2010044855 A1 | 4/2010 |
| WO | WO-2010044856 A1 | 4/2010 |

OTHER PUBLICATIONS

"U.S. Appl. No. 10/099,149, Notice of Allowance dated Jun. 24, 2004", 4 pgs.

"U.S. Appl. No. 10/099,149, Response filed Mar. 12, 2004 to Non Final Office Action dated Sep. 10, 2003", 5 pgs.

"U.S. Appl. No. 11/254,619, Advisory Action dated Sep. 24, 2014", 3 pgs.

"U.S. Appl. No. 11/254,619, Examiner Interview Summary dated Sep. 18, 2014", 3 pgs.

"U.S. Appl. No. 11/254,619, Final Office Action dated Jun. 19, 2014", 17 pgs.

"U.S. Appl. No. 11/254,619, Final Office Action dated Jun. 30, 2010", 10 pgs.

"U.S. Appl. No. 11/254,619, Final Office Action dated Oct. 20, 2011", 11 pgs.

"U.S. Appl. No. 11/254,619, Non Final Office Action dated Feb. 3, 2011", 8 pgs.

"U.S. Appl. No. 11/254,619, Non Final Office Action dated Oct. 1, 2009", 5 pgs.

"U.S. Appl. No. 11/254,619, Response filed May 6, 2014 to Non Final Office Action dated Jan. 6, 2014", 10 pgs.

"U.S. Appl. No. 11/254,619, Response filed Sep. 15, 2014 to Final Office Action dated Jun. 19, 2014", 12 pgs.

"U.S. Appl. No. 11/981,112, Examiner Interview Summary dated Jul. 3, 2014", 3 pgs.

"U.S. Appl. No. 11/981,112, Final Office Action dated Oct. 24, 2014", 7 pgs.

"U.S. Appl. No. 11/981,112, Response filed Jan. 12, 2014 to Final Office Action dated Oct. 24, 2014", 9 pgs.

"U.S. Appl. No. 11/981,112, Response filed Jun. 27, 2014 to Non Final Office Action dated Feb. 28, 2014", 11 pgs.

"U.S. Appl. No. 12/288,031, Advisory Action dated Jul. 7, 2014", 4 pgs.

"U.S. Appl. No. 12/288,031, Non Final Office Action dated May 10, 2012", 7 pgs.

"U.S. Appl. No. 12/288,031, Response filed Jun. 5, 2014 to Final Office Action dated Mar. 12, 2014", 15 pgs.

"U.S. Appl. No. 12/288,031, Response filed Sep. 10, 2014 to Advisory Action dated Jul. 7, 2014", 16 pgs.

"U.S. Appl. No. 12/288,034, Final Office Action dated Dec. 1, 2014", 8 pgs.

"U.S. Appl. No. 12/288,034, Non Final Office Action dated May 8, 2014", 8 pgs.

"U.S. Appl. No. 12/288,034, Response filed Aug. 1, 2014 to Non Final Office Action dated May 8, 2014", 11 pgs.

"U.S. Appl. No. 12/315,015, Examiner Interview Summary dated Nov. 28, 2014", 3 pgs.

"U.S. Appl. No. 12/315,015, Non Final Office Action dated Aug. 4, 2014", 7 pgs.

"U.S. Appl. No. 12/315,015, Response filed Jun. 17, 2014 to Final Office Action dated Jan. 28, 2014", 7 pgs.

"U.S. Appl. No. 12/315,015, Response filed Nov. 4, 2014 to Non-Final Office Action dated Aug. 4, 2014", 7 pgs.

"U.S. Appl. No. 12/942,232, Advisory Action dated Aug. 7, 2014", 3 pgs.

"U.S. Appl. No. 12/942,232, Final Office Action dated May 22, 2014", 17 pgs.

"U.S. Appl. No. 12/942,232, Response filed Jul. 21, 2014 to Final Office Action dated May 22, 2014", 11 pgs.

"U.S. Appl. No. 13/157,242, Notice of Allowance dated May 9, 2014", 8 pgs.

"U.S. Appl. No. 13/157,242, Notice of Allowance dated Aug. 21, 2014", 8 pgs.

"U.S. Appl. No. 13/162,384, Examiner Interview Summary dated Oct. 22, 2014", 3 pgs.

"U.S. Appl. No. 13/162,384, Non Final Office Action dated Jul. 21, 2014", 15 pgs.

(56) References Cited

OTHER PUBLICATIONS

"U.S. Appl. No. 13/162,384, Response filed Oct. 20, 2014 to Non Final Office Action dated Jul. 21, 2014", 12 pgs.
"U.S. Appl. No. 13/291,942, Non Final Office Action dated Oct. 21, 2014", 10 pgs.
"U.S. Appl. No. 14/210,683, Preliminary Amendment dated Mar. 24, 2014", 7 pgs.
"Australian Application Serial No. 2004287353, Office Action dated Oct. 13, 2009", 3 pgs.
"Australian Application Serial No. 2011224089, Response filed Mar. 21, 2014 to First Examiners Report dated Mar. 27, 2013", 74 pgs.
"Australian Serial No. 2011203524, First Examiner Report dated Jul. 16, 2012", 3 pgs.
"European Application Serial No. 04782144.2, Office Action dated Jun. 12, 2006", 2 pgs.
"European Application Serial No. 04782144.2, Office Action dated Oct. 30, 2007", 4 pgs.
"European Application Serial No. 04782144.2, Response filed Mar. 5, 2008 to Office Action dated Oct. 30, 2007", 18 pgs.
"European Application Serial No. 04782144.2, Response filed Dec. 24, 2008 to Summons to Attend Oral Proceedings dated Sep. 11, 2008", 5 pgs.
"European Application Serial No. 04782144.2, Summons to Attend Oral Proceedings dated Sep. 11, 2008", 3 pgs.
"European Application Serial No. 04782144.2, Supplementary European Search Report dated Mar. 19, 2007", 3 pgs.
"European Application Serial No. 04788653.6, European Search Report dated Aug. 6, 2014", 3 pgs.
"European Application Serial No. 04788653.6, Response filed Oct. 21, 2014 to European Search Report dated Aug. 6, 2014", 4 pgs.
"European Application Serial No. 05713941.2, European Search Report dated Apr. 10, 2014", 6 pgs.
"European Application Serial No. 05713941.2, Examination Notification Art. 94(3) dated Jun. 5, 2014", 7 pgs.
"European Application Serial No. 05723408.0, Examination Notification Art. 94(3) dated Jul. 10, 2014", 6 pgs.
"European Application Serial No. 06802580.8, Response filed Apr. 17, 2014 to Extended European Search Report dated Sep. 24, 2013", 2 pgs.
"5mm Origin Tracker It Runs In Circles Around Staples", Guidant Origin Advertising Literature, (1995), 2 pgs.
"U.S. Appl. No. 10/271,334, Examiner Interview Summary dated Feb. 11, 2005", 2 pgs.
"U.S. Appl. No. 10/271,334, Non Final Office Action dated May 18, 2004", 9 pgs.
"U.S. Appl. No. 10/271,334, Notice of Allowance dated Feb. 11, 2005", 6 pgs.
"U.S. Appl. No. 10/271,334, Notice of Allowance dated Mar. 17, 2005", 3 pgs.
"U.S. Appl. No. 10/271,334, Notice of Allowance dated Aug. 26, 2005", 3 pgs.
"U.S. Appl. No. 10/271,334, Response filed Mar. 15, 2004 to Restriction Requirement dated Sep. 23, 2003", 1 pg.
"U.S. Appl. No. 10/271,334, Response filed Nov. 22, 2004 to Non Final Office Action dated May 18, 2004", 6 pgs.
"U.S. Appl. No. 10/271,334, Restriction Requirement dated Sep. 23, 2003", 4 pgs.
"U.S. Appl. No. 10/271,334, Supplemental Response filed Jan. 28, 2005 to Non Final Office Action dated May 18, 2004", 6 pgs.
"U.S. Appl. No. 10/307,226, 312 Amendment filed Oct. 24, 2011", 3 pgs.
"U.S. Appl. No. 10/307,226, Appeal Brief filed Oct. 14, 2010", 15 pgs.
"U.S. Appl. No. 10/307,226, Final Office Action dated Jun. 27, 2008", 6 pgs.
"U.S. Appl. No. 10/307,226, Final Office Action dated Dec. 12, 2006", 5 pgs.
"U.S. Appl. No. 10/307,226, Non Final Office Action dated Mar. 13, 2006", 6 pgs.
"U.S. Appl. No. 10/307,226, Non Final Office Action dated Jun. 12, 2007", 5 pgs.
"U.S. Appl. No. 10/307,226, Non Final Office Action dated Sep. 9, 2009", 16 pgs.
"U.S. Appl. No. 10/307,226, Notice of Allowance dated Jul. 22, 2011", 8 pgs.
"U.S. Appl. No. 10/307,226, Preliminary Amendment filed Jul. 22, 2005", 3 pgs.
"U.S. Appl. No. 10/307,226, PTO Response to 312 Amendment dated Nov. 10, 2011", 3 pgs.
"U.S. Appl. No. 10/307,226, Response filed Apr. 9, 2007 to Final Office Action dated Dec. 12, 2006", 7 pgs.
"U.S. Appl. No. 10/307,226, Response filed Jun. 23, 2009 to Final Office Action dated Jun. 27, 2008", 10 pgs.
"U.S. Appl. No. 10/307,226, Response filed Sep. 15, 2006 to Non Final Office Action dated Mar. 13, 2006", 6 pgs.
"U.S. Appl. No. 10/307,226, Response filed Dec. 14, 2007 to Non Final Office Action dated Jun. 12, 2007", 7 pgs.
"U.S. Appl. No. 10/669,881, Final Office Action dated Jan. 25, 2008", 7 pgs.
"U.S. Appl. No. 10/669,881, Non Final Office Action dated Jan. 27, 2006", 5 pgs.
"U.S. Appl. No. 10/669,881, Notice of Allowance dated Oct. 8, 2008", 16 pgs.
"U.S. Appl. No. 10/669,881, Preliminary Amendment May 6, 2005", 3 pgs.
"U.S. Appl. No. 10/669,881, Response filed Mar. 11, 2008 to Final Office Action dated Jan. 25, 2008", 8 pgs.
"U.S. Appl. No. 10/669,881, Response filed May 15, 2006 to Non Final Office Action dated Jan. 27, 2006", 9 pgs.
"U.S. Appl. No. 10/669,881, Response filed Sep. 7, 2007 to Restriction Requirement dated Jun. 19, 2007", 4 pgs.
"U.S. Appl. No. 10/669,881, Response filed Oct. 2, 2006 to Restriction Requirement dated Jul. 27, 2006", 6 pgs.
"U.S. Appl. No. 10/669,881, Restriction Requirement Jul. 27, 2006", 5 pgs.
"U.S. Appl. No. 10/669,881, Restriction Requirement dated Jun. 19, 2007", 5 pgs.
"U.S. Appl. No. 10/692,282, Non Final Office Action dated Aug. 30, 2005", 6 pgs.
"U.S. Appl. No. 10/692,282, Notice of Allowance dated Jun. 13, 2006", 6 pgs.
"U.S. Appl. No. 10/692,282, Response filed Feb. 22, 2005 to Restriction Requirement dated Aug. 17, 2004", 4 pgs.
"U.S. Appl. No. 10/692,282, Response filed Feb. 28, 2006 to Non Final Office Action dated Aug. 30, 2005", 5 pgs.
"U.S. Appl. No. 10/692,282, Restriction Requirement dated Aug. 17, 2004", 6 pgs.
"U.S. Appl. No. 10/692,283, Non Final Office Action dated Nov. 16, 2005", 6 pgs.
"U.S. Appl. No. 10/692,283, Notice of Allowance dated Aug. 1, 2006", 4 pgs.
"U.S. Appl. No. 10/692,283, Preliminary Amendment filed Nov. 22, 2004", 3 pgs.
"U.S. Appl. No. 10/692,283, Response filed May 19, 2006 to Non Final Office Action dated Nov. 16, 2005", 5 pgs.
"U.S. Appl. No. 10/693,255, Examiner Interview Summary dated Feb. 17, 2005", 3 pgs.
"U.S. Appl. No. 10/693,255, Non Final Office Action dated Dec. 9, 2004", 6 pgs.
"U.S. Appl. No. 10/693,255, Notice of Allowance dated Mar. 9, 2005", 9 pgs.
"U.S. Appl. No. 10/693,255, Response filed Feb. 17, 2005 to Non Final Office Action dated Dec. 9, 2004", 6 pgs.
"U.S. Appl. No. 10/752,435, Final Office Action dated May 14, 2010", 8 pgs.
"U.S. Appl. No. 10/752,435, Final Office Action dated Jul. 12, 2007", 8 pgs.
"U.S. Appl. No. 10/752,435, Final Office Action dated Dec. 8, 2008", 8 pgs.
"U.S. Appl. No. 10/752,435, Non Final Office Action dated Mar. 18, 2008", 7 pgs.

(56) References Cited

OTHER PUBLICATIONS

"U.S. Appl. No. 10/752,435, Non Final Office Action dated Jul. 21, 2009", 7 pgs.
"U.S. Appl. No. 10/752,435, Non Final Office Action dated Oct. 19, 2006", 17 pgs.
"U.S. Appl. No. 10/752,435, Response filed Jan. 9, 2008 to Final Office Action dated Jul. 12, 2007", 10 pgs.
"U.S. Appl. No. 10/752,435, Response filed Jan. 25, 2010 to Non Final Office Action dated Jul. 21, 2009", 9 pgs.
"U.S. Appl. No. 10/752,435, Response filed Apr. 9, 2007 to Non Final Office Action dated Oct. 19, 2006", 13 pgs.
"U.S. Appl. No. 10/752,435, Response filed May 12, 2009 to Final Office Action dated Dec. 8, 2008", 9 pgs.
"U.S. Appl. No. 10/752,435, Response filed Sep. 19, 2008 to Non Final Office Action dated Mar. 18, 2008", 7 pgs.
"U.S. Appl. No. 10/786,465, Applicant's Summary of Examiner Interview filed Jun. 6, 2012", 2 pgs.
"U.S. Appl. No. 10/786,465, Corrected Notice of Allowability dated Jul. 2, 2012", 4 pgs.
"U.S. Appl. No. 10/786,465, Examiner Interview Summary dated Mar. 3, 2008", 2 pgs.
"U.S. Appl. No. 10/786,465, Examiner Interview Summary dated Apr. 26, 2011", 3 pgs.
"U.S. Appl. No. 10/786,465, Final Office Action dated Jan. 21, 2009", 8 pgs.
"U.S. Appl. No. 10/786,465, Non Final Office Action dated Mar. 26, 2010", 8 pgs.
"U.S. Appl. No. 10/786,465, Non Final Office Action dated Jul. 23, 2007", 7 pgs.
"U.S. Appl. No. 10/786,465, Notice of Allowance dated Mar. 14, 2012", 11 pgs.
"U.S. Appl. No. 10/786,465, Preliminary Amendment filed May 16, 2005", 3 pgs.
"U.S. Appl. No. 10/786,465, Response filed Jan. 25, 2008 to Non Final Office Action dated Jul. 23, 2007", 8 pgs.
"U.S. Appl. No. 10/786,465, Response filed Apr. 9, 2007 to Restriction Requirement dated Dec. 8, 2006", 4 pgs.
"U.S. Appl. No. 10/786,465, Response filed Apr. 26, 2011 to Non Final Office Action dated Mar. 26, 2010", 14 pgs.
"U.S. Appl. No. 10/786,465, Response filed Jul. 22, 2009 to Final Office Action dated Jan. 21, 2009", 5 pgs.
"U.S. Appl. No. 10/786,465, Response filed Sep. 19, 2008 to Restriction Requirement dated Jul. 24, 2008", 4 pgs.
"U.S. Appl. No. 10/786,465, Restriction Requirement dated Jul. 24, 2008", 5 pgs.
"U.S. Appl. No. 10/786,465, Restriction Requirement dated Dec. 8, 2006", 6 pgs.
"U.S. Appl. No. 10/786,465, Supplemental Amendment filed Mar. 18, 2008", 8 pgs.
"U.S. Appl. No. 10/786,465, Supplemental Notice of Allowability dated May 8, 2012", 6 pgs.
"U.S. Appl. No. 10/808,216, Preliminary Amendment filed Jun. 15, 2005", 3 pgs.
"U.S. Appl. No. 11/166,411, 312 Amendment filed Nov. 23, 2011", 3 pgs.
"U.S. Appl. No. 11/166,411, Final Office Action dated Dec. 3, 2009", 5 pgs.
"U.S. Appl. No. 11/166,411, Non Final Office Action dated May 5, 2009", 8 pgs.
"U.S. Appl. No. 11/166,411, Notice of Allowance dated Jan. 6, 2011", 4 pgs.
"U.S. Appl. No. 11/166,411, Notice of Allowance dated Aug. 23, 2011", 5 pgs.
"U.S. Appl. No. 11/166,411, Preliminary Amendment filed Oct. 2, 2006", 5 pgs.
"U.S. Appl. No. 11/166,411, PTO Response to 312 Amendment dated Dec. 13, 2011", 2 pgs.
"U.S. Appl. No. 11/166,411, Response filed Jan. 12, 2009 to Restriction Requirement dated Jul. 15, 2008", 5 pgs.
"U.S. Appl. No. 11/166,411, Response filed Jun. 7, 2010 to Final Office Action dated Dec. 3, 2009", 5 pgs.
"U.S. Appl. No. 11/166,411, Response filed Nov. 9, 2009 to Non Final Office Action dated May 5, 2009", 8 pgs.
"U.S. Appl. No. 11/166,411, Restriction Requirement dated Jul. 15, 2008", 5 pgs.
"U.S. Appl. No. 11/166,411, Supplemental Preliminary Amendment filed Oct. 30, 2007", 7 pgs.
"U.S. Appl. No. 11/166,428, Final Office Action dated Jan. 12, 2009", 10 pgs.
"U.S. Appl. No. 11/166,428, Final Office Action dated Mar. 16, 2010", 8 pgs.
"U.S. Appl. No. 11/166,428, Non Final Office Action dated May 14, 2008", 6 pgs.
"U.S. Appl. No. 11/166,428, Non Final Office Action dated Jun. 16, 2009", 10 pgs.
"U.S. Appl. No. 11/166,428, Response filed May 12, 2009 to Final Office Action dated Jan. 12, 2009", 6 pgs.
"U.S. Appl. No. 11/166,428, Response filed Nov. 17, 2008 to Non Final Office Action dated May 14, 2008", 6 pgs.
"U.S. Appl. No. 11/166,428, Response filed Dec. 22, 2009 to Non Final Office Action dated Dec. 16, 2009", 8 pgs.
"U.S. Appl. No. 11/254,444, Notice of Allowance dated Mar. 9, 2010", 7 pgs.
"U.S. Appl. No. 11/254,444, Notice of Allowance dated Apr. 5, 2010", 4 pgs.
"U.S. Appl. No. 11/254,444, Notice of Allowance dated Jun. 29, 2010", 6 pgs.
"U.S. Appl. No. 11/254,444, Preliminary Amendment filed Oct. 20, 2005", 8 pgs.
"U.S. Appl. No. 11/254,444, Preliminary Amendment filed Nov. 15, 2005", 8 pgs.
"U.S. Appl. No. 11/254,444, Response filed Dec. 18, 2009 to Restriction Requirement dated Jun. 19, 2009", 2 pgs.
"U.S. Appl. No. 11/254,444, Restriction Requirement dated Jun. 19, 2009", 6 pgs.
"U.S. Appl. No. 11/254,619, Final Office Action dated Jun. 30, 2010", 11 pgs.
"U.S. Appl. No. 11/254,619, Final Office Action dated Oct. 20, 2011", 12 pgs.
"U.S. Appl. No. 11/254,619, Non Final Office Action dated Jan. 6, 2014", 19 pgs.
"U.S. Appl. No. 11/254,619, Non Final Office Action dated Feb. 3, 2011", 9 pgs.
"U.S. Appl. No. 11/254,619, Non Final Office Action dated Oct. 1, 2009", 6 pgs.
"U.S. Appl. No. 11/254,619, Response filed Apr. 1, 2010 to Non Final Office Action dated Oct. 1, 2009", 5 pgs.
"U.S. Appl. No. 11/254,619, Response filed Apr. 20, 2012 to Final Office Action dated Oct. 20, 2011", 11 pgs.
"U.S. Appl. No. 11/254,619, Response filed Aug. 3, 2011 to Non Final Office Action dated Feb. 3, 2011", 13 pgs.
"U.S. Appl. No. 11/254,619, Response filed Dec. 29, 2010 to Final Office Action dated Jun. 30 ,2010", 12 pgs.
"U.S. Appl. No. 11/254,950, Non Final Office Action dated Mar. 30, 2009", 6 pgs.
"U.S. Appl. No. 11/254,950, Notice of Allowance dated Feb. 26, 2010", 4 pgs.
"U.S. Appl. No. 11/254,950, Notice of Allowance dated Jun. 22, 2010", 4 pgs.
"U.S. Appl. No. 11/254,950, Preliminary Amendment filed Nov. 18, 2005", 4 pgs.
"U.S. Appl. No. 11/254,950, Response filed Jan. 5, 2009 to Restriction Requirement dated Jul. 9, 2008", 7 pgs.
"U.S. Appl. No. 11/254,950, Response filed Oct. 5, 2009 to Non Final Office Action dated Mar. 30, 2009", 5 pgs.
"U.S. Appl. No. 11/254,950, Restriction Requirement dated Jul. 9, 2008", 9 pgs.
"U.S. Appl. No. 11/255,116, Non Final Office Action dated May 14, 2008", 15 pgs.
"U.S. Appl. No. 11/255,116, Notice of Allowance dated Aug. 10, 2009", 4 pgs.

(56) References Cited

OTHER PUBLICATIONS

"U.S. Appl. No. 11/255,116, Preliminary Amendment filed Nov. 18, 2005", 4 pgs.
"U.S. Appl. No. 11/255,116, Response filed May 20, 2009 to Restriction Requirement dated Mar. 18, 2009", 4 pgs.
"U.S. Appl. No. 11/255,116, Response filed Nov. 17, 2008 to Non Final Office Action dated May 24, 2008", 7 pgs.
"U.S. Appl. No. 11/255,116, Restriction Requirement dated Mar. 18, 2009", 7 pgs.
"U.S. Appl. No. 11/365,056, Final Office Action dated Dec. 9, 2010", 13 pgs.
"U.S. Appl. No. 11/365,056, Non Final Office Action dated Mar. 23, 2010", 11 pgs.
"U.S. Appl. No. 11/365,056, Response filed Sep. 28, 2010 to Non Final Office Action dated Mar. 23, 2010", 5 pgs.
"U.S. Appl. No. 11/365,056, Response filed Dec. 10, 2009 to Restriction Requirement dated Jun. 10, 2009", 44 pgs.
"U.S. Appl. No. 11/365,056, Restriction Requirement dated Jun. 10, 2009", 5 pgs.
"U.S. Appl. No. 11/488,305, Advisory Action dated Jun. 7, 2013", 3 pgs.
"U.S. Appl. No. 11/488,305, Final Office Action dated Mar. 6, 2013", 9 pgs.
"U.S. Appl. No. 11/488,305, Final Office Action dated Apr. 13, 2011", 9 pgs.
"U.S. Appl. No. 11/488,305, Final Office Action dated Aug. 14, 2014", 11 pgs.
"U.S. Appl. No. 11/488,305, Non Final Office Action dated Jan. 29, 2014", 10 pgs.
"U.S. Appl. No. 11/488,305, Non Final Office Action dated Sep. 1, 2010", 8 pgs.
"U.S. Appl. No. 11/488,305, Non Final Office Action dated Sep. 14, 2012", 9 pgs.
"U.S. Appl. No. 11/488,305, Non Final Office Action dated Oct. 31, 2011", 6 pgs.
"U.S. Appl. No. 11/488,305, Response filed Feb. 1, 2011 to Non Final Office Action dated Sep. 1, 2010", 12 pgs.
"U.S. Appl. No. 11/488,305, Response filed Feb. 13, 2013 to Non Final Office Action dated Sep. 14, 2012", 10 pgs.
"U.S. Appl. No. 11/488,305, Response filed Apr. 26, 2012 to Non Final Office Action dated Oct. 31, 2011", 12 pgs.
"U.S. Appl. No. 11/488,305, Response filed Apr. 29, 2014 to Non Final Office Action dated Jan. 29, 2014", 9 pgs.
"U.S. Appl. No. 11/488,305, Response filed May 3, 2013 to Final Office Action dated Mar. 6, 2013", 11 pgs.
"U.S. Appl. No. 11/488,305, Response filed Jul. 2, 2010 to Restriction Requirement dated Jan. 5, 2010", 8 pgs.
"U.S. Appl. No. 11/488,305, Response filed Oct. 13, 2011 to Final Office Action dated Apr. 13, 2011", 11 pgs.
"U.S. Appl. No. 11/488,305, Restriction Requirement dated Jan. 5, 2010", 6 pgs.
"U.S. Appl. No. 11/540,427, Appeal Brief filed Aug. 26, 2010", 26 pgs.
"U.S. Appl. No. 11/540,427, Final Office Action dated Jul. 21, 2009", 9 pgs.
"U.S. Appl. No. 11/540,427, Non Final Office Action dated Oct. 6, 2008", 10 pgs.
"U.S. Appl. No. 11/540,427, Notice of Allowance dated Apr. 11, 2011", 8 pgs.
"U.S. Appl. No. 11/540,427, Notice of Allowance dated Apr. 29, 2011", 8 pgs.
"U.S. Appl. No. 11/540,427, Preliminary Amendment filed Oct. 3, 2007", 5 pgs.
"U.S. Appl. No. 11/540,427, Response filed Apr. 10, 2009 to Non Final Office Action dated Oct. 6, 2008", 6 pgs.
"U.S. Appl. No. 11/540,428, Final Office Action dated Aug. 4, 2011", 9 pgs.
"U.S. Appl. No. 11/540,428, Non Final Office Action dated Nov. 12, 2010", 8 pgs.
"U.S. Appl. No. 11/540,428, Response filed May 12, 2011 to Non Final Office Action dated Nov. 12, 2010", 12 pgs.
"U.S. Appl. No. 11/540,428, Response filed Oct. 1, 2010 to Restriction Requirement dated Mar. 29, 2010", 6 pgs.
"U.S. Appl. No. 11/540,428, Restriction Requirement dated Mar. 29, 2010", 9 pgs.
"U.S. Appl. No. 11/580,584, Appeal Brief filed Nov. 15, 2010", 11 pgs.
"U.S. Appl. No. 11/580,584, Final Office Action dated Jan. 22, 2009", 9 pgs.
"U.S. Appl. No. 11/580,584, Final Office Action dated Oct. 16, 2009", 8 pgs.
"U.S. Appl. No. 11/580,584, Non Final Office Action dated Apr. 18, 2008", 6 pgs.
"U.S. Appl. No. 11/580,584, Notice of Allowance dated Feb. 4, 2011", 7 pgs.
"U.S. Appl. No. 11/580,584, Response filed Jul. 22, 2009 to Final Office Action dated Jan. 22, 2009", 6 pgs.
"U.S. Appl. No. 11/580,584, Response filed Oct. 20, 2008 to Non Final Office Action dated Apr. 18, 2008", 5 pgs.
"U.S. Appl. No. 11/633,724, 312 Amendment filed Nov. 8, 2011", 4 pgs.
"U.S. Appl. No. 11/633,724, Final Office Action dated Jun. 22, 2010", 6 pgs.
"U.S. Appl. No. 11/633,724, Final Office Action dated Dec. 8, 2009", 5 pgs.
"U.S. Appl. No. 11/633,724, Notice of Allowance dated Jan. 7, 2011", 4 pgs.
"U.S. Appl. No. 11/633,724, Notice of Allowance dated Aug. 8, 2011", 5 pgs.
"U.S. Appl. No. 11/633,724, PTO Response to 312 Amendment dated Nov. 17, 2011", 2 pgs.
"U.S. Appl. No. 11/633,724, Response filed Jun. 8, 2010 to Final Office Action dated Dec. 8, 2009", 4 pgs.
"U.S. Appl. No. 11/633,724, Response filed Dec. 22, 2010 to Non Final Office Action dated Dec. 8, 2009", 6 pgs.
"U.S. Appl. No. 11/978,752, Final Office Action dated Dec. 22, 2010", 6 pgs.
"U.S. Appl. No. 11/978,752, Non Final Office Action dated May 20, 2010", 6 pgs.
"U.S. Appl. No. 11/978,752, Notice of Allowance dated Aug. 31, 2011", 5 pgs.
"U.S. Appl. No. 11/978,752, Response filed May 10, 2010 to Restriction Requirement dated Nov. 6, 2009", 4 pgs.
"U.S. Appl. No. 11/978,752, Response filed Jun. 22, 2011 to Final Office Action dated Dec. 22, 2010", 6 pgs.
"U.S. Appl. No. 11/978,752, Response filed Nov. 5, 2010 to Non Final Office Action dated May 20, 2010", 4 pgs.
"U.S. Appl. No. 11/978,752, Restriction Requirement dated Nov. 6, 2009", 7 pgs.
"U.S. Appl. No. 11/978,753, Final Office Action dated May 2, 2011", 8 pgs.
"U.S. Appl. No. 11/978,753, Non Final Office Action dated Sep. 3, 2010", 8 pgs.
"U.S. Appl. No. 11/978,753, Response filed Mar. 3, 2011 to Non Final Office Action dated Sep. 3, 2010", 9 pgs.
"U.S. Appl. No. 11/981,112, Advisory Action dated Jan. 31, 2014", 3 pgs.
"U.S. Appl. No. 11/981,112, Final Office Action dated Apr. 29, 2010", 9 pgs.
"U.S. Appl. No. 11/981,112, Final Office Action dated Oct. 8, 2013", 9 pgs.
"U.S. Appl. No. 11/981,112, Non Final Office Action dated Feb. 28, 2014", 9 pgs.
"U.S. Appl. No. 11/981,112, Non Final Office Action dated Jul. 8, 2009", 11 pgs.
"U.S. Appl. No. 11/981,112, Response filed Jan. 8, 2014 to Final Office Action dated Oct. 8, 2013", 11 pgs.
"U.S. Appl. No. 11/981,112, Response filed Jan. 6, 2010 to Non Final Office Action dated Jul. 8, 2009", 7 pgs.
"U.S. Appl. No. 11/981,112, Response filed Nov. 1, 2010 to Final Office Action dated Apr. 29, 2010", 7 pgs.

(56) References Cited

OTHER PUBLICATIONS

"U.S. Appl. No. 12/288,031, Advisory Action dated Apr. 12, 2013", 3 pgs.
"U.S. Appl. No. 12/288,031, Final Office Action dated Jan. 3, 2012", 9 pgs.
"U.S. Appl. No. 12/288,031, Final Office Action dated Mar. 12, 2014", 14 pgs.
"U.S. Appl. No. 12/288,031, Non Final Office Action dated May 10, 2012", 8 pgs.
"U.S. Appl. No. 12/288,031, Non Final Office Action dated Jul. 15, 2013", 9 pgs.
"U.S. Appl. No. 12/288,031, Response filed Mar. 25, 2013 to Final Office Action dated Jan. 3, 2013", 11 pgs.
"U.S. Appl. No. 12/288,031, Response filed Apr. 4, 2012 to Restriction Requirement dated Nov. 4, 2011", 3 pgs.
"U.S. Appl. No. 12/288,031, Response filed Oct. 10, 2012 to Non Final Office Action dated May 10, 2012", 11 pgs.
"U.S. Appl. No. 12/288,031, Response filed Nov. 15, 2013 to Non Final Office Action dated Jul. 15, 2013", 11 pgs.
"U.S. Appl. No. 12/288,031, Restriction Requirement dated Nov. 4, 2011", 9 pgs.
"U.S. Appl. No. 12/288,032, Restriction Requirement dated Nov. 4, 2011", 9 pgs.
"U.S. Appl. No. 12/288,034, Advisory Action dated Feb. 25, 2014", 3 pgs.
"U.S. Appl. No. 12/288,034, Final Office Action dated Nov. 4, 2013", 8 pgs.
"U.S. Appl. No. 12/288,034, Non Final Office Action dated Jun. 22, 2012", 7 pgs.
"U.S. Appl. No. 12/288,034, Response filed Feb. 4, 2014 to Final Office Action dated Nov. 4, 2013", 12 pgs.
"U.S. Appl. No. 12/288,034, Response filed May 1, 2012 to Restriction Requirement dated Nov. 3, 2011", 4 pgs.
"U.S. Appl. No. 12/288,034, Response filed Dec. 21, 2012 to Non Final Office Action dated Jun. 22, 2012", 12 pgs.
"U.S. Appl. No. 12/288,034, Restriction Requirement dated Nov. 3, 2011", 9 pgs.
"U.S. Appl. No. 12/288,045, Restriction Requirement dated Nov. 16, 2011", 9 pgs.
"U.S. Appl. No. 12/315,015, Advisory Action dated Apr. 7, 2014", 3 pgs.
"U.S. Appl. No. 12/315,015, Advisory Action dated Sep. 12, 2012", 3 pgs.
"U.S. Appl. No. 12/315,015, Final Office Action dated Jan. 28, 2014", 8 pgs.
"U.S. Appl. No. 12/315,015, Final Office Action dated Apr. 26, 2012", 7 pgs.
"U.S. Appl. No. 12/315,015, Non Final Office Action dated Sep. 27, 2013", 7 pgs.
"U.S. Appl. No. 12/315,015, Non Final Office Action dated Oct. 6, 2011", 11 pgs.
"U.S. Appl. No. 12/315,015, Preliminary Amendment filed Mar. 10, 2009", 3 pgs.
"U.S. Appl. No. 12/315,015, Response filed Mar. 28, 2014 to Final Office Action dated Jan. 24, 2014", 5 pgs.
"U.S. Appl. No. 12/315,015, Response filed Apr. 6, 2012 to Non Final Office Action dated Oct. 6, 2011", 12 pgs.
"U.S. Appl. No. 12/315,015, Response filed Aug. 27, 2012 to Final Office Action dated Apr. 26, 2012", 6 pgs.
"U.S. Appl. No. 12/315,015, Response filed Dec. 27, 2013 to Non Final Office Action dated Sep. 27, 2013", 7 pgs.
"U.S. Appl. No. 12/653,219, Non Final Office Action dated May 30, 2012", 16 pgs.
"U.S. Appl. No. 12/917,842, Non Final Office Action dated Nov. 13, 2012", 6 pgs.
"U.S. Appl. No. 12/917,842, Notice of Allowance dated May 20, 2013", 8 pgs.
"U.S. Appl. No. 12/917,842, Notice of Allowance dated Aug. 27, 2013", 6 pgs.
"U.S. Appl. No. 12/917,842, Notice of Allowance dated Dec. 2, 2013", 7 pgs.
"U.S. Appl. No. 12/917,842, Response filed Apr. 15, 2013 to Non Final Office Action dated Nov. 13, 2012", 9 pgs.
"U.S. Appl. No. 12/917,842, Response filed Oct. 15, 2012 to Restriction Requirement dated Sep. 14, 2012", 2 pgs.
"U.S. Appl. No. 12/917,842, Restriction Requirement dated Sep. 14, 2012", 5 pgs.
"U.S. Appl. No. 12/942,232, Non Final Office Action dated Oct. 9, 2013", 13 pgs.
"U.S. Appl. No. 12/942,232, Response filed Jan. 9, 2014 to Non Final Office Action dated Oct. 9, 2013", 11 pgs.
"U.S. Appl. No. 13/157,242, Advisory Action dated Jul. 30, 2013", 3 pgs.
"U.S. Appl. No. 13/157,242, Final Office Action dated May 16, 2013", 7 pgs.
"U.S. Appl. No. 13/157,242, Non Final Office Action dated Jun. 18, 2012", 9 pgs.
"U.S. Appl. No. 13/157,242, Non Final Office Action dated Oct. 31, 2013", 6 pgs.
"U.S. Appl. No. 13/157,242, Notice of Allowance dated Feb. 26, 2014", 8 pgs.
"U.S. Appl. No. 13/157,242, Preliminary Amendment filed Jun. 9, 2011", 7 pgs.
"U.S. Appl. No. 13/157,242, Response filed Jan. 28, 2014 to Non Final Office Action dated Oct. 31, 2013", 11 pgs.
"U.S. Appl. No. 13/157,242, Response filed Jun. 1, 2012 to Restriction Requirement dated May 1, 2012", 3 pgs.
"U.S. Appl. No. 13/157,242, Response filed Jul. 16, 2013 to Final Office Action dated May 16, 2013", 9 pgs.
"U.S. Appl. No. 13/157,242, Response filed Dec. 18, 2012 to Non Final Office Action dated Jun. 18, 2012", 11 pgs.
"U.S. Appl. No. 13/157,242, Restriction Requirement dated May 1, 2012", 6 pgs.
"U.S. Appl. No. 13/162,384, Advisory Action dated Nov. 15, 2013", 3 pgs.
"U.S. Appl. No. 13/162,384, Final Office Action dated Aug. 27, 2013", 14 pgs.
"U.S. Appl. No. 13/162,384, Non Final Office Action dated Mar. 28, 2013", 8 pgs.
"U.S. Appl. No. 13/162,384, Preliminary Amendment filed Jun. 16, 2011", 7 pgs.
"U.S. Appl. No. 13/162,384, Response filed Jun. 27, 2013", 9 pgs.
"U.S. Appl. No. 13/162,384, Response filed Oct. 18, 2013 to Final Office Action dated Aug. 27, 2013", 5 pgs.
"U.S. Appl. No. 13/291,942, Advisory Action dated Mar. 21, 2014", 3 pgs.
"U.S. Appl. No. 13/291,942, Final Office Action dated Jan. 3, 2014", 10 pgs.
"U.S. Appl. No. 13/291,942, Non Final Office Action dated Dec. 20, 2012", 5 pgs.
"U.S. Appl. No. 13/291,942, Preliminary Amendment filed Nov. 8, 2011", 3 pgs.
"U.S. Appl. No. 13/291,942, Response filed Mar. 4, 2014 to Final Office Action dated Jan. 3, 2014", 10 pgs.
"U.S. Appl. No. 13/291,942, Response filed Apr. 17, 2013 to Non-Final Office Action dated Dec. 20, 2012", 8 pgs.
"U.S. Appl. No. 13/495,836, Non Final Office Action dated Aug. 5, 2013", 7 pgs.
"U.S. Appl. No. 13/495,836, Non Final Office Action dated Dec. 26, 2012", 9 pgs.
"U.S. Appl. No. 13/495,836, Notice of Allowance dated Dec. 4, 2013", 9 pgs.
"U.S. Appl. No. 13/495,836, Preliminary Amendment filed Jun. 13, 2012", 8 pgs.
"U.S. Appl. No. 13/495,836, Response filed Mar. 25, 2013 to Non Final Office Action dated Dec. 26, 2012", 9 pgs.
"U.S. Appl. No. 13/495,836, Response filed Nov. 5, 2013 to Non Final Office Action dated Aug. 5, 2013", 8 pgs.
"Australian Application Serial No. 2002351188, Office Action dated Mar. 30, 2007", 1 pg.
"Australian Application Serial No. 2002351188, Office Action dated Dec. 8, 2008", 3 pgs.

(56) References Cited

OTHER PUBLICATIONS

"Australian Application Serial No. 2002353807, First Examiner Report dated Nov. 16, 2006", 2 pgs.
"Australian Application Serial No. 2004277897, First Examiner Report dated Oct. 14, 2009", 2 pgs.
"Australian Application Serial No. 2004277897, Response filed Jul. 14, 2011 to First Examiner Report dated Oct. 14, 2009", 9 pgs.
"Australian Application Serial No. 2004287354, Office Action dated Oct. 13, 2009", 2 pgs.
"Australian Application Serial No. 2004287355, Office Action dated May 11, 2009", 2 pgs.
"Australian Application Serial No. 2005204615, Office Action dated Jan. 20, 2010", 4 pgs.
"Australian Application Serial No. 2005235108, Office Action dated Feb. 26, 2010", 3 pgs.
"Australian Application Serial No. 2006302908, Office Action dated Mar. 4, 2011", 8 pgs.
"Australian Application Serial No. 2006305688, First Examiner Report dated Mar. 10, 2011", 3 pgs.
"Australian Application Serial No. 2006305688, Response filed Oct. 22, 2012 to First Examiner Report dated Mar. 10, 2011", 16 pgs.
"Australian Application Serial No. 2006305689, Office Action dated Sep. 5, 2011", 3 pgs.
"Australian Application Serial No. 2006309241, Office Action dated Mar. 4, 2011", 6 pgs.
"Australian Application Serial No. 2008243229, First Examiner Report dated Apr. 13, 2010", 2 pgs.
"Australian Application Serial No. 2008243229, Response filed May 13, 2011 to Office Action dated Apr. 13, 2010", 15 pgs.
"Australian Application Serial No. 2011224089, First Examiners Report dated Mar. 27, 2013", 3 pgs.
"Australian Application Serial No. 2011253682, Office Action dated Sep. 27, 2012", 4 pgs.
"Australian Application Serial No. 2011253682, Response filed Jul. 17, 2013 to Office Action dated Sep. 27, 2012", 19 pgs.
"Canadian Application Serial No. 2,464,900, Office Action dated Sep. 29, 2009", 3 pgs.
"Canadian Application Serial No. 2,539,585, Office Action dated Aug. 31, 2010", 2 pgs.
"Canadian Application Serial No. 2,539,585, Office Action dated Sep. 19, 2012", 2 pgs.
"Canadian Application Serial No. 2,546,681, Office Action dated Feb. 25, 2011", 3 pgs.
"Canadian Application Serial No. 2,546,721, Office Action dated Feb. 25, 2011", 3 pgs.
"Canadian Application Serial No. 2,551,685, Office Action dated Jan. 17, 2011", 3 pgs.
"Canadian Application Serial No. 2,554,022, Office Action dated Jun. 22, 2011", 3 pgs.
"Canadian Application Serial No. 2,554,022, Office Action dated Aug. 31, 2010", 2 pgs.
"Canadian Application Serial No. 2,558,317, Office Action dated Aug. 31, 2010", 2 pgs.
"Canadian Application Serial No. 2,558,317, Office Action dated Sep. 28, 2011", 3 pgs.
"Canadian Application Serial No. 2,626,403, Office Action dated Apr. 2, 2013", 3 pgs.
"Canadian Application Serial No. 2,626,403, Response filed Feb. 12, 2014 to Office Action dated Apr. 2, 2013", 20 pgs.
"Chinese Application Serial No. 02823581.9, Office Action dated Mar. 1, 2006", 7 pgs.
"Chinese Application Serial No. 02823581.9, Office Action dated Apr. 18, 2008", (W/ English Translation), 6 pgs.
"Chinese Application Serial No. 02823581.9, Office Action dated Aug. 8, 2007", 4 pgs.
"Chinese Application Serial No. 02823581.9, Office Action dated Nov. 17, 2006", 7 pgs.
"Chinese Application Serial No. 02823581.9, Response filed Jan. 31, 2007 to Office Action dated Nov. 17, 2006", 8 pgs.
"Chinese Application Serial No. 02823581.9, Response filed Apr. 7, 2006 to Office Action dated Mar. 1, 2006", 4 pgs.
"Chinese Application Serial No. 02823581.9, Response filed May 19, 2008 to Office Action dated Apr. 18, 2008", (W/ English Translation), 38 pgs.
"Chinese Application Serial No. 02823581.9, Response filed Dec. 3, 2007 to Office Action dated Aug. 8, 2007", 6 pgs.
"Chinese Application Serial No. 200480027649.7, Office Action dated Jun. 23, 2008", w/English translation, 5 pgs.
"Chinese Application Serial No. 200480027649.7, Office Action dated Sep. 4, 2009", w/English translation, 18 pgs.
"Chinese Application Serial No. 200480027649.7, Office Action dated Dec. 24, 2010", w/English translation, 6 pgs.
"Chinese Application Serial No. 200480027649.7, Response filed Jan. 19, 2010 to Office Action dated Sep. 4, 2009", 5 pgs.
"Chinese Application Serial No. 200480027649.7, Response filed Mar. 8, 2011 to Office Action dated Dec. 24, 2010", w/English translation, 7 pgs.
"Chinese Application Serial No. 200480031226.2, Office Action dated Jan. 23, 2009", w/English translation, 9 pgs.
"Chinese Application Serial No. 200480031226.2, Office Action dated Apr. 27, 2010", (W/ English Translation), 7 pgs.
"Chinese Application Serial No. 200480031226.2, Office Action dated Dec. 21, 2010", (W/ English Translation), 10 pgs.
"Chinese Application Serial No. 200480031226.2, Response filed Feb. 25, 2011 to Office Action dated Dec. 21, 2010", (W/ English Translation), 18 pgs.
"Chinese Application Serial No. 200480031226.2, Response filed May 22, 2009 to Office Action dated Jan. 23, 2009", 5 pgs.
"Chinese Application Serial No. 200480031226.2, Response filed Jul. 12, 2010 to Office Action dated Apr. 27, 2010", 5 pgs.
"Chinese Application Serial No. 200580002026.9, Office Action dated Jun. 19, 2009", (W/ English Translation), 12 pgs.
"Chinese Application Serial No. 200580002026.9, Response filed Jan. 4, 2010 to Office Action dated Jun. 19, 2009", 10 pgs.
"Chinese Application Serial No. 200580006169.7, Office Action dated Mar. 1, 2010", w/English translation, 12 pgs.
"Chinese Application Serial No. 200580006169.7, Response filed Jul. 14, 2010 to Office Action dated Mar. 1, 2010", w/English translation, 32 pgs.
"Chinese Application Serial No. 200580009570.6, Office Action dated May 9, 2008", (W/ English Translation), 2 pgs.
"Chinese Application Serial No. 200580009570.6, Response filed Nov. 21, 2008 to Office Action dated May 9, 2008", 7 pgs.
"Chinese Application Serial No. 200680034052.4, Office Action dated May 11, 2010", w/English translation, 7 pgs.
"Chinese Application Serial No. 200680034052.4, Office Action dated Aug. 14, 2009", w/English translation, 13 pgs.
"Chinese Application Serial No. 200680034052.4, Response filed Mar. 1, 2010 to Office Action dated Aug. 14, 2009", 4 pgs.
"Chinese Application Serial No. 200680034052.4, Response filed Sep. 26, 2010 to Office Action dated May 11, 2010", 5 pgs.
"Chinese Application Serial No. 200680038882.4, Office Action dated May 11, 2010", (W/ English Translation), 18 pgs.
"Chinese Application Serial No. 200680046854.7, Office Action dated Apr. 14, 2010", (W/ English Translation), 18 pgs.
"Chinese Application Serial No. 200680046854.7, Response filed Sep. 26, 2010 to Office Action dated Apr. 14, 2010", 10 pgs.
"Chinese Application Serial No. 200680047552.1, Office Action dated Jun. 4, 2010", (W/ English Translation), 7 pgs.
"Chinese Application Serial No. 200680047552.1, Response filed Dec. 20, 2010 to Office Action dated Jun. 4, 2010", 10 pgs.
"Chinese Application Serial No. 200810210922.X, Office Action dated Jan. 19, 2012", (W/ English Translation), 6 pgs.
"Chinese Application Serial No. 200810210922.X, Office Action dated Apr. 2, 2010", (W/ English Translation), 4 pgs.
"Chinese Application Serial No. 200810210922.X, Office Action dated Aug. 23, 2011", 6 pgs.
"Chinese Application Serial No. 200810210922.X, Response filed Jun. 1, 2012 to Office Action dated Jan. 19, 2012", 5 pgs.
"Chinese Application Serial No. 200810210922.X, Response filed Aug. 12, 2010 to Office Action dated Apr. 2, 2010", 10 pgs.

(56) References Cited

OTHER PUBLICATIONS

"Chinese Application Serial No. 200910139527.1, Office Action dated Jul. 12, 2010", w/English translation, 9 pgs.
"Chinese Application Serial No. 200910139527.1, Response filed Nov. 28, 2011 to Office Action dated Jul. 12, 2010", 9 pgs.
"European Application Serial No. 02789196.9, European Search Report dated Aug. 14, 2009", 5 pgs.
"European Application Serial No. 02789196.9, Office Action dated Feb. 6, 2012", 4 pgs.
"European Application Serial No. 02789196.9, Office Action dated Mar. 7, 2012", 3 pgs.
"European Application Serial No. 02789196.9, Office Action dated Apr. 19, 2010", 4 pgs.
"European Application Serial No. 02789196.9, Office Action dated Jul. 14, 2011", 3 pgs.
"European Application Serial No. 02789196.9, Response filed Jan. 18, 2012 to Office Action dated Jul. 14, 2011", 19 pgs.
"European Application Serial No. 02789196.9, Response filed Feb. 16, 2012 to Office Action dated Feb. 6, 2012", 9 pgs.
"European Application Serial No. 02789196.9, Response filed Apr. 5, 2012 to Office Action dated Mar. 7, 2012", 5 pgs.
"European Application Serial No. 02789196.9, Response filed Oct. 25, 2010 to Office Action dated Apr. 19, 2010", 16 pgs.
"European Application Serial No. 04788653.6, Office Action dated May 19, 2006", 2 pgs.
"European Application Serial No. 05704902.5, European Search Report dated Aug. 29, 2011", 3 pgs.
"European Application Serial No. 05713941.2, Office Action dated Dec. 13, 2007", 2 pgs.
"European Application Serial No. 06802573.3, Extended European Search Report dated Feb. 15, 2012", 6 pgs.
"European Application Serial No. 06802573.3, Office Action dated Mar. 5, 2012", 1 pg.
"European Application Serial No. 06802573.3, Office Action dated May 28, 2008", 2 pgs.
"European Application Serial No. 06802573.3, Response filed Sep. 3, 2012 to Office Action dated Mar. 5, 2012", 15 pgs.
"European Application Serial No. 06802578.2, European Search Report dated Mar. 7, 2013", 10 pgs.
"European Application Serial No. 06802580.8, Extended European Search Report dated Sep. 24, 2013", 8 pgs.
"European Application Serial No. 06802580.8, Office Action dated Feb. 25, 2013", 3 pgs.
"European Application Serial No. 09075319.5, Extended European Search Report dated Oct. 14, 2009", 6 pgs.
"European Application Serial No. 09075319.5, Office Action dated Jan. 14, 2010", 1 pgs.
"European Application Serial No. 09075319.5, Office Action dated Oct. 14, 2010", 4 pgs.
"European Application Serial No. 09820886.1, Office Action dated Jun. 7, 2011", 2 pgs.
"European Application Serial No. 09820886.1, Response filed Dec. 8, 2011 to Office Action dated Jun. 7, 2011", 3 pgs.
"European Application Serial No. 09820891.1, Office Action dated Jun. 7, 2011", 2 pgs.
"European Application Serial No. 09820891.1, Response filed Dec. 8, 2011 to Office Action dated Jun. 7, 2011", 2 pgs.
"European Application Serial No. 09075319.5, Response filed Feb. 21, 2011 to Office Action dated Oct. 14, 2010", 5 pgs.
"European Application Serial No. 09075319.5, Response filed Jul. 20, 2010 to Office Action dated Jan. 14, 2010", 13 pgs.
"German Application Serial No. 10297483.7, Office Action dated Jan. 9, 2006", 4 pgs.
"German Application Serial No. 10297483.7, Office Action dated Jul. 8, 2006", 2 pgs.
"German Application Serial No. 10297483.7, Office Action dated and Response filed Oct. 30, 2006", 8 pgs.
"German Application Serial No. 10297483.7, Response filed Jul. 7, 2006 to Office Action dated Jan. 9, 2006", 14 pgs.
"German Application Serial No. 10297483.7, Response filed Oct. 26, 2006 to Office Action dated Jul. 8, 2006", 3 pgs.
"Great Britain Application Serial No. 0411107.6, Office Action dated Feb. 28, 2005", 3 pgs.
"Great Britain Application Serial No. 0411107.6, Office Action dated Sep. 29, 2005", 1 pg.
"Great Britain Application Serial No. 0411107.6, Response filed Aug. 23, 2005 to Office Action dated Feb. 28, 2005", 3 pgs.
"Great Britain Application Serial No. 0411107.6, Response filed Oct. 31, 2005 to Office Action dated Sep. 29, 2005", 4 pgs.
"Great Britain Application Serial No. 0522152.8, Office Action dated Dec. 5, 2005", 5 pgs.
"Great Britain Application Serial No. 0522152.8, Response filed Apr. 26, 2006 to Office Action dated Dec. 5, 2005", 48 pgs.
"International Application Serial No. PCT/US2002/032753, International Preliminary Examination Report dated Aug. 16, 2004", 3 pgs.
"International Application Serial No. PCT/US2002/032753, International Search Report dated Mar. 6, 2003", 1 pg.
"International Application Serial No. PCT/US2002/032753, Written Opinion dated Aug. 26, 2003", 4 pgs.
"International Application Serial No. PCT/US2002/038365, International Preliminary Report on Patentability dated Feb. 6, 2004", 3 pgs.
"International Application Serial No. PCT/US2002/038365, International Search Report dated May 8, 2003", 3 pgs.
"International Application Serial No. PCT/US2002/038365, Written Opinion dated Oct. 27, 2003", 4 pgs.
"International Application Serial No. PCT/US2004/027587, International Preliminary Report on Patentability dated May 24, 2006", 3 pgs.
"International Application Serial No. PCT/US2004/027587, International Search Report dated Dec. 27, 2005", 1 pg.
"International Application Serial No. PCT/US2004/027587, Written Opinion dated Dec. 27, 2005", 3 pgs.
"International Application Serial No. PCT/US2004/027589, International Preliminary Report on Patentability dated Apr. 6, 2005", 4 pgs.
"International Application Serial No. PCT/US2004/027589, International Search Report dated Apr. 6, 2005", 1 pg.
"International Application Serial No. PCT/US2004/027589, Written Opinion dated Apr. 6, 2005", 3 pgs.
"International Application Serial No. PCT/US2004/027590, International Preliminary Examination Report dated Feb. 16, 2006", 3 pgs.
"International Application Serial No. PCT/US2004/027590, International Search Report dated Jan. 12, 2005", 1 pg.
"International Application Serial No. PCT/US2004/027590, Written Opinion dated Jan. 12, 2005", 3 pgs.
"International Application Serial No. PCT/US2004/029402, International Preliminary Report on Patentability dated Jul. 10, 2006", 3 pgs.
"International Application Serial No. PCT/US2004/029402, International Search Report dated Feb. 24, 2006", 1 pg.
"International Application Serial No. PCT/US2004/029402, Written Opinion dated Feb. 24, 2006", 3 pgs.
"International Application Serial No. PCT/US2005/000059, International Preliminary Report on Patentability dated May 18, 2007", 8 pgs.
"International Application Serial No. PCT/US2005/000059, International Search Report dated Jan. 5, 2007", 3 pgs.
"International Application Serial No. PCT/US2005/000059, Written Opinion dated Jan. 5, 2007", 8 pgs.
"International Application Serial No. PCT/US2005/005453, International Preliminary Examination Report dated Mar. 13, 2006", 3 pgs.
"International Application Serial No. PCT/US2005/005453, International Preliminary Report on Patentability dated Feb. 16, 2006", 3 pgs.
"International Application Serial No. PCT/US2005/005453, International Search Report dated Aug. 30, 2005", 1 pg.
"International Application Serial No. PCT/US2005/005453, Written Opinion dated Aug. 30, 2005", 3 pgs.

(56) References Cited

OTHER PUBLICATIONS

"International Application Serial No. PCT/US2005/005627, International Preliminary Examination Report dated Apr. 7, 2009", 3 pgs.
"International Application Serial No. PCT/US2005/005627, International Search Report dated Sep. 25, 2007", 1 pg.
"International Application Serial No. PCT/US2005/005627, Written Opinion dated Sep. 25, 2007", 3 pgs.
"International Application Serial No. PCT/US2006/033741, International Preliminary Report on Patentability dated Jul. 28, 2007", 5 pgs.
"International Application Serial No. PCT/US2006/033741, International Search Report dated Mar. 30, 2007", 1 pg.
"International Application Serial No. PCT/US2006/033741, Written Opinion dated Mar. 30, 2007", 4 pgs.
"International Application Serial No. PCT/US2006/033747, International Preliminary Report on Patentability dated Mar. 1, 2011", 4 pgs.
"International Application Serial No. PCT/US2006/033747, International Search Report dated Jul. 8, 2008", 1 pg.
"International Application Serial No. PCT/US2006/033747, Written Opinion dated Jul. 8, 2008", 3 pgs.
"International Application Serial No. PCT/US2006/033748, International Preliminary Report on Patentability dated Jun. 18, 2008", 7 pgs.
"International Application Serial No. PCT/US2006/033748, International Search Report dated Aug. 15, 2007", 1 pg.
"International Application Serial No. PCT/US2006/033748, Written Opinion dated Aug. 15, 2007", 5 pgs.
"International Application Serial No. PCT/US2006/033749, International Preliminary Report on Patentability dated Jun. 18, 2008", 6 pgs.
"International Application Serial No. PCT/US2006/033749, International Search Report dated Aug. 15, 2007", 1 pg.
"International Application Serial No. PCT/US2006/033749, Written Opinion dated Aug. 15, 2007", 5 pgs.
"International Application Serial No. PCT/US2006/037085, International Preliminary Report on Patentability dated Jul. 24, 2008", 9 pgs.
"International Application Serial No. PCT/US2006/037085, International Search Report dated Aug. 30, 2007", 1 pg.
"International Application Serial No. PCT/US2006/037085, Written Opinion dated Aug. 30, 2007", 7 pgs.
"International Application Serial No. PCT/US2009/005604, International Preliminary Report on Patentability dated Jan. 13, 2011", 10 pgs.
"International Application Serial No. PCT/US2009/005604, International Search Report dated Dec. 11, 2009", 2 pgs.
"International Application Serial No. PCT/US2009/005604, Written Opinion dated Dec. 11, 2009", 7 pgs.
"International Application Serial No. PCT/US2009/005607, International Preliminary Report on Patentability dated Jan. 9, 2011", 9 pgs.
"International Application Serial No. PCT/US2009/005607, International Search Report dated Dec. 11, 2009", 2 pgs.
"International Application Serial No. PCT/US2009/005607, Written Opinion dated Dec. 11, 2009", 6 pgs.
"International Application Serial No. PCT/US2009/005608, International Preliminary Report on Patentability dated Jan. 14, 2011", 7 pgs.
"International Application Serial No. PCT/US2009/005608, International Search Report dated Dec. 10, 2009", 2 pgs.
"International Application Serial No. PCT/US2009/005608, Written Opinion dated Dec. 10, 2009", 4 pgs.
"International Application Serial No. PCT/US2009/005609, International Preliminary Report on Patentability dated Jan. 9, 2011", 9 pgs.
"International Application Serial No. PCT/US2009/005609, International Search Report dated Dec. 18, 2009", 2 pgs.
"International Application Serial No. PCT/US2009/005609, Written Opinion dated Dec. 18, 2009", 6 pgs.
"Japanese Application Serial No. 2003-546789, Office Action dated Feb. 26, 2009", w/English translation, 7 pgs.
"Japanese Application Serial No. 2003-546789, Office Action dated Jun. 17, 2008", w/English translation, 6 pgs.
"Japanese Application Serial No. 2003-546789, Office Action dated Oct. 7, 2009", 3 pgs.
"Japanese Application Serial No. 2003-546789, Response filed May 21, 2009 to Office Action dated Feb. 26, 2009", 6 pgs.
"Japanese Application Serial No. 2003-546789, Response filed Dec. 11, 2008 to Office Action dated Jun. 17, 2008", w/English translation, 9 pgs.
"Japanese Application Serial No. 2006-528036, Office Action dated Jan. 19, 2010", 3 pgs.
"Japanese Application Serial No. 2006-528036, Office Action dated Feb. 26, 2009", w/English translation, 5 pgs.
"Japanese Application Serial No. 2006-528036, Office Action dated Jun. 23, 2008", w/English translation, 5 pgs.
"Japanese Application Serial No. 2006-528036, Response filed Dec. 25, 2008 to Office Action dated Jun. 23, 2008", w/English translation, 9 pgs.
"Japanese Application Serial No. 2006-536616, Office Action dated Jun. 23, 2008", (W/ English Translation), 8 pgs.
"Japanese Application Serial No. 2006-536616, Response filed Dec. 19, 2008 to Office Action dated Jun. 23, 2008", (W/ English Translation), 9 pgs.
"Japanese Application Serial No. 2006-536617, Office Action dated Jun. 17, 2008", (W/ English Translation), 3 pgs.
"Japanese Application Serial No. 2006-536617, Response filed May 12, 2009 to Office Action dated Jun. 17, 2008", (W/ English Translation), 19 pgs.
"Japanese Application Serial No. 2006-547608, Office Action dated Jun. 23, 2008", (W/ English Translation), 5 pgs.
"Japanese Application Serial No. 2006-547608, Respone filed Dec. 19, 2008 to Office Action dated Jun. 23, 2008", (W/ English Translation), 10 pgs.
"Japanese Application Serial No. 2007500928, Office Action dated Jul. 1, 2010", w/English translation, 10 pgs.
"Japanese Application Serial No. 2007504965, Office Action dated Mar. 7, 2012", w/English translation, 4 pgs.
"Japanese Application Serial No. 2007504965, Office Action dated Jun. 14, 2011", w/English translation, 4 pgs.
"Japanese Application Serial No. 2007504965, Office Action dated Sep. 14, 2010", English translation, 1 pg.
"Japanese Application Serial No. 2007504965, Response filed Mar. 11, 2011 to Office Action dated Sep. 14, 2010", 8 pgs.
"Japanese Application Serial No. 2008-306790, Office Action dated May 31, 2011", 1 pg.
"Japanese Application Serial No. 2008-306790, Response filed Nov. 29, 2011 to Office Action dated May 8, 2012", 2 pgs.
"Japanese Application Serial No. 2008-306790, Response filed Nov. 29, 2011 to Office Action dated May 31, 2011", (W/ English Translation), 12 pgs.
"Japanese Application Serial No. 2008-316282, Office Action dated May 16, 2011", 2 pgs.
"Japanese Application Serial No. 2008-316296, Office Action dated Feb. 28, 2011", 2 pgs.
"Japanese Application Serial No. 2008-316296, Office Action dated Jun. 22, 2010", 2 pgs.
"Japanese Application Serial No. 2008-323279, Office Action dated Sep. 30, 2010", 1 pg.
"Japanese Application Serial No. 2008-323290, Office Action dated Jun. 6, 2012", (W/ English Translation), 8 pgs.
"Japanese Application Serial No. 2008-323290, Office Action dated Jun. 8, 2011", (W/ English Translation), 8 pgs.
"Japanese Application Serial No. 2008-323290, Response filed Dec. 7, 2011 to Office Action dated Jun. 8, 2011", (W/ English Translation), 16 pgs.
"Japanese Application Serial No. 2008-536574, Office Action dated Mar. 11, 2010", (W/ English Translation), 4 pgs.
"Japanese Application Serial No. 2008-536574, Office Action dated Oct. 3, 2011", (W/ English Translation), 7 pgs.

(56) References Cited

OTHER PUBLICATIONS

"Japanese Application Serial No. 2008-536575, Office Action dated Jul. 7, 2011", (W/ English Translation), 5 pgs.
"Japanese Application Serial No. 2008-536576, Office Action dated Jul. 19, 2011", (W/ English Translation), 4 pgs.
"Japanese Application Serial No. 2008-536577, Notice of Allowance dated May 30, 2012", 3 pgs.
"Japanese Application Serial No. 2008-536577, Office Action dated Jul. 8, 2011", w/English translation, 4 pgs.
"Japanese Application Serial No. 2008-536577, Response filed Jan. 6, 2012 to Office Action dated Jul. 8, 2011", (W/ English Translation), 3 pgs.
"Laparoscopic Surgery", Medical Data International, Inc. MedPro, (1995), 190.
Bolduc, Lee, "Devices, Systems, And Methods For Prosthesis Delivery And Implantation, Including The Use Of A Fastener Tool", .S. Appl. No. 12/917,842, filed Nov. 2, 2010, 120 pgs.
Gadacz, T., et al., "The Spiral Tracker: A New Technique for Stabilizing Prosthetic Mesh in Laparoscopic Hernia Repair", Surgical Rounds, (Nov. 1995), 461-467.
Hatchett, R. L, et al., "Extraperitoneal Endoscopic Burch Repair Using a Tacker Mesh Technique", (1995), 1-4.
Newman, L., et al., "Tacker-Assisted TAPP Procedure", (1995), 2 pgs.

\* cited by examiner

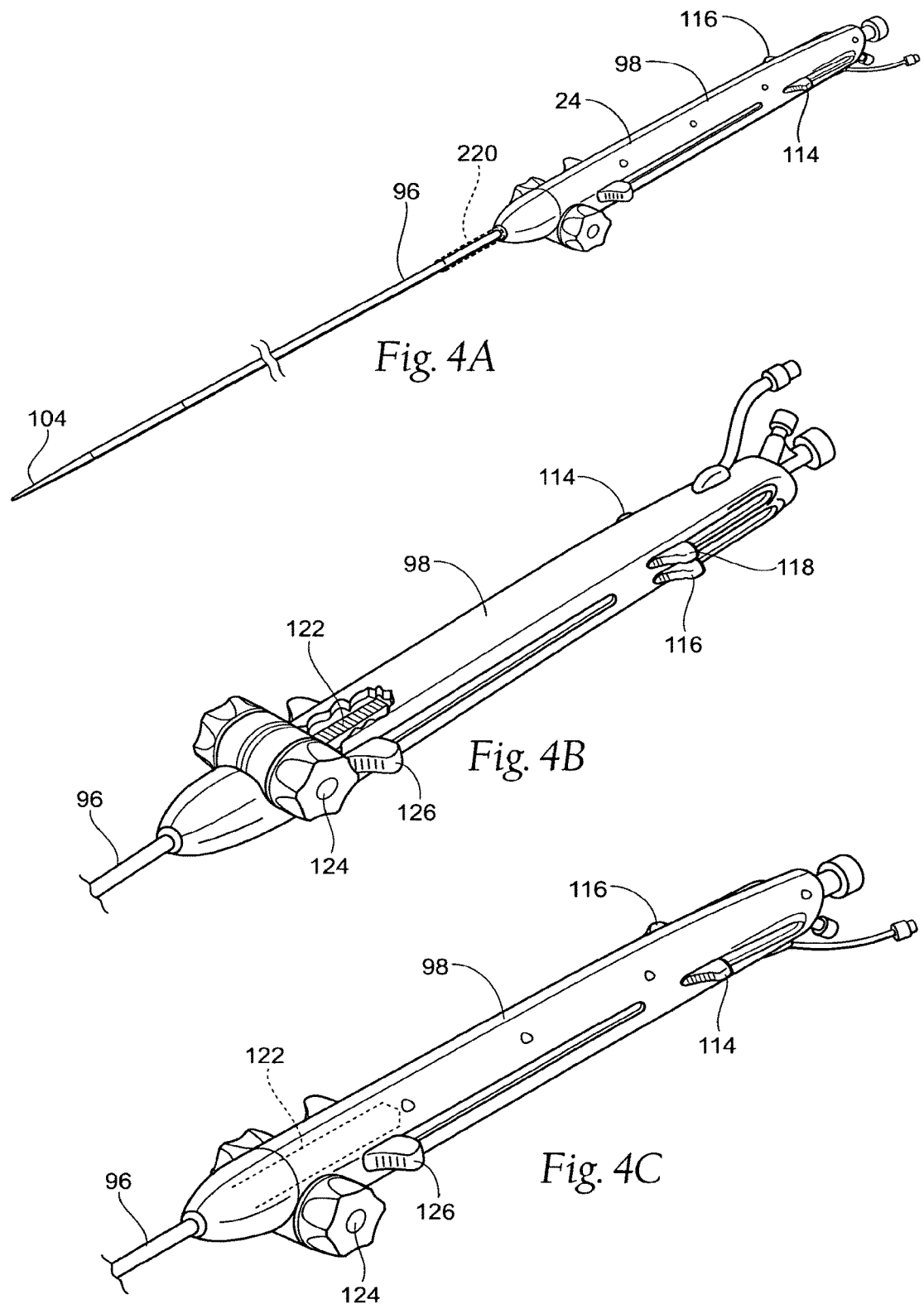

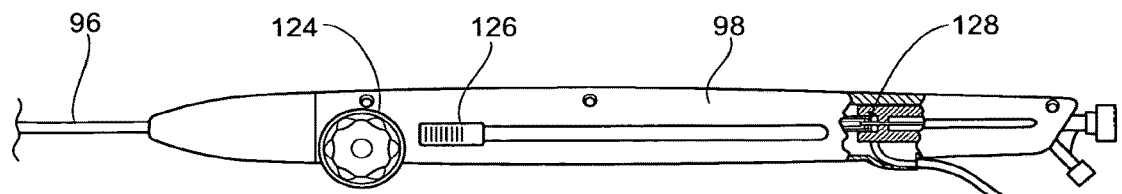
Fig. 5A
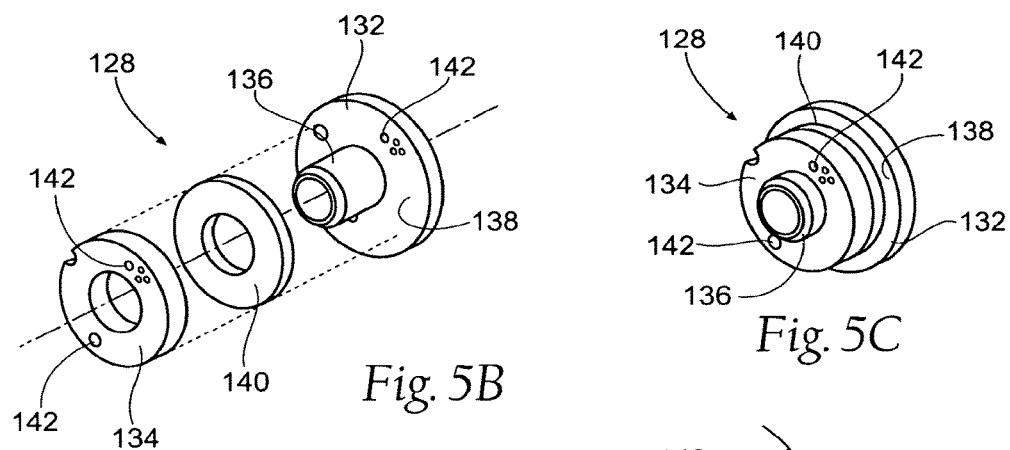
Fig. 5B
Fig. 5C
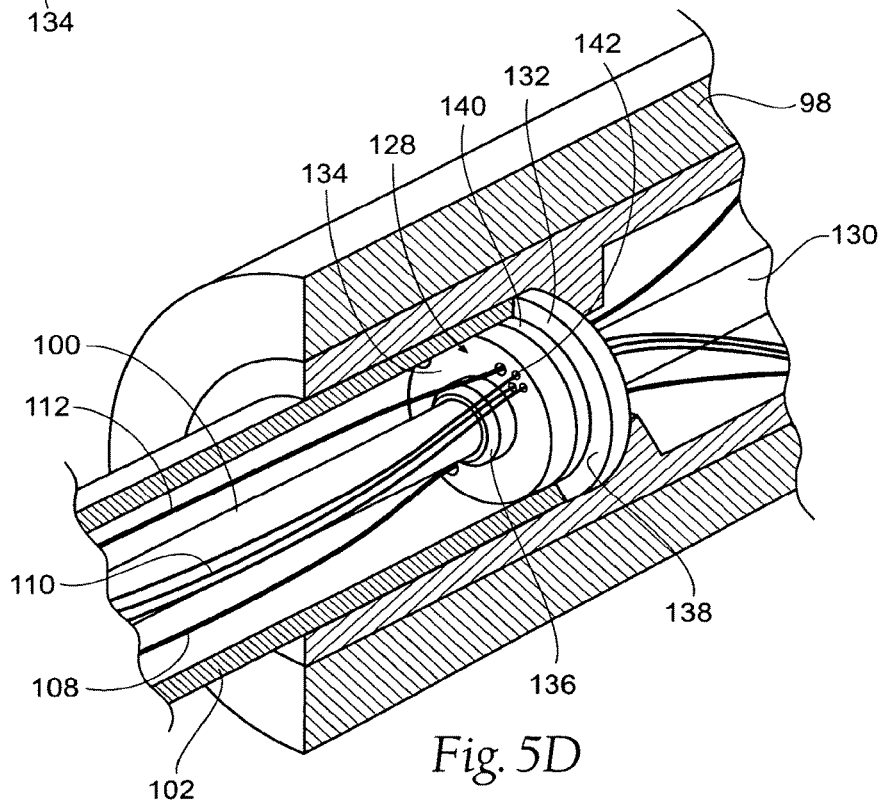
Fig. 5D

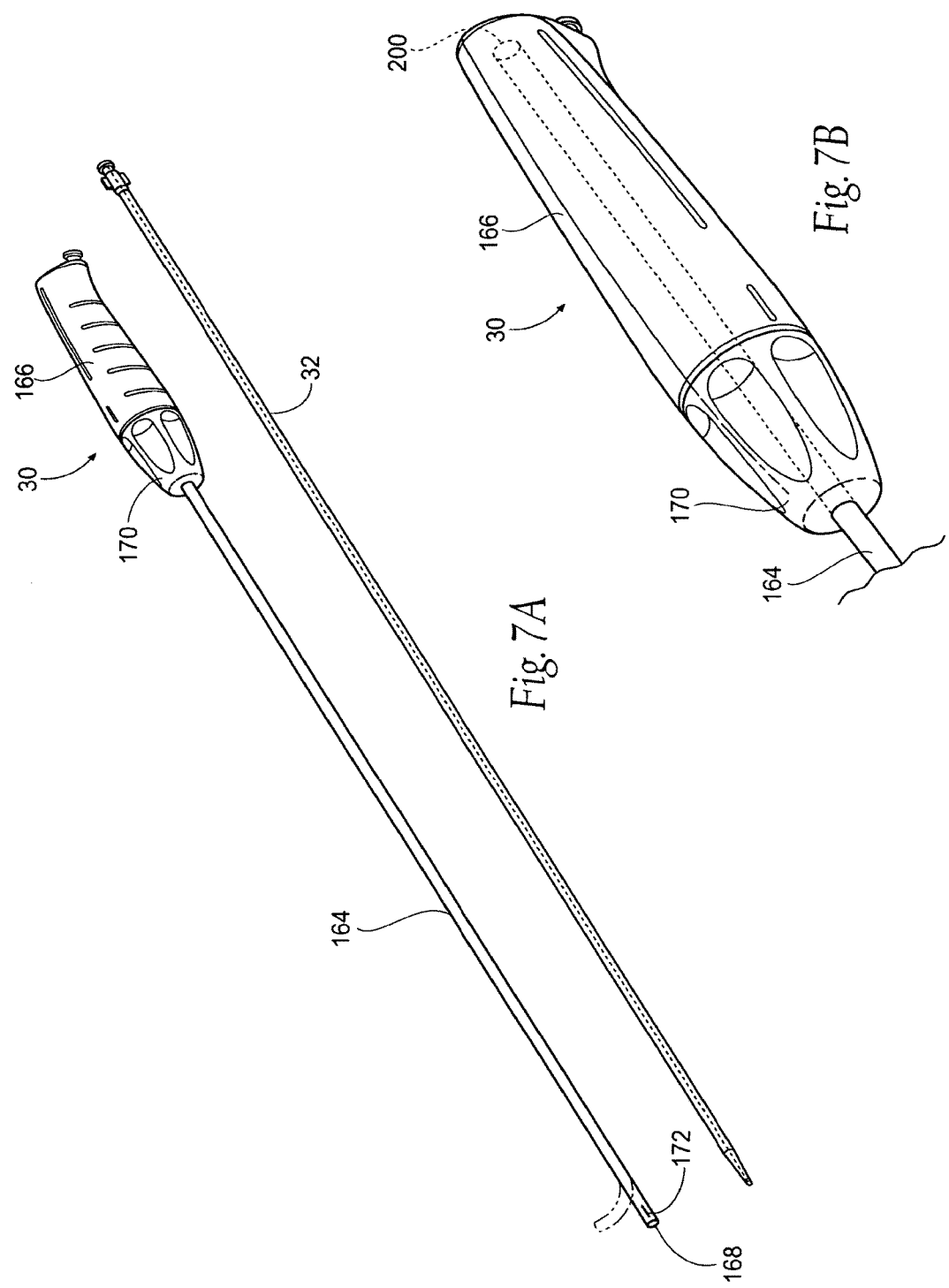

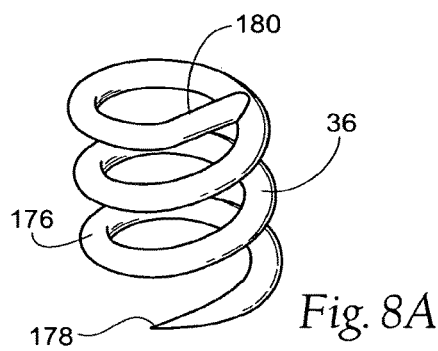
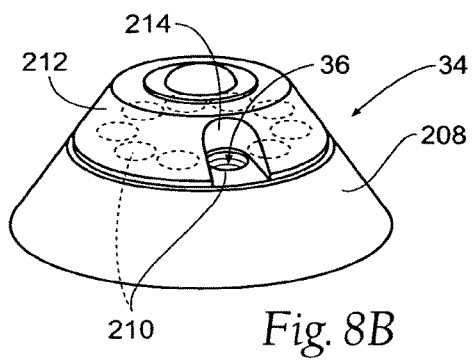
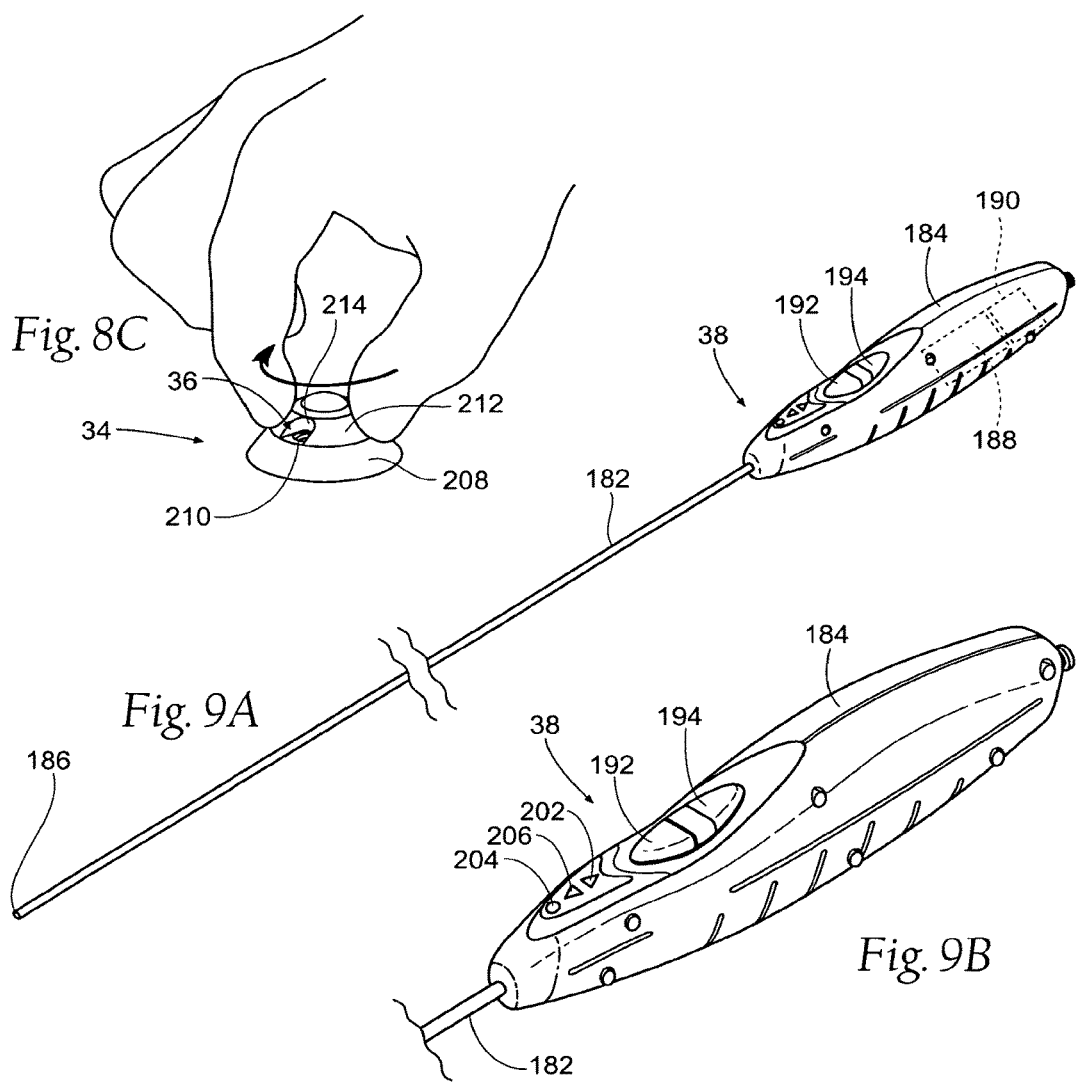

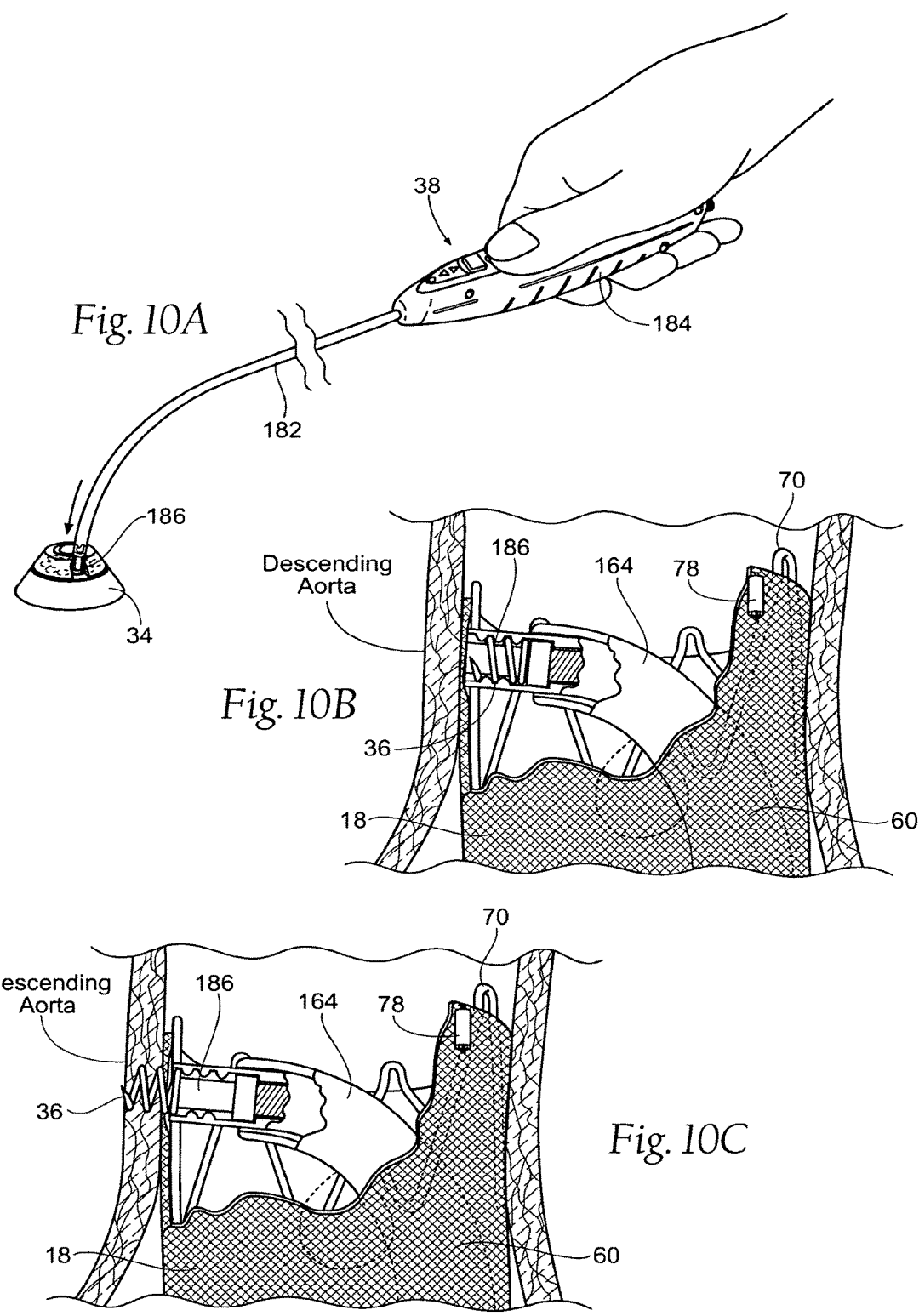

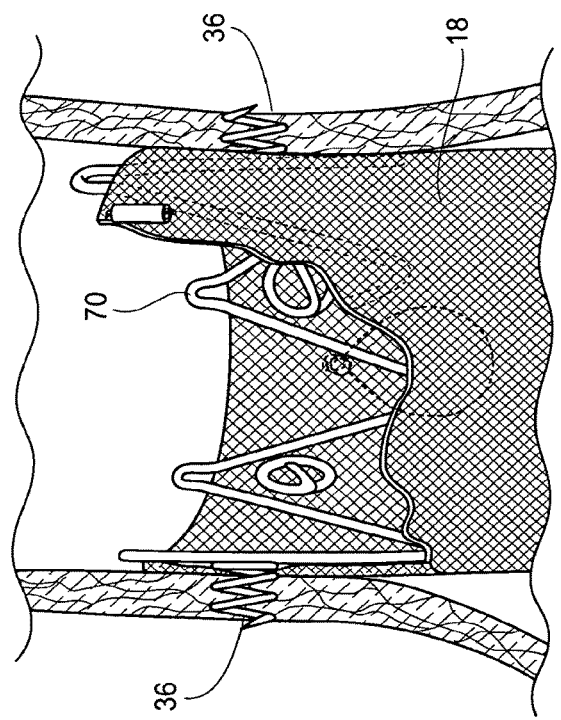
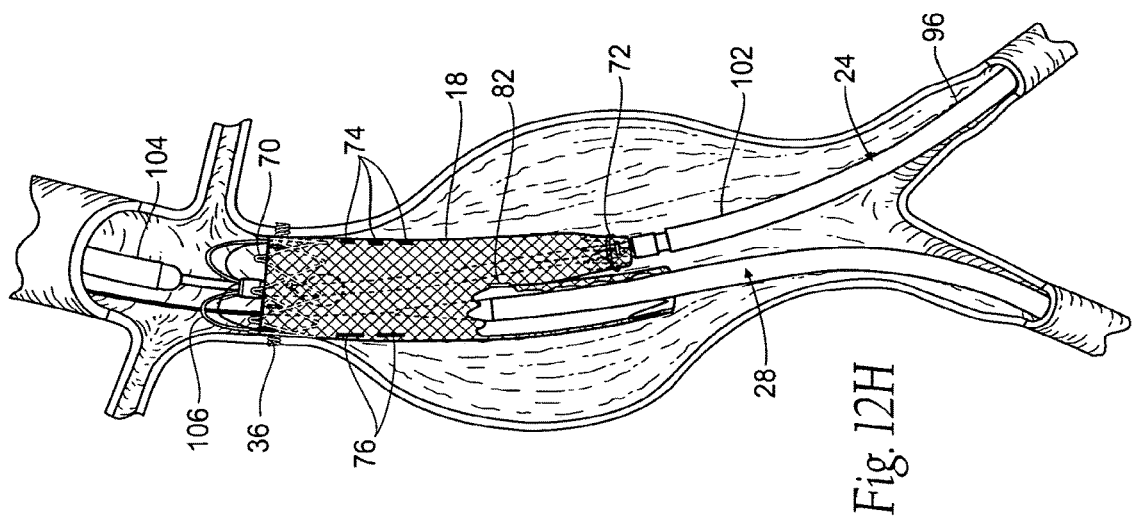
Fig. 12G
Fig. 12H

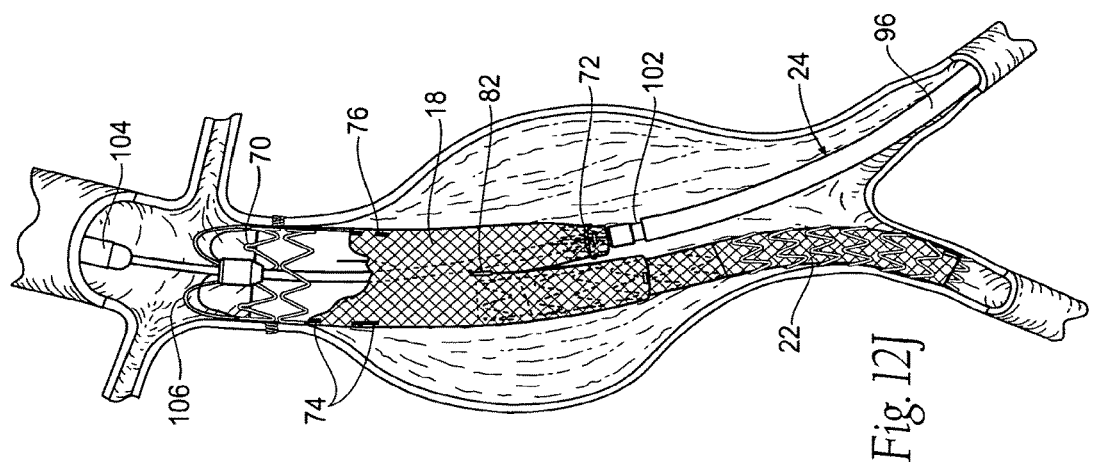
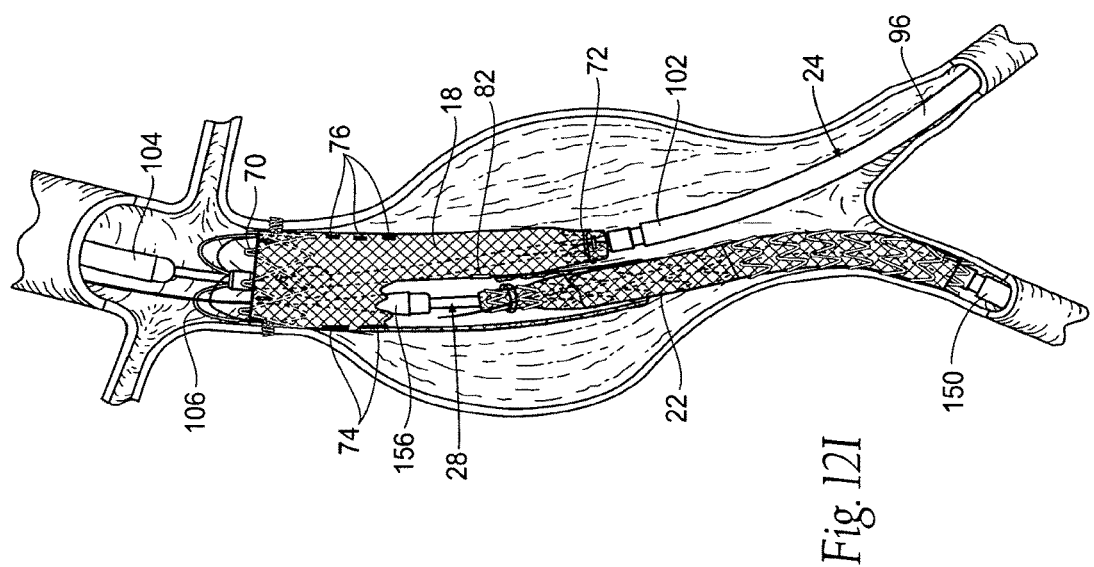

ENDOVASCULAR ANEURYSM DEVICES, SYSTEMS, AND METHODS

RELATED APPLICATIONS

This application is a continuation of U.S. patent application Ser. No. 11/488,305, filed Jul. 18, 2006, (now abandoned), entitled "Endovascular Aneurysm Devices, Systems, and Methods," which is a continuation-in-part of U.S. patent application Ser. No. 11/255,116, filed Oct. 20, 2005, (now U.S. Pat. No. 7,637,932), and entitled "Devices, Systems, and Methods for Prosthesis Delivery and Implantation," which is incorporated herein by reference. This application also is a continuation-in-part of U.S. patent application Ser. No. 10/692,283, filed Oct. 23, 2003, (now U.S. Pat. No. 7,147,657), and entitled "Prosthesis Delivery Systems and Methods," which claims the benefit of U.S. Provisional Patent Application Ser. No. 60/488,753, filed Jul. 21, 2003, and entitled "Endoprosthesis Delivery Systems and Methods." This application also is a continuation-in-part of U.S. patent application Ser. No. 10/786,465, filed Feb. 25, 2004, (now U.S. Pat. No. 8,231,639), and entitled "Systems and Methods for Attaching a Prosthesis Within a Body Lumen or Hollow Organ." This application is also a continuation-in-part of U.S. patent application Ser. No. 11/166,428, filed Jun. 24, 2005, now abandoned, and entitled "Multi-Lumen Prosthesis Systems and Methods," which is a division of U.S. patent application Ser. No. 10/693,255, filed Oct. 24, 2003 (now U.S. Pat. No. 6,929,661), and entitled "Multi-Lumen Prosthesis Systems and Methods," which claims the benefit of U.S. Provisional Patent Application Ser. No. 60/489,011, filed Jul. 21, 2003, and entitled "Bifurcated Prosthesis Systems and Methods." This application also is a continuation-in-part of U.S. patent application Ser. No. 10/307,226, filed Nov. 29, 2002, (now U.S. Pat. No. 8,075,570), and entitled "Intraluminal Prosthesis Attachment Systems and Methods." This application is also a continuation-in-part of U.S. patent application Ser. No. 10/669,881, filed Sep. 24, 2003, (now U.S. Pat. No. 7,491,232), and entitled "Catheter-Based Fastener Implantation Apparatus and Methods with Implantation Force Resolution." This application is also a continuation-in-part of U.S. patent application Ser. No. 11/166,411, filed Jun. 24, 2005, (now U.S. Pat. No. 8,092,519), and entitled "Endovascular Aneurysm Repair System," which is a division of U.S. patent application Ser. No. 10/271,334, filed Oct. 15, 2002 (now U.S. Pat. No. 6,960,217), and entitled "Endovascular Aneurysm Repair System," which claims the benefit of U.S. Provisional Patent Application Ser. No. 60/333,937, filed Nov. 28, 2001, and entitled "Endovascular Aneurysm Repair System." Each of the preceding applications is incorporated herein by reference.

FIELD OF THE INVENTION

The invention relates generally to devices, systems, and methods for the delivery and implantation of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in the abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthesis, made either in a straight or bifurcated configuration, is installed and then permanently attached and sealed to the ends of the native vessel by suture. The prosthesis for these procedures are usually unsupported woven tubes and are typically made from polyester, ePTFE or other suitable materials. The prosthesis are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prostheses for aortic aneurysms are delivered collapsed on a catheter through the femoral artery. These prostheses are usually designed with a fabric material attached to a metallic scaffolding (stent) structure, which expands or is expanded to contact the internal diameter of the vessel. Unlike open surgical aneurysm repair, intraluminally deployed prostheses are not sutured to the native vessel, but rely on either barbs extending from the stent, which penetrate into the native vessel during deployment, or the radial expansion force of the stent itself is utilized to hold the prosthesis in position. These prosthesis attachment means do not provide the same level of attachment when compared to suture and can damage the native vessel upon deployment.

Accordingly, there is a need for improved prosthesis delivery devices, systems, and methods that deliver a prosthetic graft to a body lumen, the prosthesis being able to adapt to changes in aneurysm morphology and able to be deployed safely and without damage to the native vessel.

SUMMARY OF THE INVENTION

One aspect of the invention provides a system comprising a guide defining an access path into a vessel or hollow body organ and a fastener applier comprising a catheter sized and configured for introduction along the access path to a site targeted for implantation of at least one fastener. The guide includes a distal region with terminus. The fastener applier includes an actuated member that is selectively operable to generate an implantation force to implant the at least one fastener within tissue at the site. According to this aspect of the invention, the catheter includes indicia visible to a naked eye to mark when the actuated member rests at a desired distance along the access path short of the terminus of the distal region and is therefore still out of contact with tissue. The visible indicia makes it possible for the physician, without resort to fluoroscopic visualization or other visualizations techniques that augment human sight, to always know whether the fastener is within or outside the guide.

This aspect of the invention also provides instructions for using the guide and fastener applier in which, as the actuated member is being introduced along the access path toward the terminus, the operator or physician is instructed to view the indicia with a naked eye, to detect when the actuated member rests at a desired distance along the access path short of the terminus of the distal region.

Another aspect of the invention provides for a fastener applier an electrically powered drive member coupled to the driven member and a controller coupled to the drive motor. According to this aspect of the invention, the controller includes a LOAD state. In the LOAD state, the controller operates in response to an input command for delivering electrical current to the drive member to drive the driven member in a first direction to load a fastener onto the driven member. The controller senses electrical current delivered to the drive member while loading the fastener onto the driven member. The controller terminates delivery of electrical current to the driven member when a prescribed amount of current is delivered to the drive member, thereby terminating the LOAD state.

On one embodiment, the controller also includes an UNWIND state that follows the LOAD state. In the UNWIND state, which is operative after termination of the LOAD state, the controller delivers electrical current to the drive member to drive the driven member in a second direction. The controller senses a period of operation of the driven member in the second direction which is sufficient to reduce torque windup on the driven member created during the LOAD state. The controller terminates delivery of electrical current to the driven member after the period of operation, thereby terminating the UNWIND state. According to this aspect of the invention, the fastener applier enters a READY TO APPLY state with a minimum of torque windup associated with the driven element.

Another aspect of the invention provides a fluid seal assembly usable in association with, e.g., a catheter assembly including an operative element that, in use, is exposed to a body fluid, a control element, a control filament coupled at one end to the control element and to an opposite end to the operative element. In this arrangement, the seal assembly is positioned between the control element and the operative element, and the control filament passes through the seal assembly to prevent contact between the body fluid and the control element.

According to this aspect of the invention, the seal assembly comprises a first seal component with at least one guide tube formed therein, and a second seal component with at least one guide tube formed therein. The second seal component registers with the first seal component with at least one guide tube in the second component coaxially aligned with at least one guide tube in the first component. A septum is sandwiched between the first and second seal components. The septum accommodates passage of the control filament from one the coaxially aligned guide tubes, through the septum, to the other one of the coaxially aligned guide tubes, thereby providing a fluid seal for the control filament that prevents the control element from contacting body fluid to which the operative element is exposed during use.

Other features and advantages of the invention shall be apparent based upon the accompanying description, drawings, and claims.

BRIEF DESCRIPTION OF THE DRAWINGS

FIG. 4A is a view of the delivery system for the main body of the endovascular graft, which forms a part of the system shown in FIG. 1.

FIGS. 4B and 4C are views of the top and bottom of the control handle of the main body delivery system shown in FIG. 4A.

FIG. 5A is a view of the handle of the main body delivery system shown in FIG. 4A, with portions broken away to show a hemostatic seal assembly within the housing.

FIGS. 5B and 5C are, respectively, exploded and assembled views of the hemostatic seal assembly shown in FIG. 5A.

FIG. 5D is an enlarged view of the hemostatic seal assembly within the handle of the main body delivery system, showing the passage of the release wires through the seal assembly between the control mechanisms and the distal end of the main body delivery system (as shown in FIG. 4D).

FIG. 7A is a view of the steerable endovascular guide and obturator that form a part of the system shown in FIG. 1.

FIG. 7B is an enlarged view of the handle of the steerable endovascular guide shown in FIG. 7A.

FIG. 8A is a view of a endovascular fastener or staple that forms a part of the system shown in FIG. 1.

FIGS. 8B and 8C are views of a cassette to hold the a plurality of endovascular fasteners, as shown in FIG. 8A, and to present the fasteners for loading in the staple applier, which also forms a part of the system shown in FIG. 1.

FIG. 9A is a view of a fastener applier for implanting a fastener as shown in FIG. 8A, which forms a part of the system shown in FIG. 1.

FIG. 9B is an enlarged view of the handle of the fastener applier shown in FIG. 9A.

FIG. 10A is a view showing the manipulation of the fastener applier shown in FIG. 9A in loading a fastener from the cassette shown in FIGS. 8B and 8C.

FIGS. 10B and 10C are anatomic views showing the actuated element at the distal end of the fastener applier being driven to implant a fastener in a graft and adjacent tissue, to secure the position of the graft.

DETAILED DESCRIPTION

This Specification discloses various catheter-based devices, systems, and methods for delivering and implanting radially expandable prostheses in the body lumens. For example, the various aspects of the invention have application in procedures requiring the repair of diseased and/or damaged sections of a hollow body organ and/or blood vessel. The devices, systems, and methods that embody features of the invention are also adaptable for use with systems and surgical techniques that are not necessarily catheter-based.

The devices, systems, and methods are particularly well suited for treating aneurysms of the aorta that primarily occur in the abdominal region, usually in the infrarenal area between the renal arteries and the aortic bifurcation, as well as aneurysms that also occur in the thoracic region between the aortic arch and renal arteries. For this reason, the devices, systems, and methods will be described in this context. Still, it should be appreciated that the disclosed devices, systems, and methods are applicable for use in treating other dysfunctions elsewhere in the body, which are not necessarily aorta-related.

When referring to an endovascular graft or its components that are intended to be implanted in a vessel or body organ, the terms "proximal" and "distal" will be used to describe the relation or orientation of the graft with respect to the heart after implantation. Therefore, the term "proximal" will be used to describe a relation or orientation of the graft that, when implanted, is toward the heart, and the term "distal" will be used to describe a position or orientation of the graft that, when implanted, is away from the heart, i.e., toward the feet.

When referring to implantation apparatus or devices that are manipulated by a physician or operator in order to implant the endovascular graft or its components, the terms "proximal" and "distal" will be used to describe the relation or orientation of the apparatus or device with respect to the operator as it is used. Therefore, the term "proximal" will be used to describe a relation or orientation of the apparatus or device that, when in use, is positioned toward to the operator (i.e., at the handle end of the device), and the term "distal" will be used to describe a position or orientation of the apparatus or device that, when in use, is positioned away from the operator (i.e., at the other end of a catheter or the like away from the handle).

I. System Overview

Figure 1:
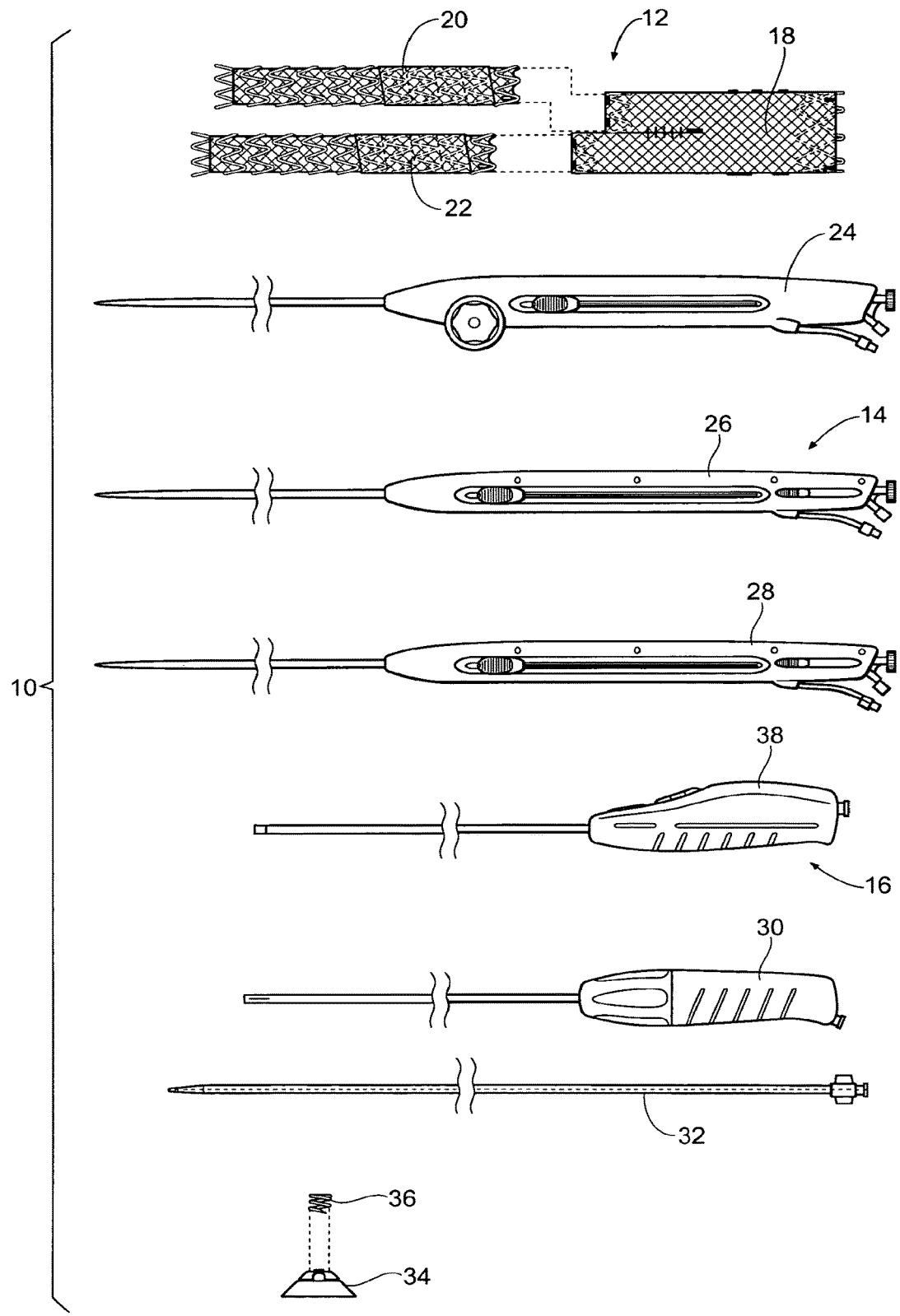
FIG. 1 is a view of the components of a system for repairing an endovascular aneurysm.

FIG. 1 shows a system 10 for repairing an endovascular aneurysm, which is well suited for the repair of an abdominal aortic aneurysm (AAA). The system 10 comprises three primary components 12, 14, and 16.

Figure 3A:
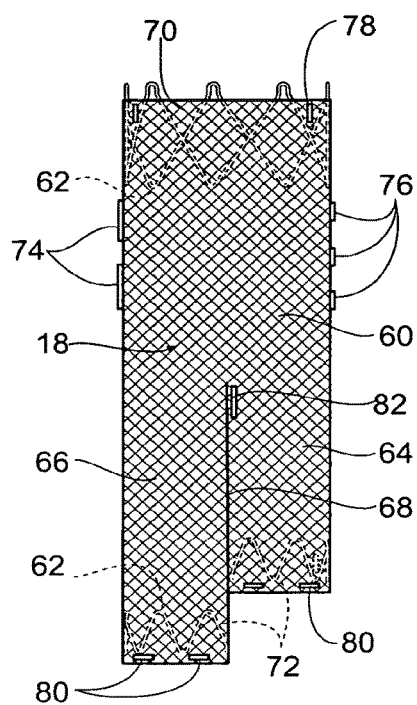
FIG. 3A is a view of the main body of the endovascular graft that forms a part of the system shown in FIG. 1.
Figure 3B:
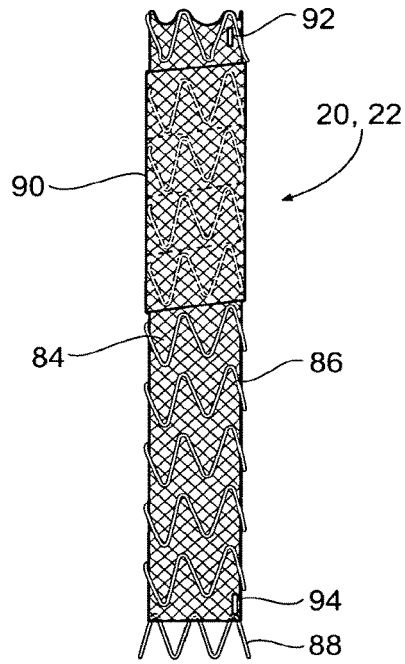
FIG. 3B is a view of a lumen extension of the endovascular graft that forms a part of the system shown in FIG. 1.
Figure 3C:
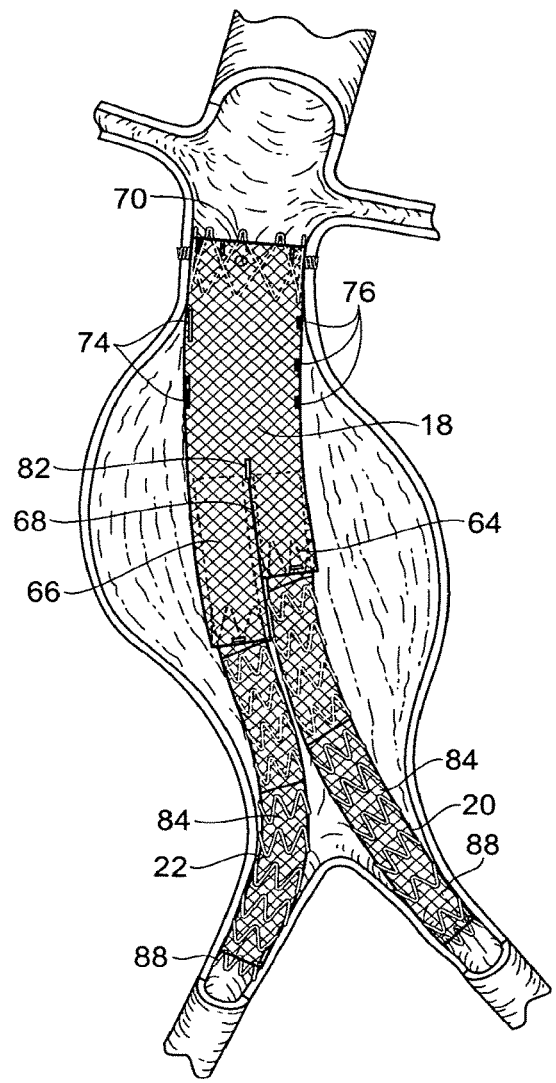
FIG. 3C is an anatomic view of the main body and lumen extensions of the graft assembly assembled within an abdominal aortic aneurysm.

The first component 12 comprises an endovascular graft assembly. In use, the endovascular graft assembly 12 is placed within a vessel at the site of the aneurysm. In the illustrated embodiment, the endovascular graft assembly 12 includes a main body 18 that is placed within the aorta adjacent the renal arteries (see FIG. 3C), and lumen extensions 20 and 22 that extend into the contralateral and ipsilateral branches of the iliac artery, as FIG. 3C shows.

The second component 14 comprises an endovascular delivery system for introducing and deploying in sequence the main body 18 and lumen extensions 20 and 22 of the endovascular graft assembly 12 using an endovascular approach. In the illustrated embodiment, in which the endovascular graft assembly 12 comprises three modular portions—the main body 18, the ipsilateral lumen extension 20, and the contralateral lumen extension 22—there are three corresponding endograft delivery components 24, 26, and 28.

The third component 16 comprises an endovascular stapling system. In use, the endovascular stapling system 16 attaches one or more regions of the endovascular graft assembly to the vessel wall with one or more endovascular staples. In the illustrated embodiment, the endovascular stapling system 16 comprises a steerable endovascular guide 30, an obturator 32, a cassette 34 holding a plurality of endovascular staples 36, and an endovascular staple applier 38. In use, the steerable endovascular guide 30 establishes an endovascular path to the targeted site where the endovascular graft assembly 12 has been partially or fully deployed. The steerable endovascular guide 30 is manipulated by flexure and rotation to successive sites where individual endovascular staples 36 are to be implanted, to penetrate the endovascular graft assembly 12 and adjacent vessel wall. The endovascular staple applier 38, carrying one or more endovascular staples 36, is guided by the steerable endovascular guide 30 to the successive sites. The endovascular staple applier 38 is actuated to implant individual endovascular staples 36 into selected region or regions of the endovascular graft assembly 12 and adjacent vessel wall, to attach the endovascular graft assembly 12 to the vessel wall.

II. The Kit

Figure 2:
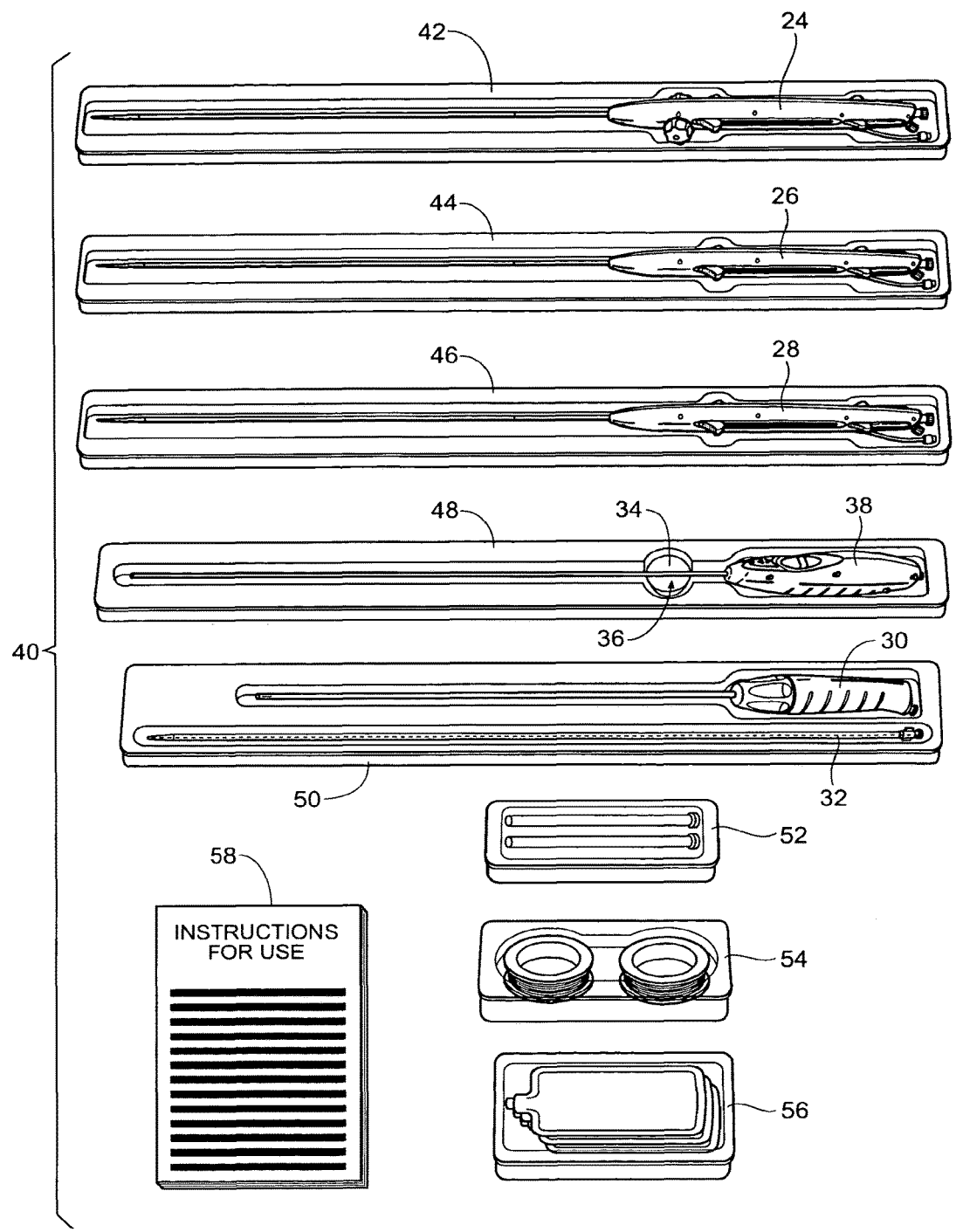
FIG. 2 is a view of the components of the system shown in FIG. 1 consolidated for use in a multiple piece kit, along with instructions for their use.

As FIG. 2 shows, the various tools and devices as just described, comprising the system 10, can be consolidated for use in a multiple piece functional kit 40.

The kit 40 can take various forms. In the illustrated embodiment, the kit 40 comprises an assemblage of individual packages 42, 44, 46, 48, 50, 52, 54, and 56, each comprising a sterile, wrapped, peel-open assembly. One or more the packages may include an interior tray made, e.g., from die cut cardboard, plastic sheet, or thermo-formed plastic material, which hold the contents. The kit 40 also preferably includes instructions or directions 58 for using the contents of the packages to carry out a desired procedure. A desired procedure using the contents of the kit 40 shown in FIG. 2 will be described in greater detail later.

The instructions for use 58 can, of course vary. The instructions for use 58 can be physically present in one or more of the packages, but can also be supplied separately. The instructions for use 58 can be embodied in separate instruction manuals, or in video or audio recordings. The instructions for use 58 can also be available through an internet web page.

A. The Component Packages

The arrangement and contents of the packages can vary. For example, as shown in FIG. 2, the kit 40 comprises eight packages 42, 44, 46, 48, 50, 52, 54, and 56. Five of these packages 42, 44, 46, 48, and 50 provide the main components of the endovascular repair system 10 as described. The remaining packages 52, 54, and 56 provide ancillary components used in the deployment of the system 10, e.g., conventional vascular access sheaths (in package 52); conventional 0.035 inch guide wires (in package 54); and bags containing heparinized saline for catheter flushing and contrast for angiography (in package 56).

In package 42, the main body 18 of the endovascular graft assembly 12 is preloaded into the main body endograft delivery components 24. In package 44, the ipsilateral lumen extension 20 of the endovascular graft assembly 12 is preloaded into the ipsilateral extension endograft delivery component 26. In package 46, the contralateral lumen extension 22 of the endovascular graft assembly 12 is preloaded into the contralateral extension endograft delivery component 28. Housed within the packages 42, 44, and 46, the components of the endovascular graft assembly 12 and the corresponding delivery components 24, 26, and 28 for the endograft components are supplied sterile to the user.

As further shown in FIG. 2, the kit 40 comprises an additional package 50 that provides the steerable endovascular guide 30 and at least one associated components; namely, the obturator 32. The kit 40 also comprises an additional package 48 that provides the endovascular staple applier 38 and at least one associated component; namely, a cassette 34 holding a plurality of endovascular staples 36. Housed within the packages 48 and 50, the steerable endovascular guide 30 and the endovascular staple applier 38 and their associated components are supplied sterile to the user.

Further details of a representative construction of the contents of the packages will now be described.

1. The Endovascular Graft a. The Main Body

In a representative embodiment (see FIG. 3A), the main body 18 of the endovascular graft is a multi-lumen endograft comprising two primary components: a graft 60 made of a biocompatible material, e.g., polyester, ePTFE, etc.; and one or more stents or scaffolds 62 made of a biocompatible metal or plastic material, e.g., Stainless steel, nickel-titanium (Nitinol), etc.

In a representative embodiment, the preferred length of the main body 18 is between 5 cm and 14 cm and most preferably between 7 cm and 10 cm. Desirably, different dimensions for the diameter of the main body 18 are provided to accommodate different anatomic dimensions of patients.

As illustrated, the multi-lumen endograft is a tube at the proximal end, which separates into two distal ipsilateral and contralateral lumens 64 and 66. The ipsilateral and contralateral lumens 64 and 66 are separated by a septum 68 or "shared wall" between them. The septum 68 extends the length of the ipsilateral lumen (in the representative embodiment, approximately 3 cm).

The main body 18 includes a proximal sealing stent 70, e.g., with diamond or "V" shaped cells, which is sewn to the inside proximal end of the graft e.g., with braided or monofilament suture. The proximal sealing stent 70 is sized and configured to ensure secure apposition to the vessel wall just below the renal arteries. The stent 70 preferably extends beyond the fabric 0 mm to 15 mm and most preferably extends 1 mm to 10 mm.

The main body 18 includes a distal locking stent 72 located in each of the two lumens 64 and 66 at the distal end of the main body 18. The stents 72 are sewn to the graft, e.g., with braided or monofilament suture. The distal locking stents 72 of the main body 18 engage with the tape covering the proximal spiral stent 86 on the lumen extensions 20 and 22 (see FIG. 3B) to help prevent component separation and provide support to the lumen openings of the main body 18.

Predetermined arrays of radiopaque markers made from biocompatible materials with high radiopacity (e.g, tantalum, platinum or gold) are desirably attached to the main body 18 to assist with visualization under fluoroscopy. The markers, like the stents, are sewn to the graft, e.g., with braided or monofilament suture or can be attached to the stent. The arrays can vary. In the illustrated embodiment, there are two (2) long contralateral side markers 74; three (3) short ipsilateral side markers 76; four (4) proximal stent marker bands 78; five (5) distal locking stent marker bands 80; and an insertion depth marker 82 near the proximal end of the septum 68 for positioning of the lumen extension.

Further details of representative constructions of the main body 18 of the endovascular graft assembly 12 can be found in co-pending, commonly owned U.S. patent application Ser. No. 11/254,444, filed Oct. 20, 2005, and entitled "Devices, Systems, and Methods for Prosthesis Delivery and Implantation, Including a Prosthesis Assembly," which is incorporated herein by reference.

b. The Lumen Extensions

In a representative embodiment (see FIG. 3B), each lumen extension 20 and 22 is sized and configured to be inserted into the corresponding ipsilateral and contralateral lumens of the main body 18, to complete the assembly of the endovascular graft 12 (see FIG. 3C). The lumen extensions 20 and 22 can be provided in various lengths and diameters to different anatomic dimensions of patients.

In a representative embodiment, each lumen extension comprises a biocompatible material 84, e.g., polyester, ePTFE, etc, and two stent or scaffold components 86 and 88 made of a biocompatible metal or plastic material, e.g., Stainless steel, nickel-titanium (Nitinol), etc.

The first stent component 86 comprises a continuous, spiral sinusoidal stent that runs the length of the lumen extension 20 and 22. The spiral stent component 86 is sized and configured to prevent kinking and maintain patency of the graft. The stent component can be sewn to the graft, e.g., with braided or monofilament suture. The proximal region of the spiral stent is further covered with material, e.g., polyester, ePTFE, etc. The covered proximal region 90 is sized and configured to engage the locking stent 72 in the main body 18 (see FIG. 3C) to prevent separation of the lumen extension from the main body 18. The covered proximal region 90 also serves to prevent the metallic stent components from coming into contact with one another.

The other stent component 88 of each lumen extension comprises a distal sealing stent. The stent component 88 can be sewn to the graft, e.g., with braided or monofilament suture. The distal sealing stent 88 is sized and configured to ensure good apposition of the lumen extension to the wall of the iliac artery. The distal sealing stent 88 preferably extends beyond the distal end of the fabric portion of the lumen extension 0 mm to 15 mm and most preferably extends 1 mm to 10 mm.

Predetermined arrays of radiopaque markers made from biocompatible materials with high radiopacity (e.g, tantalum, platinum or gold) are desirably attached to each lumen extension to assist with visualization under fluoroscopy. The markers, like the stents, can be sewn to the graft, e.g., with braided or monofilament suture or can be attached to the stent. The arrays can vary. In the illustrated embodiment (FIG. 3B), there is a proximal insertion depth marker 92 at the proximal end of the graft material and a distal marker 94 at the distal end of the graft material.

Further details of representative constructions of the lumen extensions 20 and 22 of the endovascular graft assembly can be found in co-pending, commonly owned U.S. patent application Ser. No. 11/254,444, filed Oct. 20, 2005, and entitled "Devices, Systems, and Methods for Prosthesis Delivery and Implantation, Including a Prosthesis Assembly," which is incorporated herein by reference.

2. Endovascular Graft Delivery Components a. The Main Body Delivery System i. General Overview The main body 18 of the endovascular graft assembly 12 is preloaded into the main body delivery system 24 (see FIG. 4A), which is a single use component that is supplied to the user within its package 42 in a sterile condition (see FIG. 2). The main body delivery system 24 is sized and configured to facilitate accurate placement of the main body 18 of the endovascular graft assembly 12 and to allow the physician to maintain control of the main body 18 while the endovascular staples 36 are applied.

In the illustrated embodiment (see FIG. 4A), the main body delivery system 24 comprises a delivery catheter 96 and a control handle 98 coupled to the proximal end of the delivery catheter 96. The delivery catheter 96 (see FIG. 4D) comprises a flexible inner assembly 100 and an outer graft retention jacket 102. The inner assembly 100 carries at its distal-most end a flexible radiopaque tracking nosecone 104.

When preloaded (see FIG. 4D), the main body 18 of the endovascular graft assembly 12 is attached to the inner assembly 100 in three locations. Just proximal of the nosecone 104 (i.e., toward the handle 98), the main sealing stent 70 of the main body 18 is secured by a releasable suture S1 to the inner assembly 100. Also just proximal of the nosecone 104, the inner assembly 100 includes a set of main body stabilizing arms 106. In the illustrated embodiment, there are three stabilizing arms 106. The proximal end of the preloaded main body 18 of the endovascular graft assembly is attached to the three stabilizing arms by three releasable pull wires S2, each threaded through eyelets in a respective one of the distal ends of the stabilizing arms 106 and through adjacent graft material. The distal end of the ipsilateral lumen 66 of the preloaded main body 18 is also attached to the inner assembly 100 by a releasable suture S3. These sutures and release wires S1, S2, and S3 secure the main body 18 of the endovascular graft assembly 12 to the inner assembly 100 for deployment to the targeted implantation site.

Separate wires 108, 110, and 112 extend from the handle 98 along the inner assembly 100. The separate release wires 108 and 112 are independently coupled to the sutures S1 holding the proximal sealing stent 70 (release wire 108) and the suture S3 at the distal end of the ipsilateral lumen 66 (release wire 112). The release wires 110 are continuations of the release wires S2 threaded through the stabilizing arms 106 (as previously described), so that, in the illustrated embodiment, there are actually three release wires 110, one for each arm 106. Controls 114, 116, and 118 on the handle 98 are coupled to the separate release wires 108, 110 (commonly coupled to the three wires), and 112, as will be described in greater detail later, to independently release the sutures or release wires at one location, without necessarily releasing the sutures or release wires at another location. The separate and independently controllable release wires 108, 110, 112 and make it possible to release of the main body 18 of the endovascular graft assembly 12 in a prescribed order, to deploy the main body 18 of the endovascular graft assembly 12 in a desired sequence during the graft deployment process, as will be described in greater detail later.

Figure 4D:
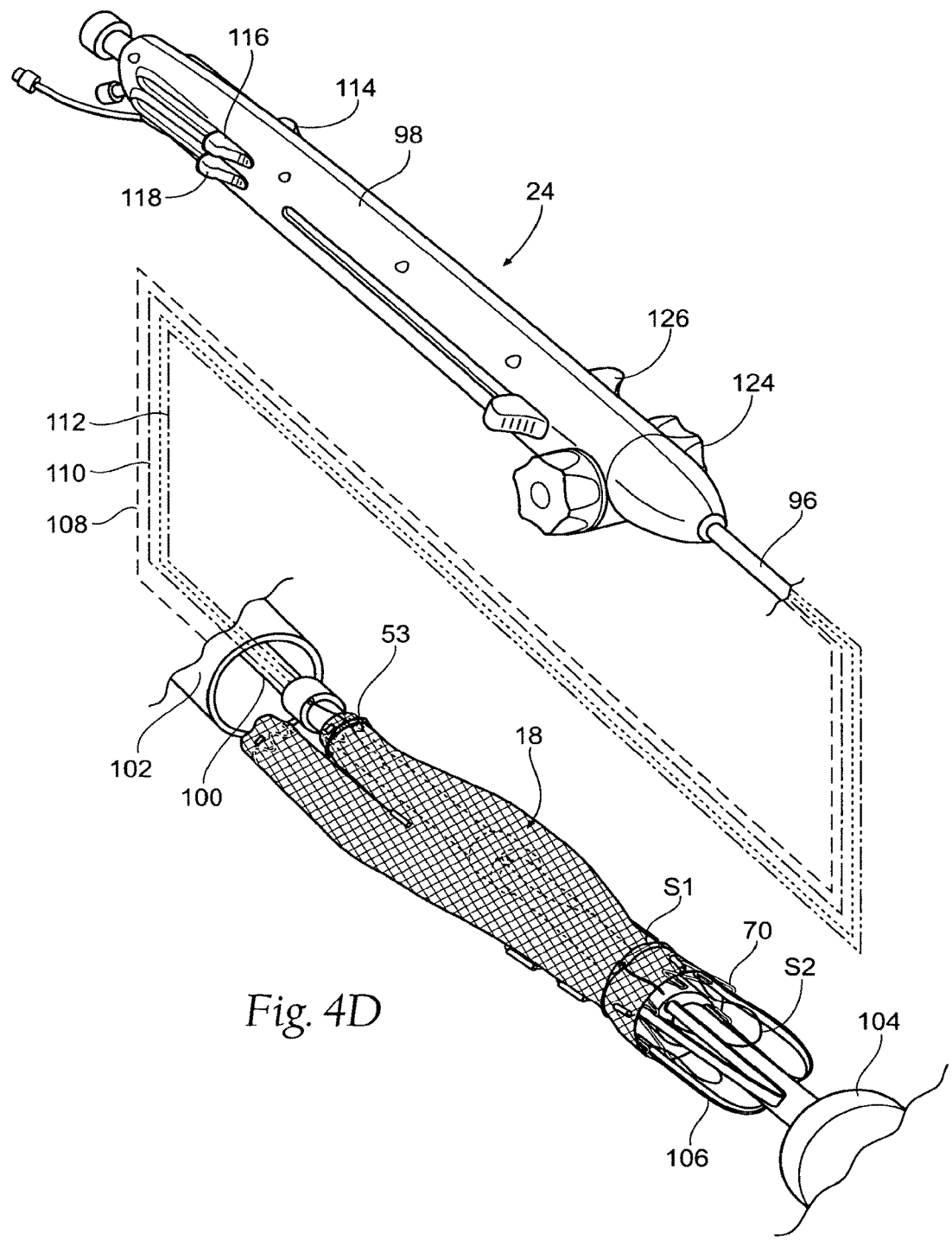
FIG. 4D is a view of the distal end of the main body delivery system shown in FIG. 4A, with parts broken away to show the attachment of the main body of the endovascular graft to the delivery system and the release wire and jacket controls that are coupled to the handle to affect a controlled stepwise release of the main body from the delivery system.
Figure 4E:
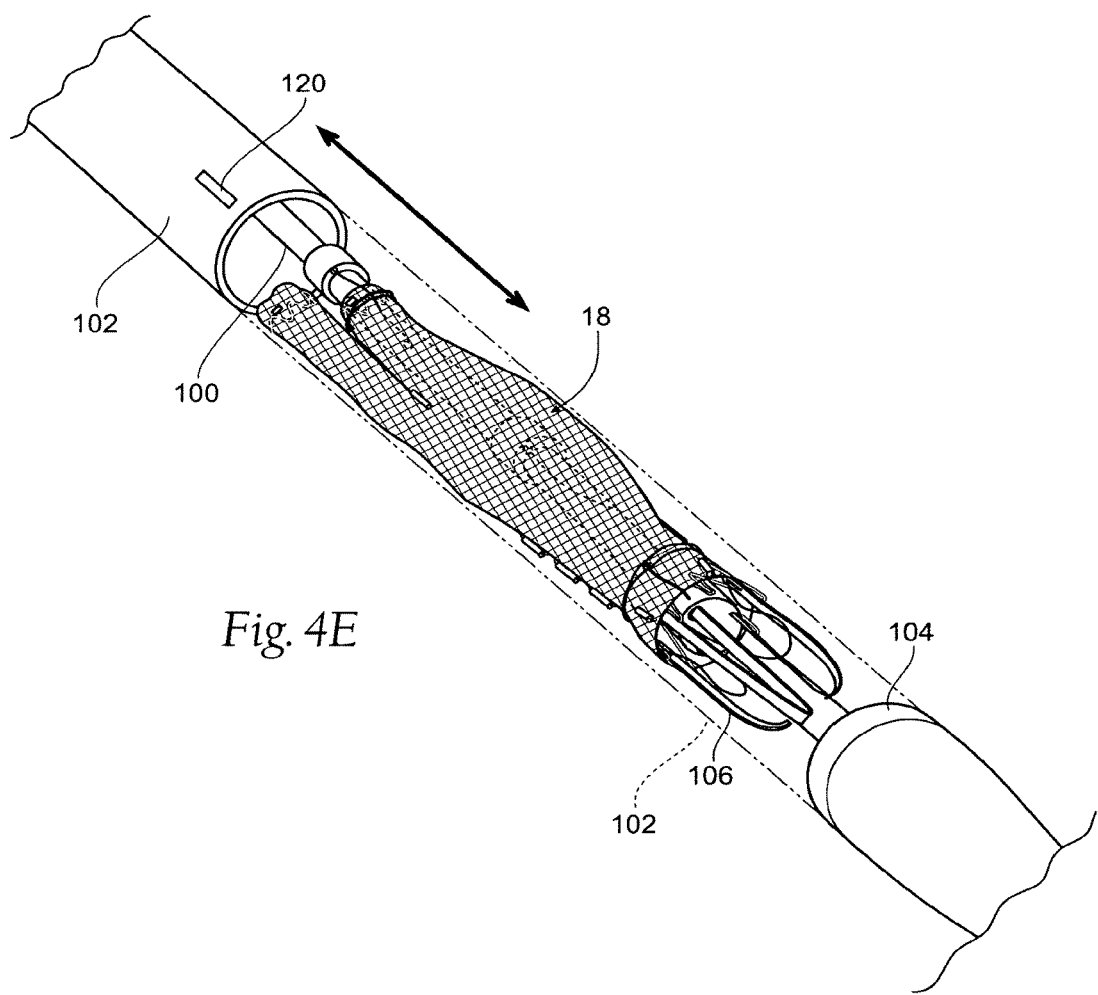
FIG. 4E is a view of the distal end of the main body delivery system showing the retracted and advanced positions of the slidable release jacket.

The graft retention jacket 102 is sized and configured to slide over and along the inner assembly 100 from an advanced position over the main body 18 of the preloaded endovascular graft assembly 12 (shown in phantom Lines in FIG. 4E) to a retracted position spaced away from the main body 18 of the preloaded endovascular graft assembly 12 (shown in solid lines in FIG. 4E). A radiopaque marker 120 is positioned at the leading edge of the graft retention jacket 102 to assist in visualization under fluoroscopy. A jacket control mechanism 122 coupled to controls 124 and 126 on the handle 98 affects retraction of the graft retention jacket 102 in a stepwise fashion—using first control 124 and then control 126, as will be described later—as well as the re-advancement of the retention jacket 102 using the single control 126 after the main body 18 has been fully deployed and it is time to withdraw the delivery system.

When in its advanced position, the graft retention jacket 102 protects the preloaded main body 18 of the endovascular graft assembly 12 as it is advanced through the patient's vasculature. When in its retracted position, the graft retention jacket 102 frees the preloaded main body 18 of the endovascular graft assembly 12 for deployment by operation of the controls 124 and 126 on the handle 98 during the graft deployment process.

The actuating components on the control handle 98 (see FIGS. 4B and 4C) include a jacket retraction knob 124 and a jacket retraction slide 126, which are coupled to the jacket control mechanism 122 just described (as shown in FIG. 4D). The jacket retraction knob 124 is actuated by rotation and is coupled to a rack and pinion component of the jacket control mechanism 122 within the handle 98. The rack and pinion component applies a mechanical advantage in response to rotation of the knob 124 sufficient to overcome the initial resistance of the graft retention jacket 102 to axial movement beyond the proximal sealing stent 70 of the main body 18 of the endovascular graft assembly 12. Once free of the proximal sealing stent 70, the rack and pinion component of the jacket control mechanism 122 is automatically released from the jacket retraction knob 124 (the knob 124 will accordingly spin freely), and subsequent control passes to the jacket retention slide 126. Pulling on the jacket retention slide 126 (which does not provide a mechanical advantage) suffices to complete the retraction of the jacket 102. This control sequence provides the physician with tactile feedback during the retraction of the jacket 102. After retracted in this manner, the jacket 102 can be advanced back toward the nosecone 104 using the jacket slide 126 when it is time to withdraw the delivery system.

The actuating components on the control handle (see FIGS. 4B and 4C) also include a proximal sealing stent release slide 114, a graft release slide 116, and an ipsilateral lumen release slide 118. The proximal sealing stent release slide 114 is coupled to the release wire 110 for the proximal sealing stent 70 (see FIG. 4D). The graft release slide 116 is coupled to the three separate release wires 110 for the stabilizing arms 106 (also shown in FIG. 4D). The ipsilateral lumen release slide 118 is coupled to the separate release wire 112 for the distal end of the ipsilateral lumen 66 (as further shown in FIG. 4D).

Once the graft retention jacket 102 is retracted (as just described), pulling on the proximal sealing stent release slide 114 opens the proximal sealing stent 70. Despite opening the proximal sealing stent 70, the proximal and ipsilateral ends of the main body 18 of the endovascular graft assembly 12 remain attached to the inner assembly 100 of the endovascular graft delivery system. The physician maintains control of the main body 18 of the endovascular graft assembly 12 for further final positioning and for the application of the staples 36, as will be described in greater detail later.

Once positioned in a desired location and/or after insertion or implantation of staples to secure the main body 12 to the vessel wall, pulling on the graft release slide 116 releases the proximal end of the main body 18 of the endovascular graft assembly 12 from the stabilizing arms 106. Despite opening the proximal sealing stent 70 and the stabilizing arms, the physician still maintains control of the ipsilateral end of the main body 18 of the endovascular graft assembly, which remains attached to the inner assembly 100. Next pulling on the ipsilateral lumen release slide 118 opens and releases the ipsilateral lumen 66 from the delivery catheter 96.

If desired, and as shown in phantom lines in FIG. 4A, a stationary outer jacket 220 may be provided that extends for a distance from the proximal end of the handle 98 over the delivery catheter 96 (the jacket 102) slides within the stationary outer jacket 220). The stationary jacket 220 provides a seal interface with a hemostatic valve of the introducer sheath at the access site. The stationary jacket 220 can be made of a suitable medical grade plastic, such as Fluroinated Ethylene Propylene (FEP) as non-limiting example. The stationary outer jacket 220 provides column strength and lubricity to reduce friction during sliding actuation of the jacket 102.

The delivery catheter 96 is desirably sized to present a minimum diameter according to the diameter of the main body 18 of the endovascular graft assembly 12 it carries. The delivery catheter 26 is desirably sized and configured with a lumen accommodating conventional over-the-wire delivery within a patient's vasculature, e.g., using a conventional 0.035 or 0.038 inch guide wire. In representative embodiment, the overall length of the delivery catheter is preferably between 40 and 120 cm and most preferably between 50 and 90 cm.

Further details of representative constructions of a main body delivery system 24 can be found in co-pending, commonly owned U.S. patent application Ser. No. 11/254,116, filed Oct. 20, 2005, and entitled "Devices, Systems, and Methods for Prosthesis Delivery and Implantation," which is incorporated herein by reference.

ii. Hemostasis Control

In a representative embodiment (see FIG. 5A), the proximal end of the handle 98 (near the sliding controls 114, 116, and 118 just described) includes a hemostatic seal assembly 128. As FIG. 5D shows, a flush passage 130 (for conveying heparinized saline to flush the delivery catheter 96 prior to deployment) communicates with the space between the inner assembly 100 and jacket 102 through the hemostatic seal assembly 128. As FIG. 5D also shows, the individual release wires 108, 110, and 112 for the proximal sealing stent release slide 114, the graft release slide 116 (one release wire 110 for each stabilizing arm 106), and the ipsilateral lumen release slide 118, as previously described, also pass from the slide controls 114, 116, and 118 within the handle in a sealed fashion through the hemostatic seal assembly 128 for passage along the inner assembly 100 to the distal end of the delivery catheter 96, where they connect to their respective components, as previously described. The hemostatic seal assembly 128 allows flushing to occur and prevents blood, which can enter the space between the outer jacket 102 and the inner assembly 100 catheter tube during use, from entering the interior of the handle 98.

In the illustrated embodiment (see FIGS. 5B and 5C), the hemostatic seal assembly 128 includes first and second substantially rigid seal components 132 and 134, made e.g. of an inert material. The first seal component 132 comprises a center post 136 and a collar 138 that extends radially from an end of the post 136. The collar 138 forms a mount for coupling the hemostatic seal assembly 128 within the confines of the handle 98, as FIG. 5D shows.

The center post 136 defines a passage that sealingly engages the flush passage 130 of the delivery catheter 96, to provide a fluid seal.

The second seal component 134 comprises an annular ring that fits about the post. As further shown in FIGS. 5B and 5C, the hemostatic seal assembly 128 further includes an annular septum or gasket 140 that also fits about the post 136. When assembled, the gasket 140 is sandwiched between the second seal component 134 and the collar 138 of the first seal component 132. The gasket 140 is made of a soft material, like silicone rubber. The collar 138 and the second seal component 134 include coaxial through-holes or guide tubes 142 to accommodate passage of the various release wires 108, 110, and 112 through the annular gasket 140. The through-holes 142 act as bearing surfaces or guides for the release wires 108, 110, and 112 on opposite sides of the annular gasket 140.

The gasket 140 provides a dynamic fluid seal for the release wires 108, 110, and 112. The fluid seal is maintained even if a release wire becomes tensioned during use in a non-axial direction. The length and diameter of the bearing surfaces of the through holes 142 and the thickness of the annular gasket 140 can vary depending upon the diameter of the release wires 108, 110, and 112 and direction or angle the release wires 108, 110, and 112 make as they exit the bearing through holes 142, to prevent tear out or sawing of the material of the gasket 140.

b. The Lumen Extension Delivery System

Each lumen extension 20 and 22 of the endovascular graft assembly is preloaded into a lumen extension delivery system, respectively 26 and 28 (see FIG. 6A), each of which is a single use component that is supplied to the user within its package 44 and 46 in a sterile condition. Each lumen extension delivery system 26 and 28 is sized and configured to facilitate accurate placement of its lumen extension 20 and 22 of the endovascular graft assembly 12.

In the illustrated embodiment (see FIG. 6A), each lumen extension delivery system 26 and 28 comprises a delivery catheter 144 and a control handle 146 coupled to the proximal end of the delivery catheter 144. The delivery catheter 144 (see FIG. 6D) comprises a flexible inner assembly 148 and an outer graft retention jacket 150. The inner assembly 148 carries at its distal-most end a flexible radiopaque tracking nosecone 152.

When preloaded (see FIG. 6D), the lumen extension 20 or 22 of the endovascular graft assembly is attached to the inner assembly 148 by a releasable suture S4 at the proximal end of the spiral stent 86. A release wire 154 extends from the handle 98 along the inner assembly 148 and is coupled to the suture S4 holding the proximal end of the spiral stent 86. A sliding control 156 on the handle 146 is coupled to the release wire 154 (as will be described in greater detail later), to release the suture S4 and thereby release of the lumen extension 20 or 22 of the endovascular graft assembly 12 from the inner assembly 148 during the graft deployment process, as will be described in greater detail later.

Figure 6A:
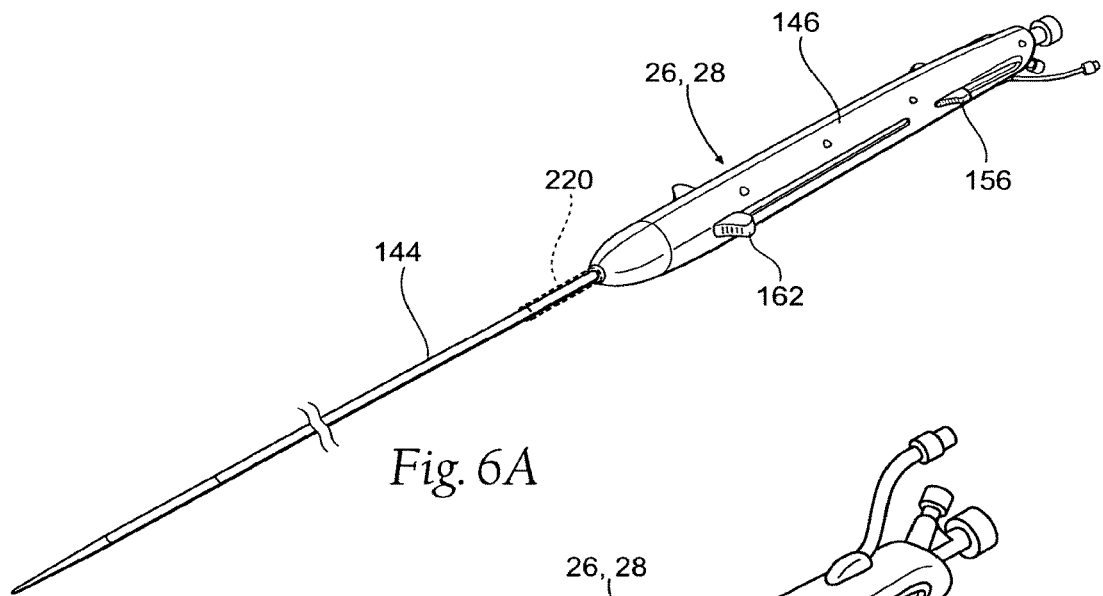
FIG. 6A is a view of the delivery system for a lumen extension of the endovascular graft, which forms a part of the system shown in FIG. 1.
Figure 6B:
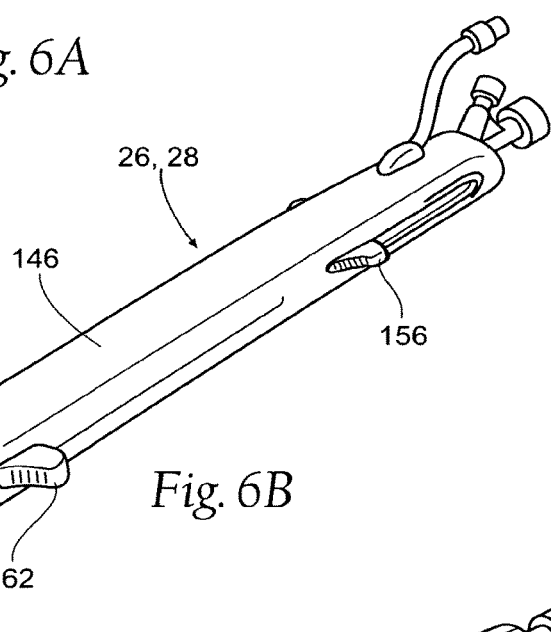
FIGS. 6B and 6C are views of the top and bottom of the control handle of the lumen extension delivery system shown in FIG. 6A.
Figure 6C:
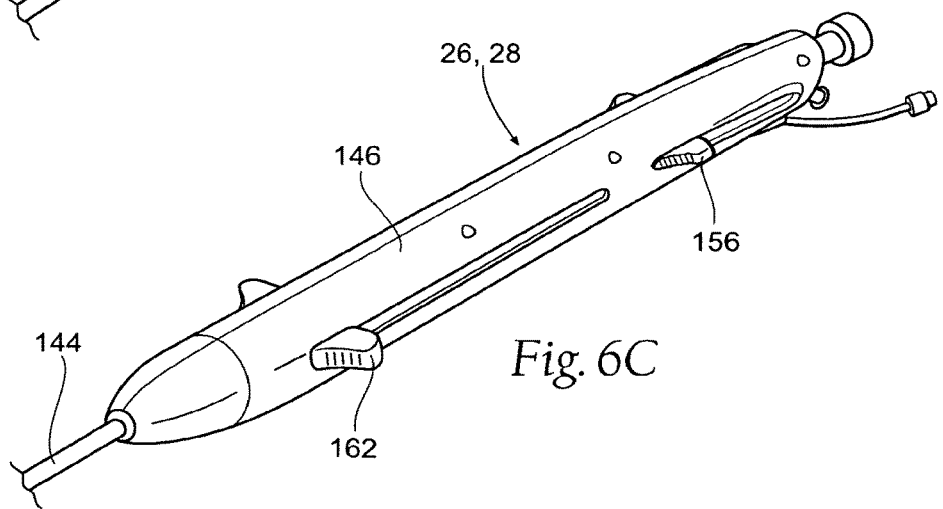
Figure 6D:
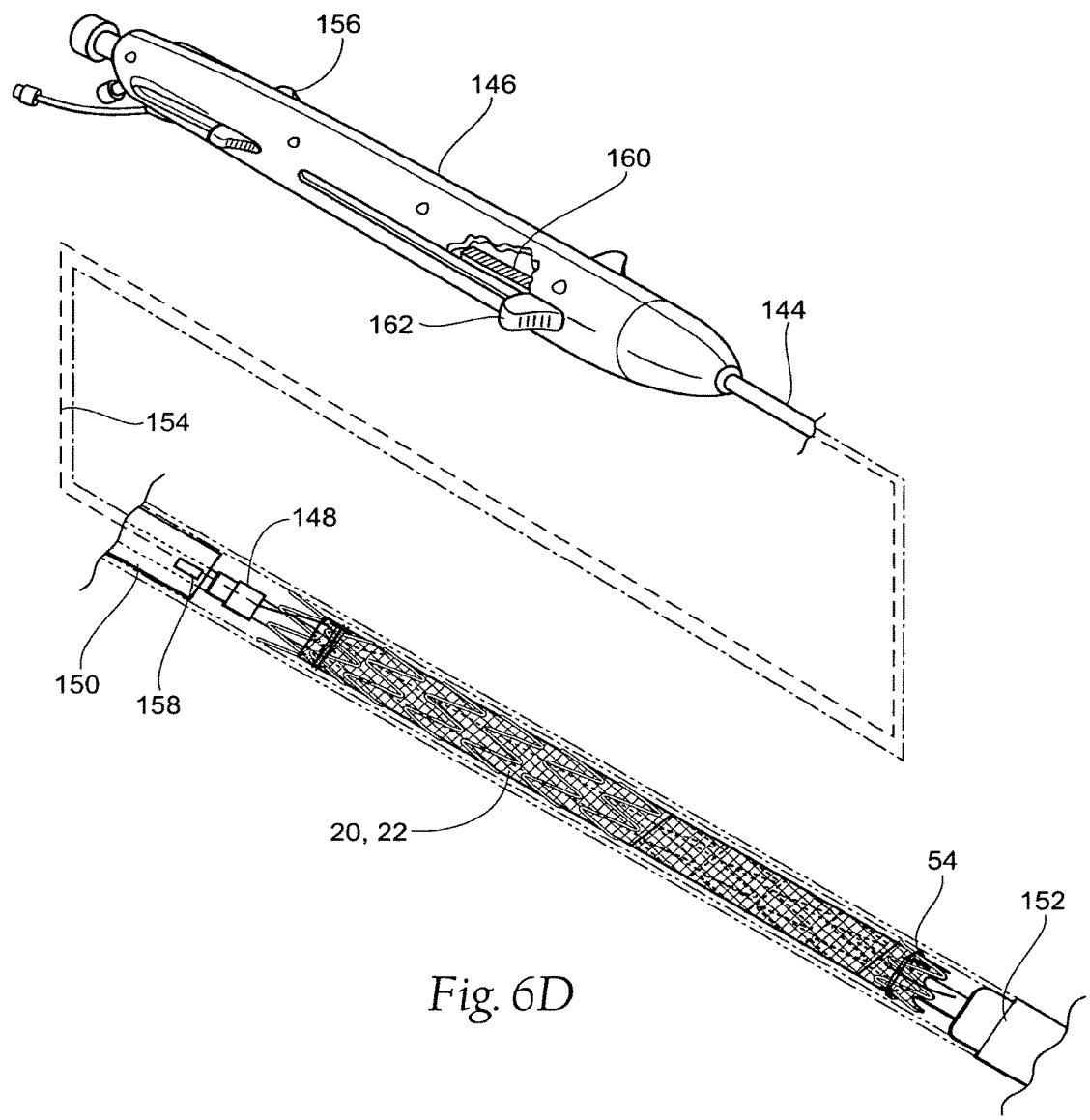
FIG. 6D is a view of the distal end of the lumen extension delivery system shown in FIG. 6A, with parts broken away to show the attachment of a lumen extension of the endovascular graft to the delivery system and the release wire and jacket controls that are coupled to the handle to affect a controlled release of the lumen extension from the delivery system.

The graft retention jacket 150 is sized and configured to slide over and along the inner assembly 148 from an advanced position over the preloaded lumen extension 20 or 22 of the endovascular graft assembly 12 (shown in phantom Lines in FIG. 6D) to a retracted position spaced away from the preloaded lumen extension 20 or 22 of the endovascular graft assembly 12 (shown in solid lines in FIG. 6D). A radiopaque marker 158 is positioned at the distal end of the graft retention jacket 150 to assist in visualization under fluoroscopy. A control mechanism 160 coupled to a sliding control 162 on the handle 146 affects advancement and retraction of the graft retention jacket 150, as will be described later.

When in its advanced position, the graft retention jacket 150 protects the preloaded lumen extension 20 or 22 of the endovascular graft assembly 12 as it is advanced through the patient's vasculature. When in its retracted position, the graft retention jacket 150 frees the preloaded lumen extension 20 or 22 of the endovascular graft assembly 12 for deployment by operation of the sliding control 162 on the handle 98 during the graft deployment process.

The actuating components on the control handle 146 (see FIGS. 6B and 6C) include a jacket retraction knob 162 (coupled to the jacket control mechanism 160) and a proximal spiral stent release slide 156 (coupled to the release wire 154 just described (as shown in FIG. 6D). Pulling on the jacket retraction slide 162 suffices to retract the jacket 150. Once the graft retention jacket 150 is retracted (as just described), pulling on the proximal spiral stent release slide 156 opens and releases the lumen extension 20 or 22 from the inner assembly 148.

A stationary outer jacket 220 may also be provided for the lumen extension delivery systems 26 and 28 (as shown in phantom lines in FIG. 6A). As previously described with respect top the main body delivery system 24, the stationary outer jacket 220 extends for a distance from the proximal end of the handle 146 over the delivery catheter 144 (the jacket 150) slides within the stationary outer jacket 220). The stationary jacket 220 provides a seal interface with a hemostatic valve of the introducer sheath at the access site. As previously described, the stationary jacket 220 can be made of a suitable medical grade plastic, such as Fluroinated Ethylene Propylene (FEP) as non-limiting example. The stationary outer jacket 220 provides column strength and lubricity to reduce friction during sliding actuation of the jacket 150.

Each lumen extension delivery catheter 144 is desirably sized to present a minimum diameter according to the diameter of the lumen extension 20 or 22 of the endovascular graft assembly 12 it carries. The delivery catheter 144 is desirably sized and configured with a lumen accommodating conventional over-the-wire delivery within a patient's vasculature, e.g., using an appropriately sized guide wire. In representative embodiment, the over-all length of the lumen extension delivery catheter 144 is preferably between 40 and 120 cm and most preferably between 50 and 90 cm.

The lumen extension delivery catheter can include a hemostatic valve assembly of the type previously described and as shown in FIGS. 5A to 5D.

Further details of representative constructions of a lumen extension delivery system can be found in co-pending, commonly owned U.S. patent application Ser. No. 11/254,116, filed Oct. 20, 2005, and entitled "Devices, Systems, and Methods for Prosthesis Delivery and Implantation," which is incorporated herein by reference.

c. Endovascular Stapling System

The endovascular stapling system 16 comprises steerable endovascular guide 30 and a companion obturator 32 (see FIGS. 7A and 7B) for over-the-wire, intravascular deployment of the steerable endovascular guide 30. The endovascular stapling system 16 also comprises a plurality of endovascular staples 36 (FIG. 8A) and, desirably, a cassette 34 for holding the staples 36 (see FIG. 8B), as well as an endovascular staple applier 38 (see FIGS. 9A and 9B).

d. Steerable Endovascular Guide and Companion Obturator

The steerable endovascular guide 30 is a single use component that is supplied with a companion obturator 32 to the user within its package 50 in a sterile condition. The steerable endovascular guide 30 is sized and configured to direct the endovascular staple applier 38 to the desired location for implantation of one or more endovascular staples 36.

The steerable endovascular guide 30 (see FIGS. 7A and 7B) includes a guide tube 164 and a handle 166 coupled to the proximal end of the guide tube 164. The guide tube defines an open interior lumen 168 accommodating passage of the obturator 32 (during deployment) and the endovascular staple applier 38 (during use).

The distal portion of the guide tube 164 can be deflected in one direction (as shown in phantom lines in FIG. 7A) and straightened by a steering wire (not shown) coupled to a rotational deflector knob 170 on the handle 166. In a representative embodiment, the over-all length of guide tube 164 and handle 166 is preferably between 40 and 120 cm and most preferably between 50 and 90 cm, and the length of the deflectable tip is preferably between 1 and 10 cm and most preferably between 2 and 5 cm. A C-shaped radiopaque marker 172 is located at the distal tip of the guide tube 164 to aid in orientation under fluoroscopy.

In a representative embodiment, the obturator 32 is desirably sized and configured with a lumen 174 accommodating conventional over-the-wire delivery within a patient's vasculature, e.g., using an appropriately sized guide wire.

Further details of representative constructions of a steerable endovascular guide 30 can be found in co-pending, commonly owned U.S. patent application Ser. No. 11/254,619, filed Oct. 20, 2005, and entitled "Devices, Systems, and Methods for Guiding an Operative Tool into an Interior Body," and co-pending, commonly owned U.S. patent application Ser. No. 11/254,116, filed Oct. 20, 2005, and entitled "Devices, Systems, and Methods for Prosthesis Delivery and Implantation," which are both incorporated herein by reference.

B. The Endovascular Staple and Companion Cassette

The endovascular staple 36 (see FIG. 8A) is a single use component that is supplied, desirably in a companion cassette, to the user within a package in a sterile condition. The endovascular staple 36 is sized and configured to attach the endovascular graft assembly 12 to a vessel wall.

In the illustrated embodiment (see FIG. 8A) the endovascular staple 36 comprises a main staple body 176 that is helical-shaped. The helical-shape allows the endovascular staple 36 to pierce and engage tissue in response to rotation of the main staple body 176, thereby securing attachment of the endovascular graft assembly 12 to a vessel wall.

In a representative embodiment, the main staple body 176 is manufactured from medical grade wire having a diameter of from 0.1 mm to 1 mm. In a representative embodiment, the endovascular staple 36 is approximately between 2 mm to 12 mm in over-all length and approximately from approximately 1 mm to 10 mm in maximum diameter. The leading end 178 of the main staple body 176 is desirably sharpened to facilitate atraumatic deployment through the graft materials and vessel wall. The proximal end 180 of the main staple body 176 is desirably closed to prevent over-penetration of the endovascular staple 36.

Desirably, a plurality of staples 36 (e.g., ten) are provided in a cassette 34 (see FIG. 8B), to allow easy and accurate loading into the endovascular staple applier 38. The cassette 34 includes a base 208 having a plurality of spaced apart staple ports or stations 210, each sized to house a staple 36. A cover 212 rotates on the base 208 (see FIG. 8C). The cover 212 overlies the ports 210, closing them, except for an open notch region 214, which permits access to a single one of the ports 210. In use, an operator rotates the cover 212 to expose one port 210 and the staple 36 it contains. The operator operates the staple applier 38 to load the staple 36 from the exposed port 210, as will be described in greater detail. After implanting the withdrawn staple 36, the operator rotates the cover 212 to expose another one of the ports 210 and the staple 36 it contains. The operator again operates the staple applier 38 to load the staple 36 from the exposed port 210 for implantation. In this way, the cassette 34 aids the operator in loading individual staples on the staple applier 36 for implantation in a single fire (one at a time) fashion.

Further details of representative constructions of an endovascular staple 36 and companion cassette 34 can be found in co-pending, commonly owned U.S. patent application Ser. No. 11/255,116, filed Oct. 20, 2005, and entitled "Devices, Systems, and Methods for Prosthesis Delivery and Implantation," which is incorporated herein by reference.

C. Endovascular Staple Applier

1. Overview

The endovascular staple applier 38 (see FIGS. 9A and 9B) is a single use component that is supplied to the user within a package 48 in a sterile condition. In the illustrated embodiment, the endovascular staple applier 38, a supply of endovascular staples 36, and the staple cassette 34 are provided, for the sake of convenience, in a single package 48. The endovascular staple applier 38 is sized and configured to pass through the lumen 168 of the steerable endovascular guide tube 164 and to be selectively operated to implant one or more endovascular staples 36 through the graft materials and vessel wall.

In the illustrated embodiment, the endovascular staple applier 38 comprises an applier catheter 182 and a control handle 184 coupled to the end of the applier catheter 182. The applier catheter 182 carries a rotationally driven member 186 at its distal end. A battery powered motor 188 enclosed within the handle 184 is coupled to the driven member 186, to selectively rotate the driven member 186 either in a forward (e.g., clockwise) direction and reverse (e.g., counterclockwise) direction. A control circuit 190 in the handle 184 is coupled to the motor 188 and to a forward control button 192 and a reverse control button 194 on the handle. The control circuit 190 governs operation of the operation of the motor 188 according to pre-programmed operating parameters in response to user commands received by manipulation of the buttons 192 and 194.

In use (see FIGS. 10A to 10H), an endovascular staple 36 is loaded into the driven member 186 from the cassette 34, e.g., by placing the distal end of the applier catheter 182 into an exposed staple port 210 in the cassette 34 and pressing the reverse control button 194 (FIG. 10A). The now loaded endovascular staple applier 38 is passed through the guide tube 164 of the endovascular guide 30 (FIG. 10B), which has been manipulated beforehand to be at an intended implantation site for the endovascular staple 36.

Once the endovascular staple applier 38, loaded with a staple, is positioned at the desired location (FIG. 10C), the physician presses the forward control button 192 to command rotation of the endovascular staple 36 in the forward direction (i.e., into tissue).

The control circuit 190 is desirably pre-programmed to require a two-stage implantation process. The first stage commands only a partial implantation of the staple 36. In the first stage, the physician is allowed to ascertain whether the staple 36 is placed correctly at the desired location and that the desired located is suitable for implantation of the staple 36. While in the first stage, the physician is allowed to retract the staple 36 (by pressing the reverse control button 194) and to re-position the staple 36.

The control circuit 190 commands a full final deployment of the staple 36 only after a deliberate entry of the second stage. In the first and second stages, the control circuit 190 generates audible tones and visual indicators e.g., blinking lights, during operation of the motor 188, to indicate the position of the staple and available direction of motion.

Once the staple 36 is implanted, the endovascular staple applier 38 is withdrawn through the endovascular guide. The cassette cover 212 is rotated to reveal another staple port 210 and the staple 36 it contains. The staple applier 38 is reloaded. The endovascular guide 30 is manipulated to another desired implantation site, and the endovascular staple applier 38 (reloaded with another staple 36) is redeployed and operated in the manner just described. The endovascular staple applier 38 is intended to be loaded, deployed, and reloaded in this way multiple times for a single patient.

Further details of representative constructions of an endovascular staple applier 38 and methods of its use can be found in co-pending, commonly owned U.S. patent application Ser. No. 11/254,950, filed Oct. 20, 2005, and entitled "Devices, Systems, and Methods for Prosthesis Delivery and Implantation, Including the Use of a Fastening Tool" which is incorporated herein by reference.

2. Tracking the Relative Position of the Endovascular Staple Applier in the Endovascular Guide Desirably, the endovascular staple applier 38 includes indicia 196, which is visible to a naked eye (i.e., without resort to fluoroscopic visualization or other visualization techniques that augment human vision) the indicates the extent to which the driven distal end 186 of the applier catheter 182, which carries the endovascular staple 36, resides within the guide tube 164 of the steerable endovascular guide 30. In particular, the visible indicia 196 indicates when the driven distal end 186 of the applier catheter 182 and the staple 36 it carries have arrived at a predetermined location within the guide tube near to but still within the distal end of the guide tube 164. In this way (see FIG. 11C), the physician can quickly and accurately ascertain, without resort to fluoroscopic visualization, that the distal end of the applier catheter 182, and the endovascular staple 36 it carries, are positioned wholly within the confines of the guide tube 164, ready for final deployment, once the guide tube 164 is placed at the intended implantation site. The visible indicia 196 can also indicate to extend to which the driven distal end 186 of the applier catheter 182 has been extended outside the distal end of the guide tube 164.

Figure 11A:
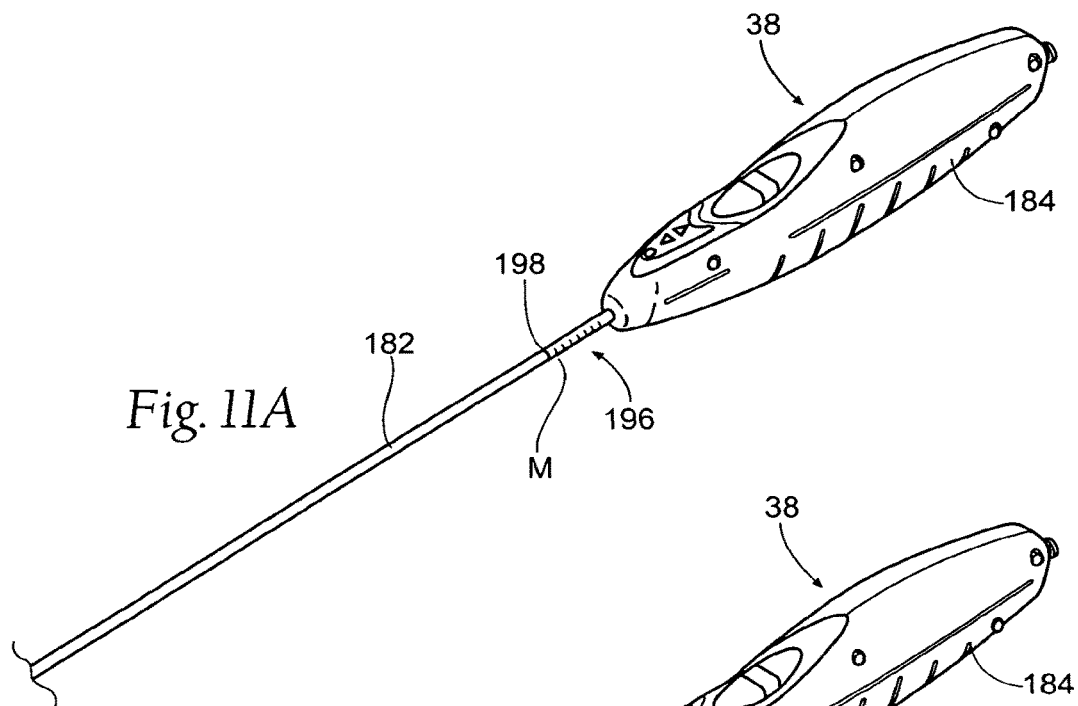
FIG. 11A is a view showing a fastener applier of a type shown in FIG. 9A, which includes indicia visable to a naked eye.

In the illustrated embodiment (see FIG. 11A), the indicia 196 comprises visible material or markings on the most proximal section of the applier catheter 182, adjacent the handle 184, that is marked or colored differently or is otherwise differentiated from the remainder of the applier catheter 182. In a representative example, a prescribed length of contrast-colored tubing 198 can be placed at the most proximal end of the applier catheter 182, where it exits the handle 184.

The contrast-color tubing 198 has a prescribed length. The distal end of the tubing 198 marks a line of differentiation between the tubing 198 and the remainder of the applier catheter 182. The length is selected so that the distal end of the tubing 198 registers with the insertion port/hemostatic seal 200 on the handle 166 of the steerable endovascular guide 30 (see FIG. 11B) when the driven distal end 186 of applier catheter 182 rests at a desired inset distance d within the distal end of the guide tube 164 (see FIG. 11C).

In this way, the indicia 196 indicates when the applier catheter 182 has reached a desired insertion depth within the guide tube, and is ready to be further advanced beyond the guide tube 164 to implant the endovascular staple 36. The contrast-color tubing 198 may further include additional markings M along its length by which the physician can gauge advancement of the applier catheter 182 beyond the endovascular guide 20.

The indicia 196 makes it possible for the physician, without resort to fluoroscopic visualization, to always know whether the endovascular staple 36 is within or outside the endovascular guide 30.

3. The Motor Control Circuit

Figure 13A:
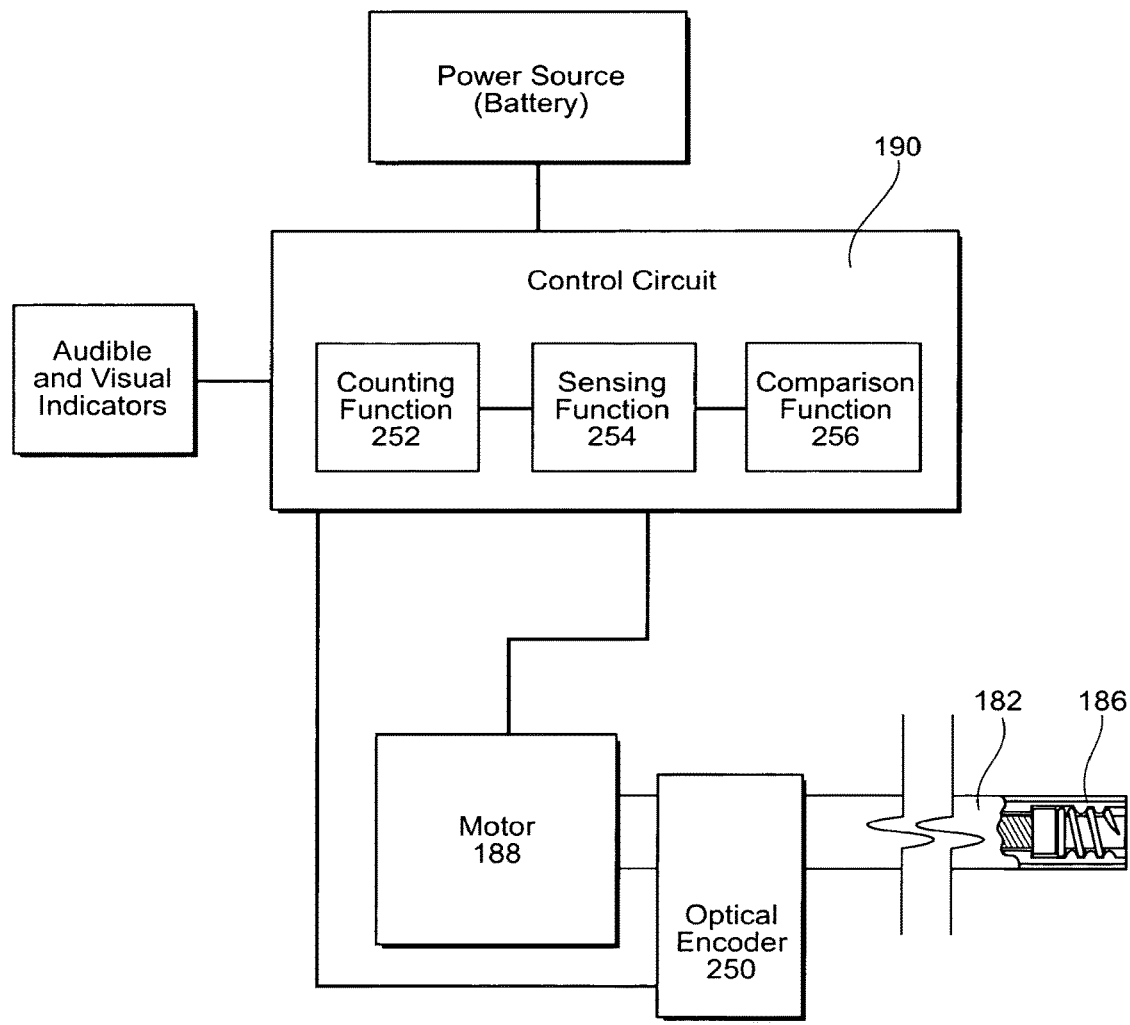
FIG. 13A is a schematic view of the motor control functions of a representative control circuit for the fastener applier shown in FIG. 9A.

In a representative embodiment (see FIG. 13A), the control circuit 190 for the motor includes an optical encoder 250 coupled to a counting function 252, to enable counting the revolutions of the battery powered motor 188. The control circuit 190 also includes a sensing function 254 that senses the magnitude of current being drawn by the motor 188, for deriving torque that the motor 188 is encountering. The control circuit 190 also includes a comparison function 256 that compares the magnitude of the sensed torque (current) with set torque limits in either the forward or reverse direction, to change the state of operation should excess torque conditions be encountered.

The control circuit 190 carries embedded code, which expresses pre-programmed rules or algorithms under which different operation states are entered and motor command signals are generated in response to input from the external control sources and the counting, sensing, and comparison functions. The pre-programmed rules or algorithms of the control circuit 190 are designed to conserve power consumption, placing the circuit into a standby (wait) mode between staple loading and deployment cycles. This makes it possible to power up the staple applier just once and to leave the staple applier on during an entire procedure, avoiding time consumed in repeated power ups and power downs. The pre-programmed rules or algorithms of the control circuit also dictate that a desired sequence of steps is faithfully followed in loading, deploying, and reloading the staples, prompting the physician at the initiation of each step and not allowing any short-cuts or deviations along the way.

Features of the pre-programmed rules or algorithms of a representative control circuit 190 for the staple applier will now be described in greater detail.

Power Up/System Self-Check

Figure 13B:
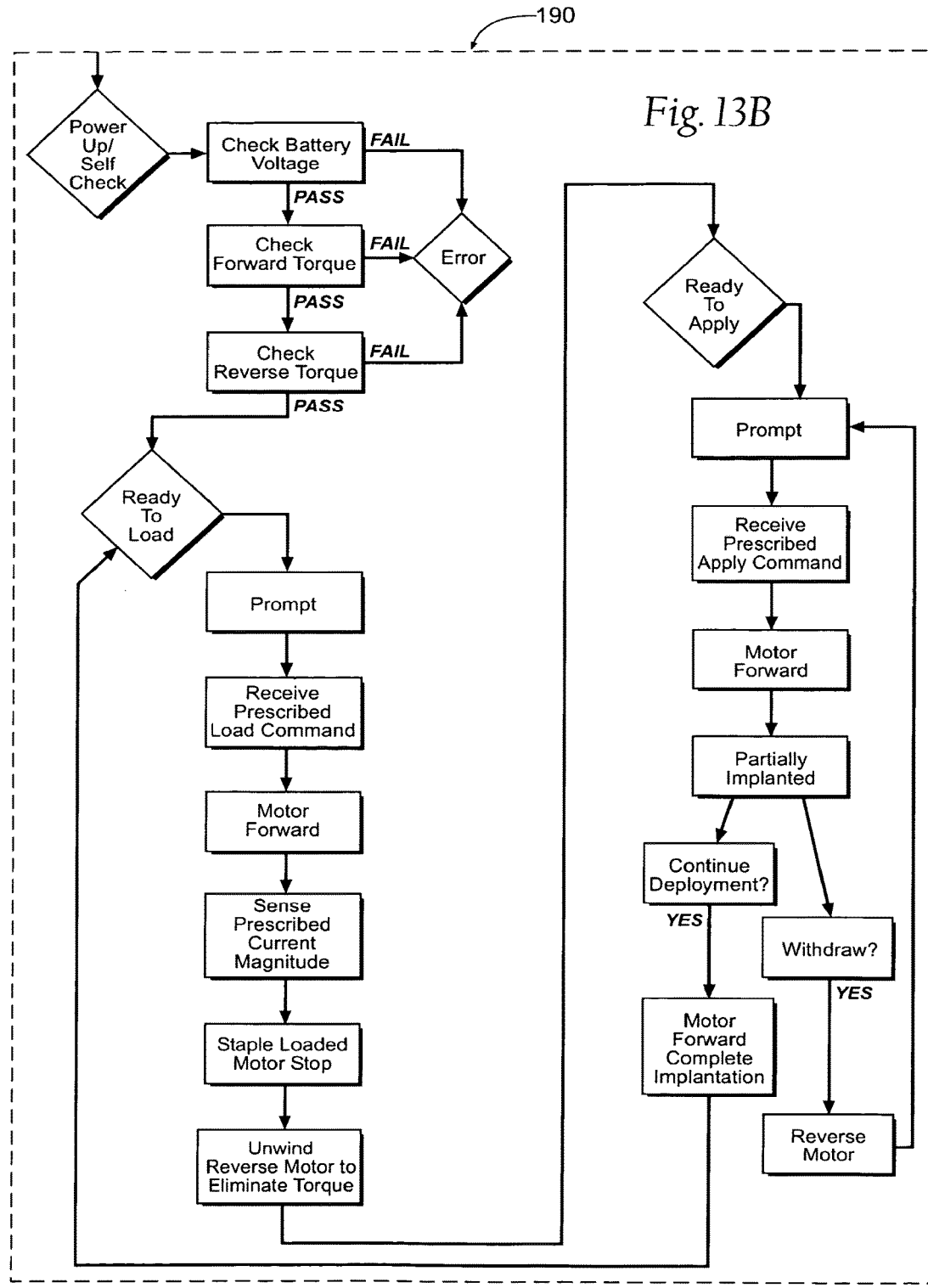
FIG. 13B is a schematic flow diagram of the operational states of the control circuit shown in FIG. 13A.

In a representative implementation (see FIG. 13B), the pre-programmed rules or algorithms of the control circuit 190 enter a POWER UP state when an operator enters a prescribed power up command, e.g., when the operator presses and holds the reverse control button 194 for a prescribed amount of time. In the POWER UP state, the pre-programmed rules or algorithms of the control circuit 190 first check battery voltage against a set minimum. The POWER UP state proceeds if the battery voltage exceeds the set minimum. Otherwise, the pre-programmed rules or algorithms of the control circuit 190 enter a LOW BATTERY FATAL state.

Absent a LOW BATTERY FATAL state, the pre-programmed rules or algorithms of the control circuit 190 enable the optical encoder and drive the motor 188 in a forward direction for a set period of time. The counting and sensing functions of the control circuit 190 count the number of revolutions and sense forward current. If the forward current exceeds a set maximum current level (as determined by the comparison function), the pre-programmed rules or algorithms of the control circuit 190 enter a FORWARD TORQUE FATAL state. Otherwise, the sensed forward current is registered by the pre-programmed rules or algorithms of the control circuit 190 as a base line for forward torque.

Absent a FORWARD TORQUE FATAL state, the pre-programmed rules or algorithms of the control circuit 190 enable the optical encoder and counting function, and drive the motor 188 in a reverse direction for a set period of time. The counting function of the control circuit 190 counts the number of revolutions, while the sensing function senses reverse current. If the reverse current exceeds a set maximum current level (as determined by the comparison function), the pre-programmed rules or algorithms of the control circuit 190 enter a REVERSE TORQUE FATAL state. Otherwise, the sensed reverse current is registered by the pre-programmed rules or algorithms of the control circuit 190 as a base line for reverse torque.

Audible tones and visual indicators (e.g. blinking lights) coupled to the control circuit 190 desirably accompany the POWER UP state as the system self-check is accomplished. If no fatal states are encountered during the POWER UP sequence, the pre-programmed rules or algorithms of the control circuit 190 enter a READY TO LOAD state. The pre-programmed rules or algorithms of the control circuit 190 enable a ready to load prompt, e.g., blinking a reverse green arrow 202 (see FIG. 9B), to indicate to the user that the endovascular staple applier 38 is ready to load the first endovascular staple. If a fatal state is encountered, the pre-programmed rules or algorithms of the control circuit 190 enable a different prompt, e.g., illuminating a red error light 204 (see FIG. 9B), indicating that the endovascular staple applier 38 has encountered an error.

In addition, there are other checks that can be performed during the POWER UP state, including checking the encoder and the watchdog function for operation.

In a representative implementation, the pre-programmed rules or algorithms of the control circuit 190 allow the operator to clear the error state one time, e.g., by pressing the forward control button 192. After the error has been cleared, the self-check sequence of the POWER UP state will reinitiate. If during the second self check sequence, a fatal state is again encountered, the pre-programmed rules or algorithms of the control circuit 190 either disable the endovascular staple applier 38 from use, or again enable the error prompt. In the latter instance, the instructions for use 58 desirably will inform the operator not to use an endovascular staple applier 38 that has encountered a start-up error twice.

Ready to Load State: Load Staple

After the staple applier has been powered up and is in the READY TO LOAD state, the operator is able to load the endovascular staple by initiating a prescribed input command, e.g., by pushing the reverse control button 194. The distal end of the endovascular staple applier catheter 182 is intended to be inserted into a staple port of the cassette at the time the input command is given.

When the prescribed input command is received, the pre-programmed rules or algorithms of the control circuit 190 command the motor 188 to rotate in a reverse direction for a set time period and generates a confirmation output with visual indicators (e.g., blinking the reverse green arrow 202). The endovascular staple 36 will be drawn from the cassette 34 into the distal end of the staple applier 38.

The sensing function of the control circuit 190 senses the magnitude of the current drawn by the motor 188 as the staple 36 is being loaded onto the distal end of the staple applier 38. Once a prescribed amount of current has been reached, the pre-programmed rules or algorithms of the control circuit 190 consider the staple applier to have completed the loading state. The pre-programmed rules or algorithms of the control circuit 190 then automatically go into a UNWIND sequence, to reduce or eliminate amount of torque windup in the staple applier catheter and drive shaft developed during the LOAD state. The pre-programmed rules or algorithms of the UNWIND sequence run the motor in the reverse direction from the load direction a set number of turns and wait for a command input.

After the UNWIND sequence, the endovascular staple is presumed loaded, and the pre-programmed rules or algorithms of the control circuit 190 enter a READY TO APPLY state. The pre-programmed rules or algorithms of the control circuit 190 generate a confirmation output, e.g., audible and visual indicators (e.g., two short beeps and a forward green arrow 206 will blink (see FIG. 9B) to prompt the next step, which is to deploy the staple 36.

The endovascular staple 36 is now loaded in the staple applier 38, and the applier 38 can be removed from the cassette 34. The physician is desirably urged by the instructions for use 58 to verify that the endovascular staple 36 is in place by visually inspecting the distal end of the applier 38.

When the staple applier 38 has been powered up and is in the READY TO LOAD state, the pre-programmed rules or algorithms of the control circuit 190 desirably do not accept any command other than the command prescribed for loading (e.g., pushing the reverse control button 194). If an operator provides a contrary command, e.g., by pushing on the forward command button 192, the pre-programmed rules or algorithms of the command circuit will ignore the command. In this way, the pre-programmed rules or algorithms of the command circuit require an operator to follow a prescribed sequence in operating the staple applier.

Read to Apply State: Deploy Staple

When the pre-programmed rules or algorithms of the control circuit 190 have entered the READY TO APPLY state, and the operator is ready to deploy the staple 36, the operator is able to deploy the endovascular staple 36 by initiating a prescribed input command, e.g., by pressing the forward control button 192. When the forward control button 192 is pushed, the pre-programmed rules or algorithms of the control circuit 190 command the motor 188 to rotate in a forward direction for a set number of rotations (sensed by the counting function), which, according to the pre-programmed rules or algorithms, are less than the number of rotations required to fully implant the staple. The pre-programmed rules or algorithms of the control circuit 190 suspend operation of the motor 188 at this point and await another input command. Thus, the pre-programmed rules or algorithms of the control circuit 190 only partially deploy the staple and generate a confirmation output, e.g., four beeps and/or alternatively blinking the forward and reverse arrows 202 and 206, prompting the operator to make a choice. This indicates that the operator may chose to continue deployment or to withdraw the endovascular staple back into the applier.

If the operator inputs a prescribed withdraw command, e.g., by pushing the reverse control button 194, the pre-programmed rules or algorithms of the control circuit 190 drive the motor 188 in the reverse direction for a set number of rotations (sensed by the counting function), to withdraw the staple 36. The pre-programmed rules or algorithms of the control circuit 190 then return to the READY TO APPLY state.

If the operator inputs a prescribed complete the implantation command, e.g. by pushing the forward control button 192, the pre-programmed rules or algorithms of the control circuit 190 will drive the motor 188 in the forward direction for a set number of rotations (monitored by the counting function), to complete the implantation of the staple. The pre-programmed rules or algorithms of the control circuit 190 generate a confirmation output, e.g., audio and visual indicators. The pre-programmed rules or algorithms of the control circuit 190 return to the READY TO LOAD state.

During the different operational states, the pre-programmed rules or algorithms of the control circuit 190 continue to check battery voltage against a set minimum. The operational states proceed as described as long as the battery voltage exceeds the set minimum. If, during an operational state the battery voltage falls below the set minimum, the pre-programmed rules or algorithms of the control circuit 190 enter a LOW BATTERY FATAL state.

D. The Instructions for Use

The instructions for use 58 can direct use of catheter-based technology via a peripheral intravascular access site, such as in the femoral artery, optionally with the assistance of image guidance. Image guidance includes but is not limited to fluoroscopy, ultrasound, magnetic resonance, computed tomography, or combinations thereof.

Figure 12B:
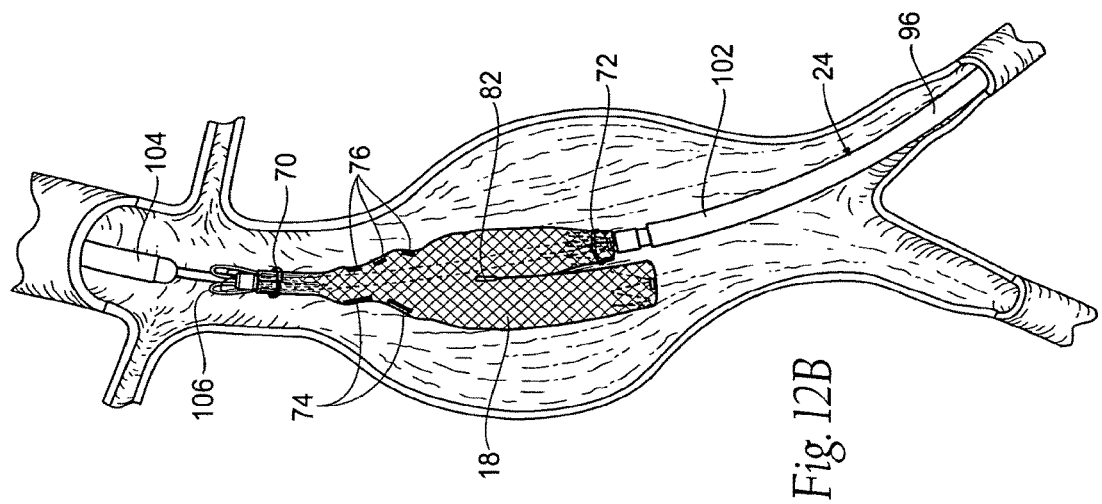
FIGS. 12A to 12P are anatomic views of manipulation of the components of the system shown in FIG. 1 in placing a prosthesis in an abdominal aortic aneurism, which manipulations can be incorporated within an instruction for use associated with a kit like that shown in FIG. 2.
Figure 12A:
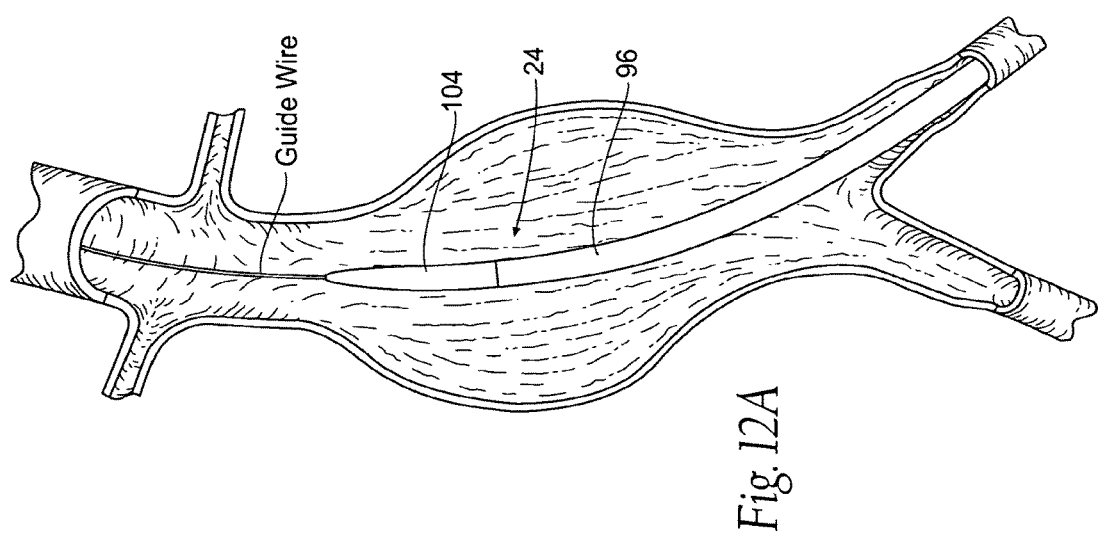
Figure 12D:
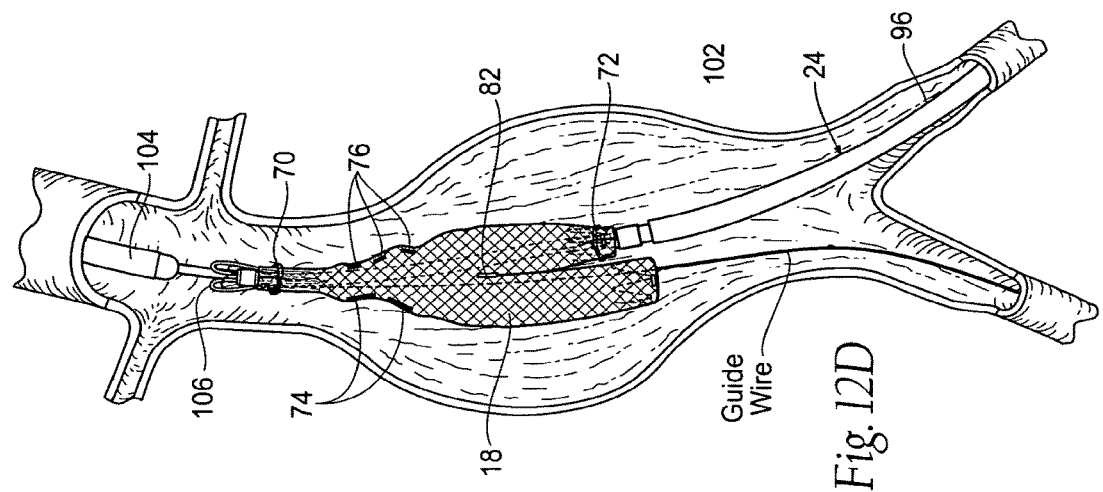
Figure 12C:
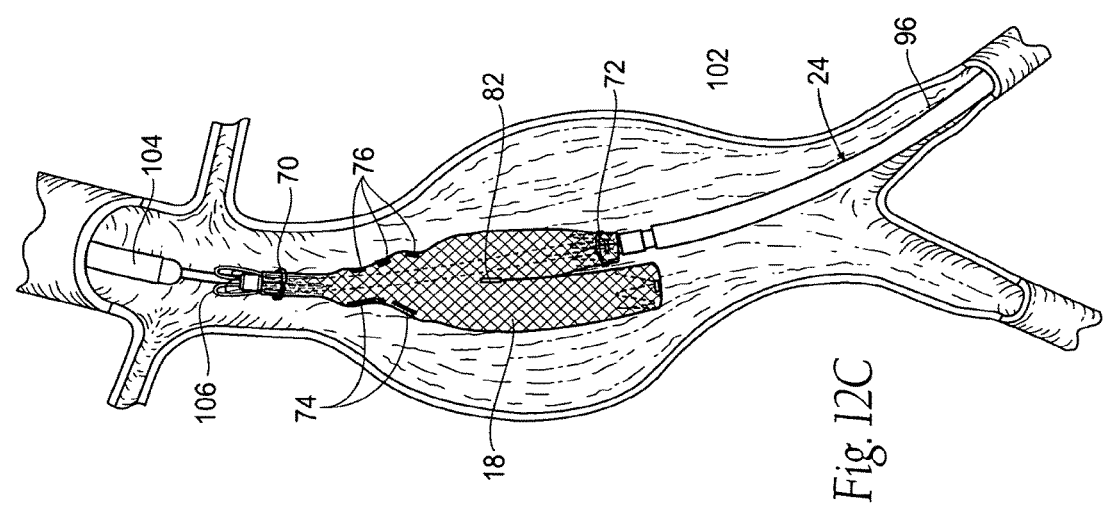
Figure 12F:
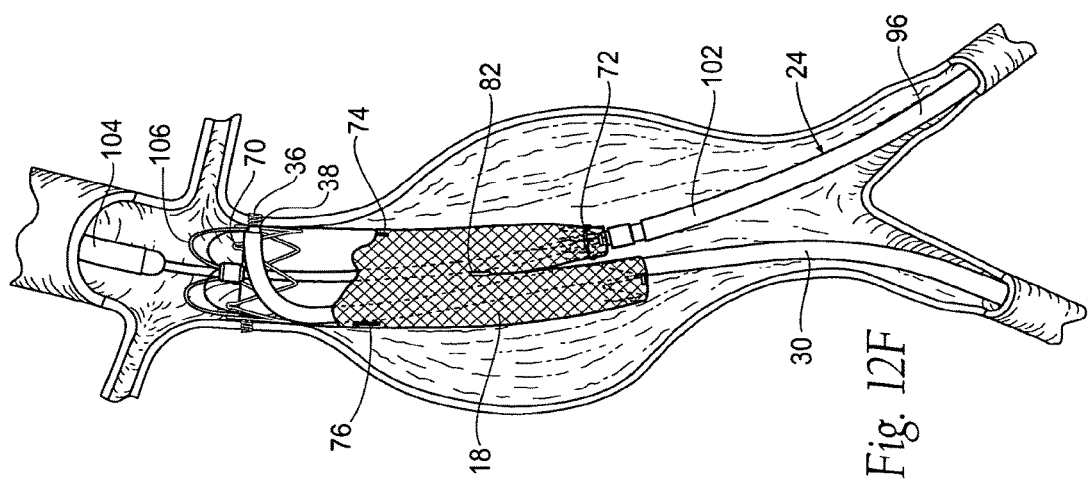
Figure 12E:
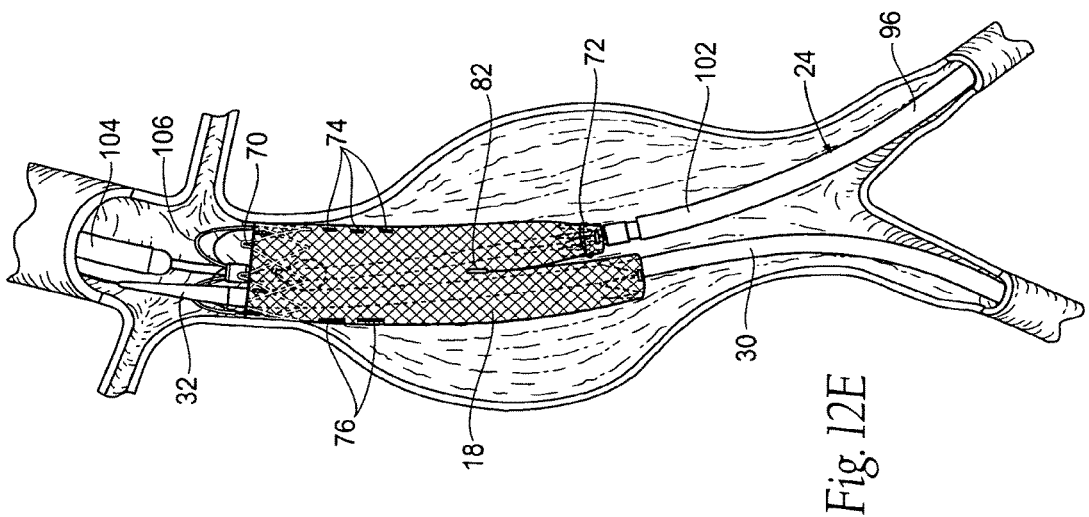
Figure 12K:
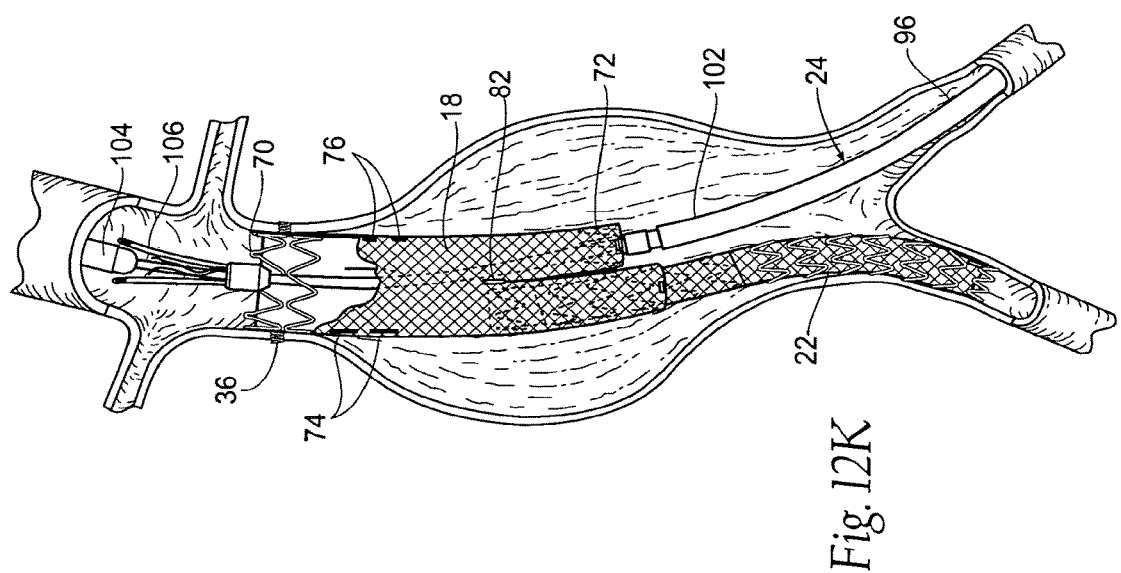
Figure 12L:
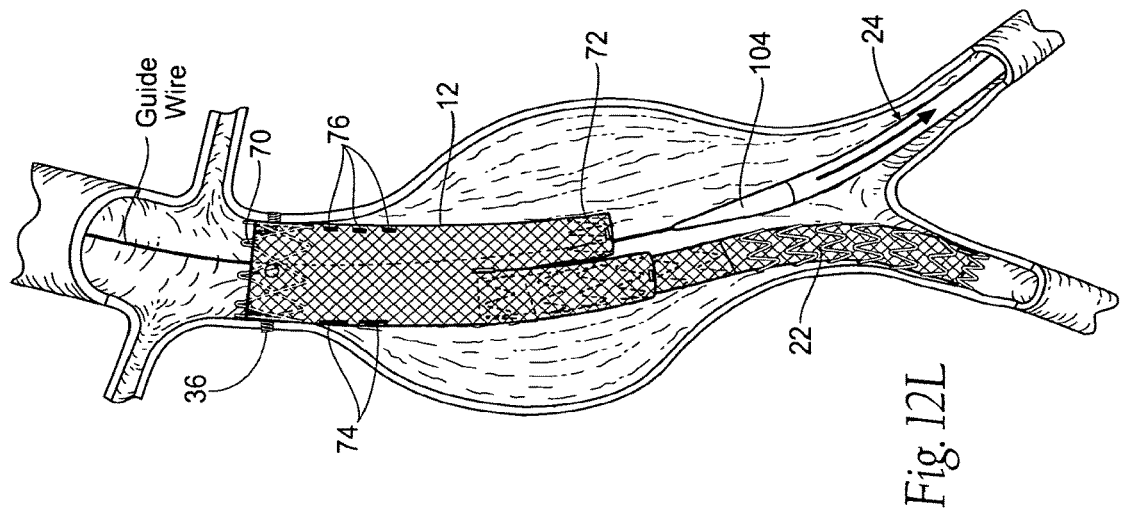
Figure 12N:
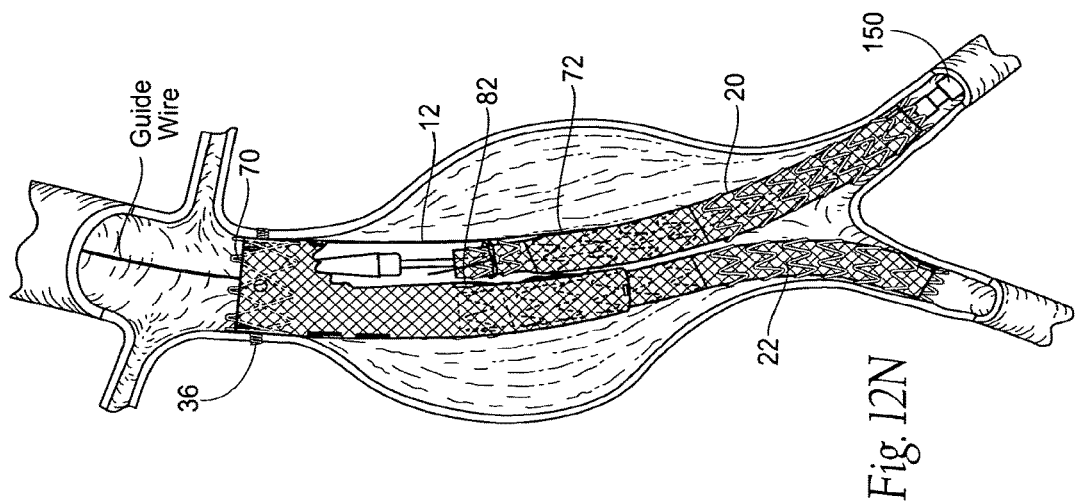
Figure 12M:
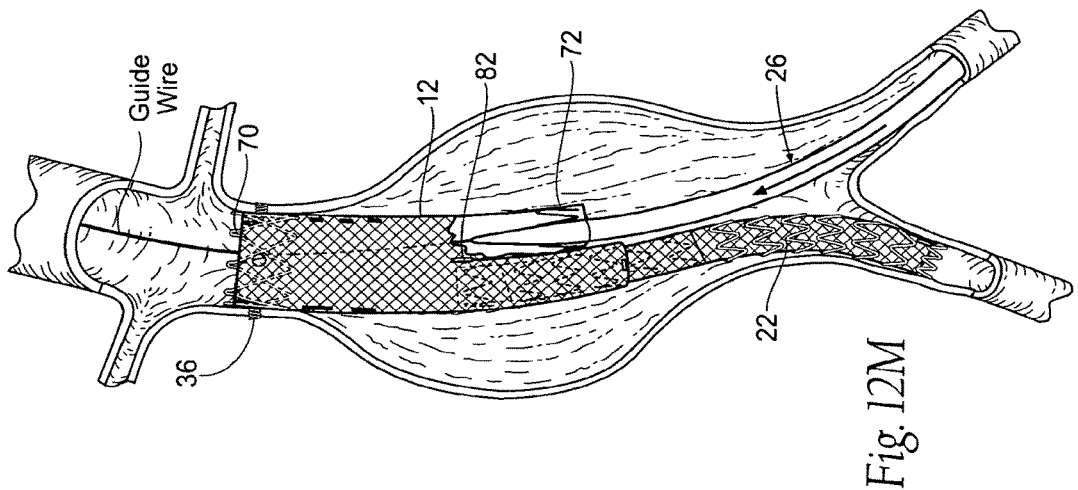
Figure 12P:
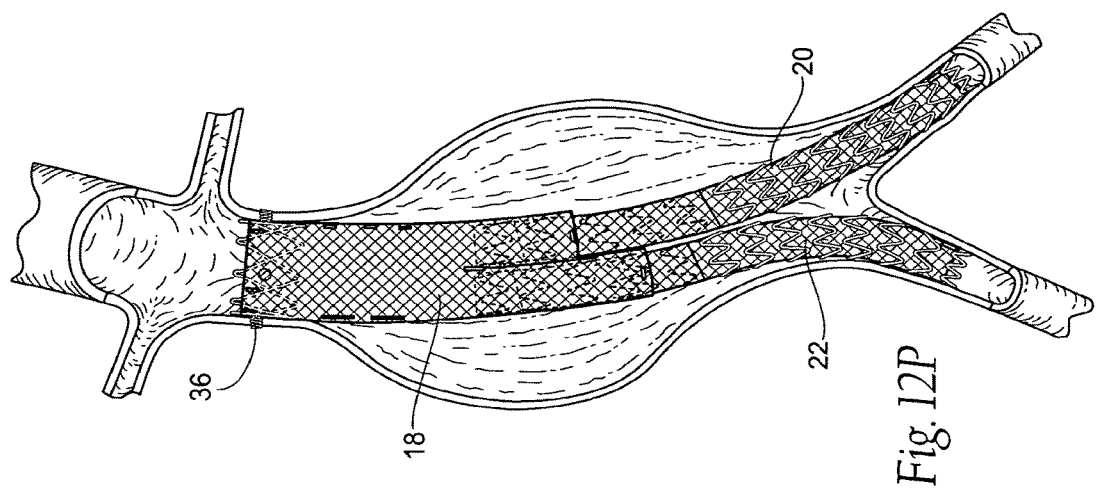

FIGS. 12A to 12P show a representative embodiment of the steps that a representative instructions for use 58 can incorporate or direct.

In a representative embodiment, the instructions for use 58 may include the achievement of percutaneous vascular access by conventional methods into the femoral artery, for example. In this arrangement, the patient is placed on an imaging table, allowing fluoroscopic visualization from the aortic arch to the femoral artery bifurcations. Access is secured to both contralateral and ipsilateral branches by standard techniques using introducer sheaths (which can be supplied as part of the kit 40). Using fluoroscopic guidance, access to the patient's abdominal aorta can be achieved with an appropriately sized guide wire through each femoral access sites.

1. Position the Main Body Graft Assembly in the Targeted Endovascular Treatment Site In this arrangement, the instructions 58 for use may include positioning of the main body 18 of the endovascular graft assembly to be deployed. The instructions may include a series of steps that can be followed to carry out this portion of the procedure. These steps may include:

(i) after flushing the main body delivery system 24 with heparinized saline, positioning the main body delivery system 24 within an aortic aneurysm over the guide wire via the ipsilateral femoral access site, which has been previously established in conventional fashion (FIG. 12A);

(ii) visualizing the proper rotation and orientation of the main body 18 using the ipsilateral and contralateral radiopaque markers on the main body 18. As previously described, the main body 18 includes three (3) short markers 76 on the ipsilateral side and two (2) long markers 74 on the contralateral side for this purpose. The two rows of markers 74 and 76 should be parallel to each other and not cross. The main body delivery system 24 can be rotated for re-alignment of the main body 18 of the graft assembly 12.

(ii) withdrawing the graft retention jacket 102 of the main body delivery system 24 by rotating the jacket retraction knob 124, until the knob 124 spins freely (which indicates that the rack and pinion mechanism has been released). This step only partially retracts the jacket 102 (about 63 mm), unsheathing the proximal stent 70, with the remaining portion of the main body 18 still constrained within the jacket 102. The instructions may note that the proximal sealing stent 70 will not open during retraction of the jacket 102.

(iii) completing the retraction of the graft retention jacket 102 by sliding the jacket retention slide 126 away from the patient. The instructions may note that the contralateral lumen of the main body 18 is now fully open, while the proximal sealing stent 70 and ipsilateral lumen remain collapsed and connected to the main body delivery system 24 (FIG. 12B);

(iv) verifying the position and orientation of the main body 18 using the radiopaque markers 74 and 76, to ensure that blood flow to the renal arteries is not obstructed and the main body 18 of the graft assembly 12 is not twisted; and (v) opening the proximal sealing stent 70 by retracting the proximal sealing stent release slide 114 (FIG. 12C). The instructions may note that the proximal and distal ends of the main body 18 of the endovascular graft assembly 12 still remain secured to the main body delivery system 24. The physician thereby maintains control of the position and orientation of the main body 18 of the graft assembly 12.

2. Deploy Endovascular Staples to Secure the Position of the Main Body of the Graft Assembly The instructions for use 58 may next instruct securing of the position of the proximal end of the main body 18 of the endovascular graft assembly using endovascular staples 36. The instructions may include a series of steps that can be followed to carry out this portion of the procedure. These steps may include:

(i) placing an exchange length appropriately sized guide wire via the contralateral femoral access site into the abdominal aorta (FIG. 12D). The main body 18 of the endovascular graft assembly includes distal end radiopaque markers that outline the opening of the contralateral lumen of the main body 18. The guide wire is to be placed through this opening and its position verified using standard endovascular techniques.

(ii) inserting the obturator 32 into the lumen 168 of the steerable endovascular guide 30.

(iii) using fluoroscopic guidance, advancing the steerable endovascular guide 30 with the obturator 32 over the guide wire into a position within the proximal neck of the aortic aneurism (FIG. 12E). The C-shaped radiopaque marker 172 located at the distal tip of the steerable endovascular guide 30 will aid in fluoroscopic visualization.

(iv) removing the guide wire.

(v) removing the obturator 32 to open the lumen 168 of the steerable endovascular guide 30 for passage of the endovascular staple applier 38.

(vi) deflecting the distal end of the steerable endovascular guide 30 toward the first intended staple implantation area by rotating the deflector knob, while observing with fluoroscopic guidance. The instructions may note that the C-shaped fluoroscopic marker 172 will appear as a straight line when the catheter is oriented laterally, as a right curve "(" when oriented anteriorly, and as a left curve ")" when oriented posteriorly.

(vii) turning on the endovascular staple applier 38 by pressing and holding the reverse control button 194 for at least five (5) seconds. This initiates a self-checking sequence with audible tones and blinking lights. At the end of this sequence, the reverse green arrow 202 will be blinking, indicating that the endovascular staple applier 38 is ready to load the first endovascular staple 36. The instructions may note that, if at the end of the self check sequence, the red error light 204 is illuminated, the endovascular staple applier 38 has encountered an error. The error can be cleared by pressing the forward control button 192. After the error has been cleared, the self check sequence will initiate. If at the end of the second self check sequence, the red error light 202 is still illuminated, the endovascular staple applier 38 is not functional and should not be used.

(viii) after flushing the inner lumen of the endovascular staple applier 38 with heparinized saline via the flush port, loading the staple by pressing the reverse command button 194 on the handle. While the motor 188 is running, insert the distal end of the endovascular staple applier catheter 182 into the open staple port of the cassette 34. The reverse green arrow 202 will blink, and the endovascular staple will be drawn from the cassette into the distal end of the staple applier 38. When the endovascular staple 36 is loaded, an audible tone (e.g., two short beeps) will be heard, and the forward green arrow 206 will blink. This indicates that the endovascular staple 36 is now preloaded in the staple applier 38, and the applier 38 can be removed from the cassette 34. The instructions may urge the physician to verify that the endovascular staple 36 is in place by visually inspecting the distal tip of the applier 38.

Figure 11B:
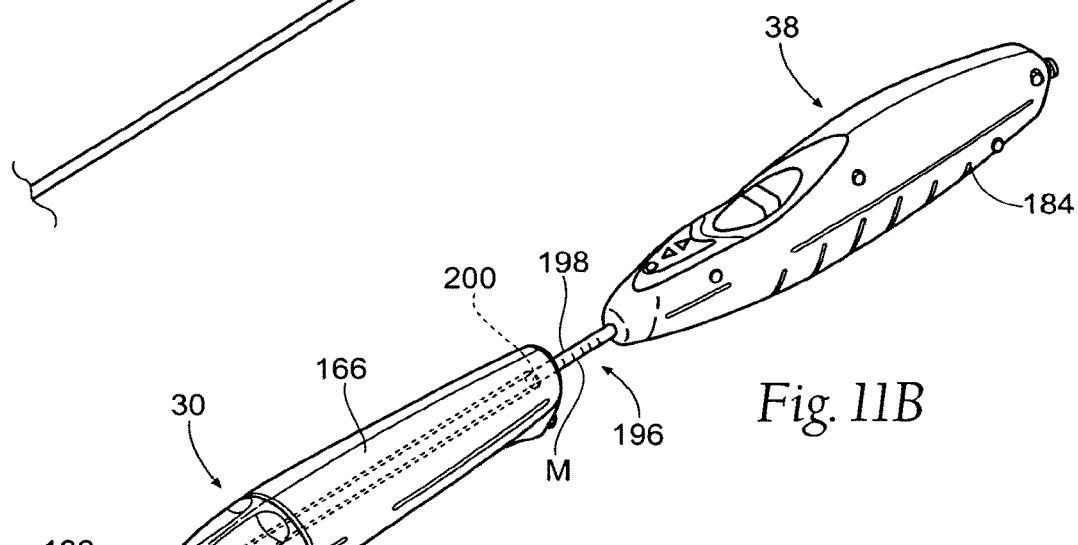
FIG. 11B is a view showing the fastener applier shown in FIG. 11A in association with a steerable endovascular guide of a type shown in FIG. 7A, showing how the indicia, which is visible to a naked eye, marks when the actuated member rests at a desired distance within the guide short of the terminus of the guide and therefore out of contact with tissue.
Figure 11C:
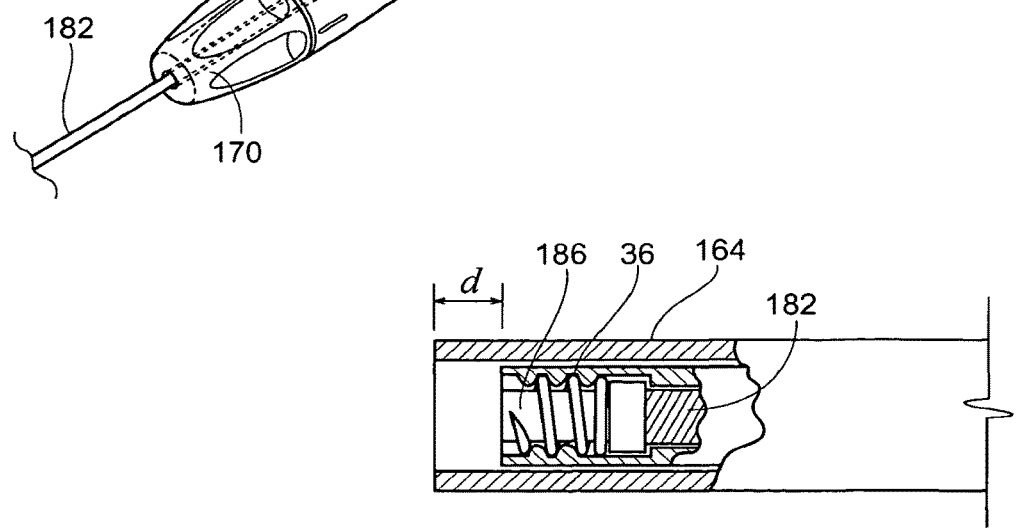
FIG. 11C shown the distal end of the guide when the indicia visible at the proximal end of the guide marks when the actuated member rests at a desired distance within the guide short of the terminus of the guide and therefore out of contact with tissue.

(ix) while stabilizing the control handle 166 of the endovascular guide 30 relative to the patient, inserting the now-loaded endovascular staple applier 38 through the hemostatic seal at the proximal end of the steerable endovascular guide control handle 166. The instructions may direct the physician to observe the location of the visible contrast-color tubing 198 or other indicia on the proximal end of the applier catheter 182 and to halt further insertion of the staple applier 38 when the end of the contrast-color tubing 198 registers with the insertion port/hemostatic seal on the handle of the steerable endovascular guide (as shown in FIG. 11B). This indicates that the distal end of applier catheter 182 rests in a desired short inset distance within the distal end of the guide tube 164 (as shown in FIG. 11C).

(x) inserting and positioning the steerable endovascular guide 30 at the desired location for endovascular staple implantation within a desired stapling zone, e.g., between the marker bands on the proximal sealing stent 70 and the bottom edge of the proximal sealing stent 70. The instructions may note that the endovascular staples should be evenly distributed around the circumference of the proximal sealing stent 70, typically about 4 to 6 endovascular staples per graft.

(xi) under fluoroscopic guidance, advancing the endovascular staple applier 38 through the steerable endovascular guide 30 until the endovascular staple applier 38 emerges from the distal end and contacts the endovascular graft assembly 12. Slowly, continue to advance the endovascular staple applier 38 until resistance is felt, indicating that the endovascular staple applier 38 is firmly pushing against the main body 18 of the endovascular graft assembly 12 against the vessel wall.

(xii) using the control handle 184 of the endovascular staple applier 38, pressing the forward control button 192 for achieving the first stage of endovascular staple deployment. The endovascular step will partially deploy and pause. An audible tone is heard (e.g., four beeps) and the forward and reverse arrows 202 and 206 will alternatively blink, indicating that the operator may continue deployment or withdraw the endovascular staple 36 back into the applier 38. The instructions may note that, in the event of a power loss when the staple 36 is partially deployed, the staple may be removed by manually rotating the handle 184 and catheter 182 in a counter-clockwise direction until the staple 36 disengages from the graft and tissue. The staple applier 38 can be removed from the endovascular guide 30 in this condition.

(xiii) If the endovascular staple 36 is not in the desired location, pressing the reverse control button 194 to re-house the staple inside the staple applier 38 for re-positioning.

(xiv) If the endovascular staple 36 is in the desired position, completing the final stage of staple deployment by pressing the forward control button 192 (FIG. 12F). When complete, an audible tone (e.g., three beeps) is heard and the reverse green arrow 202 will be blinking.

(xv) using fluoroscopy, carefully and slowly retracting the endovascular staple applier 38 away from the graft wall to ensure it is released from the deployed staple.

(xvi) removing the endovascular staple applier 38, leaving the steerable endovascular guide 30 in place.

(xvii) using fluoroscopy, visually confirming that the endovascular staple 36 is in place.

(xviii) as needed, flush the steerable endovascular guide and the staple applier with heparinized saline to prevent clotting in the lumens.

(xix) rotating the head of the cassette 34 (as shown in FIG. 8C) clockwise to expose the next endovascular staple port. Load the next endovascular staple in the manner described above.

(xx) repositioning the steerable endovascular guide 30 to the next desired implantation site for an endovascular staple 36. Desirably, the physician straightens the steerable endovascular guide 30 between rotating in within the main body 18, to prevent accidental dislodgment or movement of the main body 18.

(xxi) deploying the next endovascular staple 36 through the steerable endovascular guide 30 in the manner described above. Typically, 4 to 6 endovascular staples, evenly distributed about the circumference of the main body 18, will serve to secure the position of the main body 18 within the vessel (FIG. 12G).

(xxii) after deployment of the last endovascular staple, removing the endovascular stapler applier 38 from the steerable endovascular guide 30.

(xxiii) re-advancing the obturator 32 and then the guide wire into the steerable endovascular guide.

(xxiv) removing the steerable endovascular guide 30 and the obturator 32, leaving the guide wire in position.

3. Deploy the Contralateral Lumen Extension

The instructions for use 58 may next include the deployment of the contralateral lumen extension 22 of the endovascular graft assembly. The instructions may include a series of steps that can be followed to carry out this portion of the procedure. These steps may include:

(i) after flushing with heparinized saline, advancing the contralateral lumen extension delivery system 28 over the guide wire in the contralateral femoral access site (FIG. 12H).

(ii) using fluoroscopic guidance, aligning the proximal marker 94 on the lumen extension 22 with the insertion depth marker 92 located medially on the main body 18.

(iii) holding the lumen extension deliver system 28 stable relative to the patient, retracting the jacket retraction slide 162 away from the patient to unsheath the lumen extension 22 (FIG. 12I). The distal end of the lumen extension 22 will deploy. The proximal end of the lumen extension 22 will remain collapsed and secured to the delivery system 28.

(iv) retracting the proximal stent release slide 156 to release the proximal end of the lumen extension 22 and complete the deployment of the lumen extension (FIG. 12J).

(v) rejacketing the lumen extension delivery system by holding the jacket retention slide 162 and slowly retracting the delivery system 28, until the nosecone seals into the proximal end of the jacket 150.

(vi) maintaining forward pressure on the jacket retention slide 162, removing the lumen extension delivery system 28 from the patient, leaving the guide wire and femoral access introducer sheath in place.

4. Complete the Deployment of the Main Body

The instructions for use 58 may next include the completion of the deployment of the main body 18 of the endovascular graft assembly, which remains in a secured but partially deployed condition during the deployment of the contralateral lumen extension 22, as above described. The instructions may include a series of steps that can be followed to carry out this portion of the procedure. These steps may include:

(i) moving to the ipsilateral femoral access site, where the main body delivery system 24 resides.

(ii) releasing the stabilizing arms 106 from the graft by retracting the graft release slide 116 on the handle of the delivery system away from the patient (FIG. 12K).

(iii) releasing the main body ipsilateral lumen from the delivery system by retracting the ipsilateral release slide 118 on the handle away from the patient (FIG. 12L). The main body 18 is now fully released (FIG. 12K).

(iv) rejacketing the main body delivery system 24 by holding the jacket retention slide 126 and slowly retract the main body 18 delivery system, until the nosecone seals into the proximal end of the jacket 102.

(vi) maintaining forward pressure on the jacket retention slide 126, remove the main body delivery system 24 from the patient (FIG. 12L), leaving the guide wire and femoral access introducer sheath in place.

5. Deploy the Ipsilateral Lumen Extension

The instructions for use 58 may next include the deployment of the ipsilateral lumen extension 20 of the endovascular graft assembly 12. The instructions may include a series of steps that can be followed to carry out this portion of the procedure. These steps may include:

(i) after flushing with heparinized saline, advancing the ipsilateral lumen extension delivery system 26 over the guide wire in the ipsilateral femoral access site (FIG. 12M).

(ii) using fluoroscopic guidance, aligning the proximal marker 92 on the lumen extension 20 with the insertion depth marker 82 located medially on the main body 18.

(iii) holding the lumen extension deliver system stable relative to the patient, retracting the jacket retraction slide 162 away from the patient to unsheath the lumen extension 20 (FIG. 12N). The distal end of the lumen extension 20 will deploy. The proximal end of the lumen extension 20 will remain collapsed and secured to the delivery system 26.

Figure 12O:
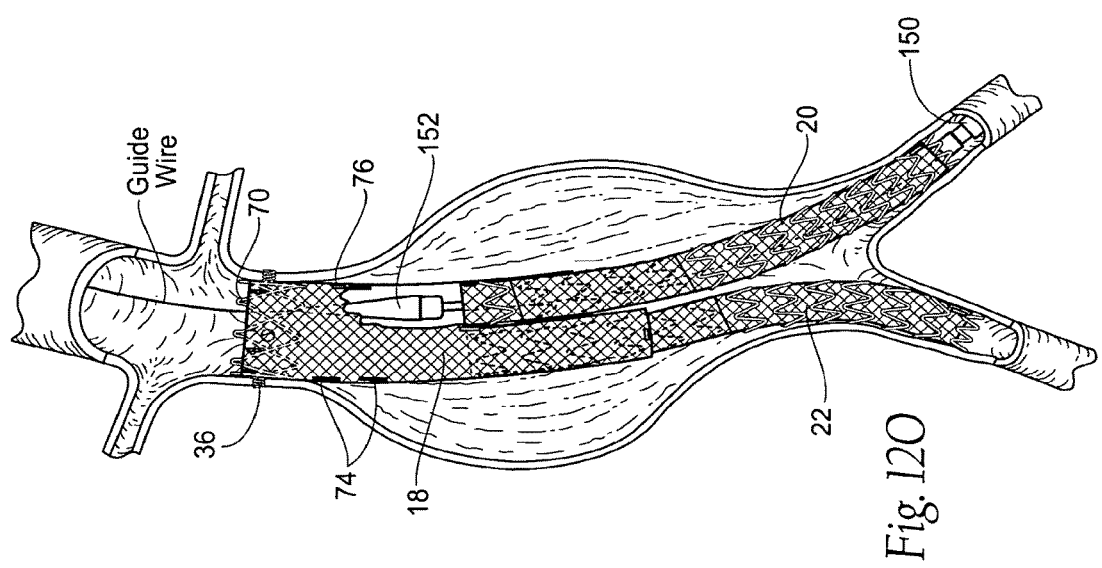

(iv) retracting the proximal stent release slide 156 to release the proximal end of the lumen extension 20 and complete the deployment of the lumen extension (FIG. 12O).

(v) rejacketing the lumen extension delivery system 26 by holding the jacket retention slide 162 and slowly retracting the delivery system 26, until the nosecone seals into the proximal end of the jacket 150.

(vi) maintaining forward pressure on the jacket retention slide 162, removing the lumen extension delivery system 26 from the patient, leaving the guide wire and femoral access introducer sheath in place.

6. Completion of the Procedure

The instructions for use 58 may next include the completion of the procedure. The instructions may include a series of steps that can be followed to carry out this portion of the procedure. These steps may include:

(i) performing post-implant aortic angiography to evaluate the implantation.

(ii) checking for endovascular leaks around the endovascular graft assembly. If a leak is observed, standard endovascular techniques can be used to resolve. Additional staples may be placed, in the manner described above.

(iii) checking for proper location, blood flow, and patency of the endovascular graft assembly.

(iv) removing the guide wires and femoral access sheaths and close the femoral arteriotomies according to standard practice (FIG. 12P).

It is to be appreciated that the general steps just described do not necessarily need to follow the order in which they were described. It is also to be appreciated that fasteners may be applied to the lumen extensions as well as to connect the lumen extensions to the iliac arteries.

It will also be appreciated that the components and/or features of the preferred embodiments described herein may be used together or separately, while the depicted methods and devices may be combined or modified in whole or in part. It is contemplated that the components of the guiding device, fastener device, and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device within the vascular system and generally within the body.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The desired embodiments of the invention are described above in detail for the purpose of setting forth a complete disclosure and for the sake of explanation and clarity. Those skilled in the art will envision other modifications within the scope and spirit of the present disclosure.

We claim:

1. A seal assembly for an endovascular device, the seal assembly comprising:
   a first seal component comprising a center post and a collar that extends radially from an end of the center post, wherein the collar comprises at least one guide tube formed therethrough, the at least one guide tube being radially outward of the center post;
   a second seal component with at least one guide tube formed therethrough, the second seal component registering with the first seal component with the at least one guide tube in the second component coaxially aligned with the at least one guide tube in the first component; and
   a septum sandwiched between the first and second seal components, the septum accommodating passage of a control filament from one of the coaxially aligned guide tubes, through the septum, to the other one of the coaxially aligned guide tubes, thereby providing a fluid seal for the control filament, the center post of the first seal component passing through the septum.

2. The assembly of claim 1, wherein at least one of the first and second seal components is substantially rigid.

3. The assembly of claim 2, wherein the septum comprises a soft material.

4. The assembly of claim 2, wherein the septum comprises silicone rubber.

5. The assembly of claim 2, wherein the septum comprises a gasket.

6. The assembly of claim 1, wherein both of the first and second seal components are substantially rigid.

7. The assembly of claim 6, wherein the septum comprises a soft material.

8. The assembly of claim 6, wherein the septum comprises silicone rubber.

9. The assembly of claim 6, wherein the septum comprises a gasket.

10. The assembly of claim 1, wherein the second seal component comprises an annular ring that fits about the center post.

11. The assembly of claim 1, wherein the septum is disposed about the center post.

12. The assembly of claim 1, wherein both the first seal component and the second seal component include coaxial guide tubes to accommodate passage of the control filament.

13. The assembly of claim 12, wherein the guide tubes act as bearing surfaces or guides for the control filament.

14. The assembly of claim 1, wherein the collar and the center post are integral.

15. An endovascular apparatus comprising:
   a catheter assembly including an operative element that, in use, is exposed to a body fluid;
   a control element;
   a control filament coupled at one end to the control element and at an opposite end to the operative element; and
   a seal assembly between the control element and the operative element through which the control filament passes to prevent contact between the body fluid and the control element, the seal assembly comprising:
      a first seal component comprising a center post and a collar that extends radially from an end of the center post, wherein the collar comprises at least one guide tube formed therethrough, the at least one guide tube being radially outward of the center post;
- a second seal component with at least one guide tube formed therethrough, the second seal component registering with the first seal component with the at least one guide tube in the second component coaxially aligned with the at least one guide tube in the first component; and
- a septum sandwiched between the first and second seal components, the septum accommodating passage of the control filament from one of the coaxially aligned guide tubes, through the septum, to the other one of the coaxially aligned guide tubes, thereby providing a fluid seal for the control filament, the center post of the first seal component passing through the septum.

16. The apparatus of claim 15, further comprising:
- a flush passage passing through the seal assembly for conveying a heparinized saline to flush the operative element prior to deployment.

17. The apparatus of claim 16, wherein the center post defines a passage that sealingly engages the flush passage.

18. The apparatus of claim 17, wherein the second seal component comprises an annular ring that fits about the center post.

19. The apparatus of claim 17, wherein the septum is disposed about the center post.

20. The apparatus of claim 15, wherein both the first seal component and the second seal component include coaxial guide tubes to accommodate passage of the control filament.

21. The apparatus of claim 15, wherein the guide tubes act as bearing surfaces or guides for the control filament.

22. The apparatus of claim 15, wherein the control filament comprises at least one release wire for one of a sealing stent, a graft, and a lumen.

23. The apparatus of claim 15, wherein the seal assembly comprises a dynamic seal that prevents contact between the body fluid and the control element even if the control filament is tensioned in a non-axial direction during operation.

* * * * *